(12) United States Patent
Seeley et al.

(10) Patent No.: US 7,713,986 B2
(45) Date of Patent: May 11, 2010

(54) COMPOUNDS AND METHODS FOR TREATMENT OF CHEMOTHERAPY-INDUCED ANEMIA

(75) Inventors: Todd W. Seeley, Moraga, CA (US); David Y. Liu, Palo Alto, CA (US); Stephen J. Klaus, San Francisco, CA (US)

(73) Assignee: FibroGen, Inc., San Francisco, CA (US)

( * ) Notice: Subject to any disclaimer, the term of this patent is extended or adjusted under 35 U.S.C. 154(b) by 0 days.

(21) Appl. No.: 11/455,200

(22) Filed: Jun. 15, 2006

(65) Prior Publication Data

US 2007/0292433 A1     Dec. 20, 2007

(51) Int. Cl.
*A61K 31/505*     (2006.01)

(52) U.S. Cl. .......................................... 514/269; 514/2

(58) Field of Classification Search ........................ None
See application file for complete search history.

(56) References Cited

U.S. PATENT DOCUMENTS

2003/0153503 A1*    8/2003    Klaus et al. .................... 514/12

FOREIGN PATENT DOCUMENTS

| WO | WO-02/074981 | A2 | 9/2002 |
| WO | WO-03/049686 | A3 | 6/2003 |
| WO | WO-03/053997 | A2 | 7/2003 |
| WO | WO-2004/108121 | A1 | 12/2004 |
| WO | WO-2004/108681 | A1 | 12/2004 |

OTHER PUBLICATIONS

Ferrario et al, Cancer Treat Rev, 2004, 30:563-575.*

Bohlius, Julia, et al., "Recombinant Human Erythropoietin and Overall Survival in Cancer Patients: Results of a Comprehensive Meta-Analysis," J Natl Cancer Inst, vol. 97, No. 7, 2005, pp. 489-498.

Glaspy, "The Development of Erythropoietic Agents in Oncology," Expert Opin. Emerging Drugs, vol. 10, No. 3, 2005, pp. 553-567.

Ivan, Mircea, et al., "HIFa Targeted for VHL-Mediated Destruction by Proline Hydroxylation: Implications for O2 Sensing," Science, vol. 292, Apr. 2001, pp. 464-468.

Ivan, Mircea, et al., "Biochemical Purification and Pharmacological Inhibition of a Mammalian Prolyl Hydroxylase Acting on Hypoxia-Inducible Factor," PNAS, vol. 99, No. 21, Oct. 2002, pp. 13459-13464.

Oberhoff, C., et al., "Recombinant Human Erythropoietin in the Treatment of Chemotherapy-Induced Anemia and Prevention of Transfusion Requirement Associated With Solid Tumors: A Randomized, Controlled Study," Ann Oncol, vol. 9, 1998, pp. 255-260.

Seeley, Todd W., et al., "Tumor Progression Studies and Correction of Anemia of Chronic Disease in Xenograft Models," ASN Abstract, Nov. 2005.

Seki, Teruya, et al., "Phenanthrolines," Chem Abstracts, vol. 81, No. 21, 1974, pp. 424.

Wun, Ted, et al., "Increased Incidence of Symptomatic Venous Thrombosis in Patients With Cervical Carcinoma Treated With Concurrent Chemotherapy, Radiation and Erythropoietin," Cancer, vol. 98, No. 7, Oct. 2003, pp. 1514-1520.

* cited by examiner

*Primary Examiner*—Misook Yu
*Assistant Examiner*—Mark Halvorson
(74) *Attorney, Agent, or Firm*—James E. Nesbitt; Christopher T. Jacob

(57) ABSTRACT

The invention relates to methods and compounds for treating chemotherapy-induced anemia. In particular, methods for treating chemotherapy-induced anemia in subjects refractory to treatment with recombinant human erythropoietin are encompassed herein.

8 Claims, 6 Drawing Sheets

COMPOUNDS AND METHODS FOR TREATMENT OF CHEMOTHERAPY-INDUCED ANEMIA

FIELD OF THE INVENTION

The invention relates to methods and compounds for treating chemotherapy-induced anemia. In particular, methods for treating chemotherapy-induced anemia in subjects refractory to treatment with recombinant human erythropoietin are encompassed herein.

BACKGROUND OF THE INVENTION

Chemotherapeutic agents are known suppressors of red cell production by the bone marrow, and over 60% of patients treated with chemotherapy develop anemia resulting in decreased functional capacity and quality of life. In contrast to other common side effects experienced by patients undergoing treatment for cancer, chemotherapy-induced anemia (CIA) is often a "silent" side effect with insidious symptoms. CIA can be one of the most common underlying etiologies of the fatigue in cancer patients. Most chemotherapeutic agents also cause stomach upset, resulting in nausea and vomiting, which can severely reduce appetite and produce substantial weight loss in the patient. CIA is also associated with cognitive dysfunction, dyspnea, and depression. As a result of this reduced quality of life, some patients choose to discontinue or delay chemotherapeutic treatment, increasing the potential for suboptimal outcomes. Also, CIA can adversely affect long-term outcomes in some patients, as the anemic environment may limit the effectiveness of some chemotherapy agents.

The incidence and severity of CIA depend on a variety of factors, including the type, schedule, and intensity of therapy administered, or whether the patient has received prior myelosuppressive chemotherapy, radiation therapy, or both. Approximately 1.3 million cancer patients undergo chemotherapy every year in the United States, and approximately 67 percent become anemic. Similarly, approximately 63 percent of European chemotherapy patients develop anemia as a result of their treatment.

Although chemotherapy-induced anemia is one of the most common side effects of chemotherapy, it is often not recognized and is frequently under-treated. Treatments can include red blood cell transfusions, which may result in clinical or subclinical adverse effects in the recipients. Several clinical trials have demonstrated that treatment with erythropoeitic agents can reduce the need for blood transfusions and their associated complications in patients undergoing chemotherapy. Daily subcutaneous administration of recombinant human EPO administration at a dose of 5000 IU increases hemoglobin levels and reduces transfusion requirements in chemotherapy-induced anemia, especially during platinum-based chemotherapy. (Oberhoff et al. (1998) Ann Oncol 9:255-260.) However, clinical trials have suggested that a measurable increase in thrombotic complications occurs in chemotherapy-induced anemia patients treated with recombinant human EPO (rhEPO). (Wun et al. (2003) Cancer 98:1514-1520.) The overall impact on thrombosis risk has been confirmed in an independent meta-analysis of rhEPO data. (Bohlius et al. (2005) J Natl Cancer Inst 97(7):489-98.) Furthermore, it is estimated that 30% to 50% of patients undergoing chemotherapy and receiving recombinant human EPO treatment are hyporesponsive or refractory to the recombinant EPO therapy. (J. Glaspy (2005) Expert Opin. Emerging Drugs 10:553-567.) Such patients may then have to undergo treatment with blood transfusions, which is associated with certain risks, including transfusion-transmitted infection, incorrect blood transfusion, acute or delayed transfusion reaction, post-transfusion purpura, transfusion-associated graft-verses-host disease, etc. Thus, a need remains for effective treatments for chemotherapy-induced anemia. In particular, there is a need for effective treatments for chemotherapy-induced anemia in subjects refractory to EPO therapy.

SUMMARY OF THE INVENTION

The present invention provides methods for treating or preventing chemotherapy-induced anemia in a subject in need. In various embodiments, the methods comprise treating or preventing chemotherapy-induced anemia in a subject, the method comprising administering to the subject an effective amount of an agent that inhibits HIF hydroxylase activity.

For purposes of this invention, a subject in need is a patient who has or who is at risk for having chemotherapy-induced anemia. In various aspects, a subject particularly suitable for treatment using the present methods and compounds is a subject who is undergoing, has undergone, or will undergo chemotherapy.

It is specifically contemplated herein that the chemotherapy comprises, in various aspects, administration of a chemotherapeutic selected from the group consisting of: an alkylating agent; a nitrosoureas; an antimetabolite; an anthracyclines; a topoisomerase II inhibitor; a mitotic inhibitor; an anti-estrogen; a progestin; an aromatase inhibitor; an anti-androgen; an LHRH agonist; a corticosteroid hormone; a DNA alkylating agent; a taxane; a vince alkaloid; and a microtubule poison. In certain embodiments, the chemotherapeutic is selected from the group consisting of busulfan, cisplatin, carboplatin, chlorambucil, cyclophosphamide, ifosfamide, dacarbazine (DTIC), mechlorethamine (nitrogen mustard), melphalan, temozolomide, carmustine (BCNU), lomustine (CCNU), 5-fluorouracil, capecitabine, 6-mercaptopurine, methotrexate, gemcitabine, cytarabine (ara-C), fludarabine, pemetrexed, daunorubicin, doxorubicin (Adriamycin), epirubicin, idarubicin, mitoxantrone, topotecan, irinotecan, etoposide (VP-16), teniposide, paclitaxel, docetaxel, vinblastine, vincristine, vinorelbine, prednisone, dexamethasone, L-asparaginase, dactinomycin, thalidomide, tretinoin, imatinib (Gleevec), gefitinib (Iressa), erlotinib (Tarceva), rituximab (Rituxan), bevacizumab (Avastin), tamoxifen, fulvestrant, anastrozole, exemestane, letrozole, megestrol acetate, bicalutamide, flutamide, leuprolide, and goserelin.

A subject suitable for treatment with the present methods and compounds is a subject who is undergoing, has undergone, or will undergo chemotherapy and who is refractory to or is at risk for being refractory to recombinant human EPO therapy. Whether or not a subject is refractory to recombinant human EPO therapy can be determined by an assessment of the subject's response or predicted response to treatment with recombinant human EPO. For example, in particular embodiments, the subject is a subject refractory to treatment with rhEPO if the subject displays an increase in hemoglobin concentration of less than 2 g/dl, or fails to reach levels of at least 12 g/dl, after undergoing a regimen of dosing with recombinant human EPO. In a particular embodiment, the response desired upon treatment with recombinant EPO can be defined as an increase in hemoglobin of at least 2 g/dl over a twelve (12) week dosing regimen. If a subject does not display such a response within the required period of time, that subject is deemed refractory to treatment with recombinant human EPO. (See, e.g., Ludwig et al. (1994) Blood 84:1056-1063.)

The value of the desired increase in hemoglobin, which can be used to determine whether or not a particular subject is refractory to recombinant human EPO treatment, may vary depending on a number of factors, including age and gender. Thus, in various embodiments of the present invention, a subject can be a subject refractory to treatment with recombinant human EPO if treatment with recombinant human EPO according to a specific dosing regimen fails to increase the subject's hemoglobin level by at least 0.1-5.0 g/dL. In some embodiments, a subject is refractory to treatment with recombinant human EPO if such treatment fails to increase the subject's hemoglobin level by an amount of at least 0.2-5.0, 0.5-5.0, 1.0-5.0, 1.5-5.0, 2.0-5.0, 3.0-5.0 or 4.0-5.0 g/dL. According to further embodiments, the subject is a subject refractory to therapy using recombinant human EPO therapy if such therapy fails to increase the subject's hemoglobin level by an amount of at least 0.2-2.5, 0.4-2.5, 0.6-2.5, 0.8-2.5, 1.0-2.5, 1.2-2.5, 1.4-2.5, 1.6-2.5, 1.8-2.5, or 2-2.5 g/dL, respectively. Finally, in certain embodiments, the subject is a subject refractory to recombinant human EPO therapy if such therapy fails to raise the subject's hemoglobin to at least desired levels of at least 1.0-2.0, 1.1-2.0, 1.2-2.0, 1.3-2.0, 1.4-2.0, 1.5-2.0, 1.6-2.0, 1.7-2.0, 1.8-2.0, or 1.9-2.0 g/dL, respectively.

Other parameters can be used to determine whether a particular subject is refractory to recombinant human EPO therapy. For example, current guidelines relating to recombinant human EPO administration define target hemoglobin levels for an adult subject as 12 gm/dL. Therefore, in one embodiment, a subject is a subject refractory to recombinant human EPO therapy if treatment with acceptable doses over a specific period of time fails to increase hemoglobin to at least 12 gm/dL. In other embodiments, a subject is a subject refractory to recombinant human EPO therapy if treatment with acceptable doses over a specific period of time fails to increase hemoglobin to at least 10 gm/dL, or at least 11 gm/dl·L.

Similarly, current guidelines for recombinant human EPO administration define a target hematocrit for an adult subject as a hematocrit of 36%. Thus, it is contemplated that, in certain embodiments, a subject is refractory to treatment with recombinant human EPO if dosing with recombinant human EPO fails, over a specified period of time, to raise the subject's hematocrit level to at least 36%. In various embodiments, the subject is refractory to treatment with recombinant human EPO if a recombinant human EPO dosing regimen fails to raise the subject's hematocrit to at least 30%, at least 33%, at least 36%, at least 39%, and at least 42%, respectively.

It is understood that, in view of the discussion, supra, subjects suitable for treatment with the present methods and compounds, e.g., subjects refractory to treatment with recombinant human EPO, methods and compounds provided herein for treating such subjects specifically encompass methods and compounds capable of increasing the subject's hematocrit, hemoglobin, red blood cell count, reticulocyte count, etc., to desired or recommended levels. Failure to meet desired levels of any of these factors through dosing with recombinant human EPO can also be used, singly or in combination, to determine whether a subject is or may be refractory to treatment with recombinant human EPO. For example, in one aspect, a subject is a refractory subject suitable for treatment using the present methods if, after two weeks of therapy, the subject has a serum EPO level of or less than 100 mU/mL, and has demonstrated an increase in hemoglobin of less than 0.5 g/dL. In another aspect, the subject is a subject refractory to recombinant human EPO therapy if, after two weeks of recombinant EPO therapy, the subject displays a serum ferritin level of greater than or equal to 400 ng/ml.

The invention provides in one embodiment a method for reducing weight loss in a subject who is undergoing, has undergone, or is expected to undergo chemotherapy, the method comprising administering to the subject an effective amount of an agent that inhibits HIF hydroxylase activity.

In various embodiments, an agent for use in the present methods is a 2-oxoglutarate mimetic. In certain embodiments, the agent used in the present methods is a compound selected from the group consisting of the compounds of Formula I, Formula II, Formula III, and Formula IV. Formula I includes, but is not limited to, compounds of Formulae Ia, Ib, Ic, Id, and Ie; compounds of Formula Ie include, but are not limited to, compounds of Formulae Ie(i), Ie(ii), Ie(iii), and Ie(iv). Formula III includes but is not limited to, the compounds of Formula IIIa.

In particular embodiments, an agent of the present invention is selected from the group consisting of a pyridine-2-carboxamide, a quinoline-2-carboxamide, an isoquinoline-3-carboxamide, a cinnoline-3-carboxamide, a beta-carboline-3-carboxamide, and a 4-oxo-[1,10]-phenanthroline.

In particular embodiments, an agent for use in the present methods is selected from the group consisting of: Compound A [(1 Chloro-4-hydroxy-isoquinoline-3-carbonyl)-amino]-acetic acid]; Compound B [((S)-2-[(4-Hydroxy-7-phenoxy-6,7-dihydro-isoquinoline-3-carbonyl)-amino]-propionic acid]; Compound C [{[4-Hydroxy-7-(4-methoxy-phenoxy)-isoquinoline-3-carbonyl]-amino}-acetic acid]; Compound D [[(4-Hydroxy-1-methyl-7-phenoxy-isoquinoline-3-carbonyl)-amino]-acetic acid]; Compound E [[7-(4-Fluoro-phenoxy)-4-hydroxy-isoquinoline-3-carbonyl]-amino-acetic acid]; Compound F [4-Oxo-1,4-dihydro-[1,10]phenanthroline-3-carboxylic acid], Compound G [3-{[4-(3,3-Dibenzyl-ureido)-benzenesulfonyl]-[2-(4-methoxy-phenyl)-ethyl]-amino}-N-hydroxy-propionamide], Compound H [[(7-Chloro-3-hydroxy-quinoline-2-carbonyl)-amino]-acetic acid], Compound I [[(1-Chloro-4-hydroxy-7-methoxy-isoquinoline-3-carbonyl)-amino]-acetic acid], Compound J [[(6,7-Dichloro-4-hydroxy-isoquinoline-3-carbonyl)-amino]-acetic acid], Compound K [[(4-Hydroxy-7-phenoxy-isoquinoline-3-carbonyl)-amino]-acetic acid], Compound L [(S)-2-[(4-Hydroxy-7-phenylsulfanyl-isoquinoline-3-carbonyl)-amino]-propionic acid], Compound M [[(4-Hydroxy-1,7-diphenoxy-isoquinoline-3-carbonyl)-amino]-acetic acid], and Compound N [(4-hydroxy-7-phenylsulfanyl-isoquinoline-3-carbonyl)-amino]-acetic acid.

Pharmaceutical compositions or medicaments effective for treating or preventing chemotherapy induced anemia in a subject who is undergoing, has undergone, or is expected to undergo chemotherapy treatment, wherein the subject is refractory or is at risk for being refractory to recombinant human EPO therapy, are provided herein. In various embodiments, the compositions comprise an effective amount of an agent that inhibits HIF hydroyxlase activity and a carrier.

In various embodiments of the present methods, the agent is administered orally, systemically, by injection, and intravenously.

DESCRIPTION OF THE INVENTION

Figure 1A:
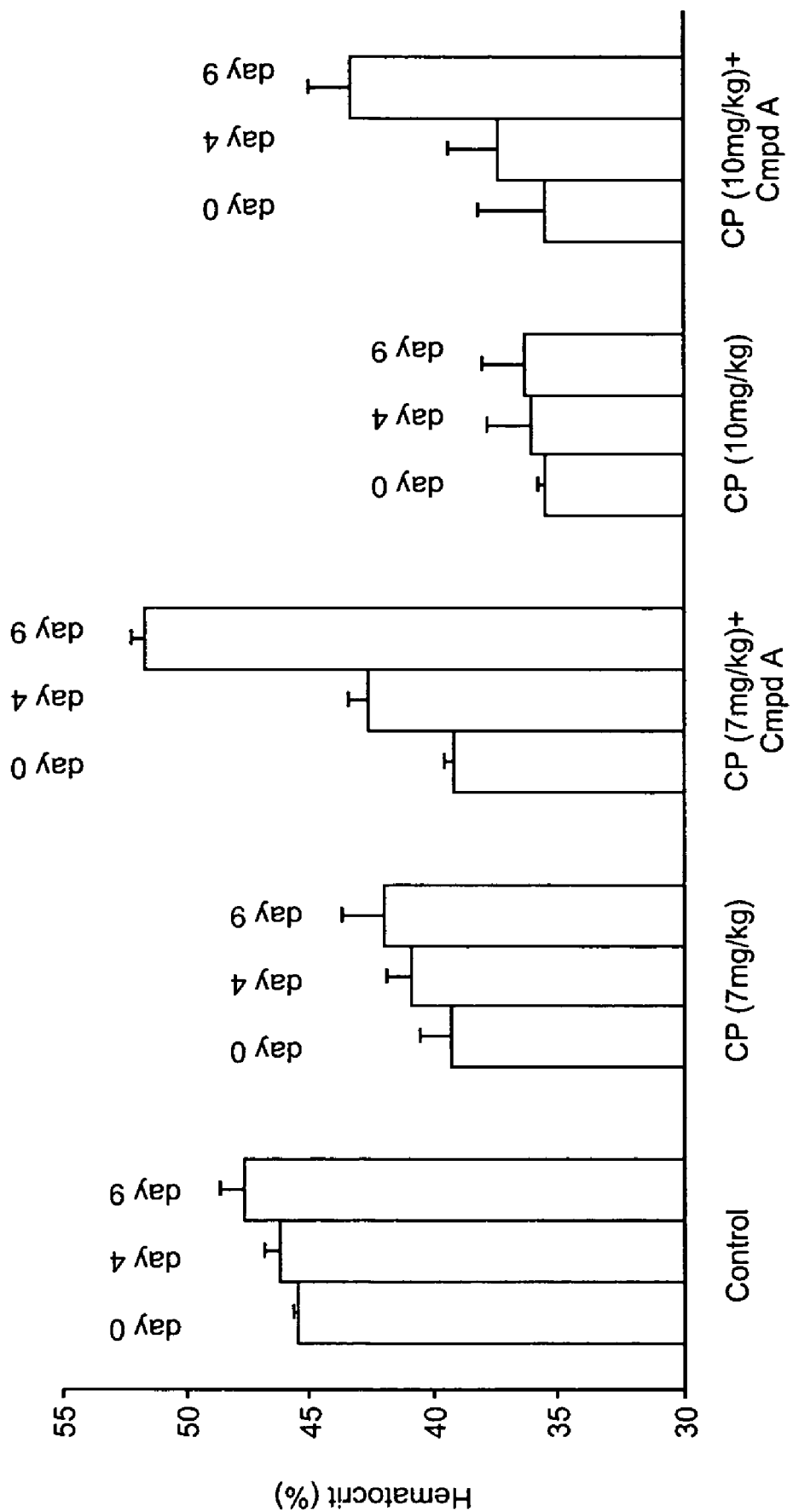
FIG. 1A and FIG. 1B set forth data showing methods and compounds of the present invention increased hematocrit and increased percent circulating reticulocytes in an animal model of chemotherapy-induced anemia, respectively.

Before the present compositions and methods are described, it is to be understood that the invention is not limited to the particular methodologies, protocols, cell lines, assays, and reagents described, as these may vary. It is also to be understood that the terminology used herein is intended to describe particular embodiments of the present invention, and is in no way intended to limit the scope of the present invention as set forth in the appended claims.

It must be noted that as used herein and in the appended claims, the singular forms "a," "an," and "the" include plural references unless context clearly dictates otherwise. Thus, for example, a reference to "a fragment" includes a plurality of such fragments; a reference to an "antibody" is a reference to one or more antibodies and to equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications cited herein are incorporated herein by reference in their entirety for the purpose of describing and disclosing the methodologies, reagents, and tools reported in the publications that might be used in connection with the invention. Nothing herein is to be construed as an admission that the invention is not entitled to antedate such disclosure by virtue of prior invention.

The practice of the present invention will employ, unless otherwise indicated, conventional methods of chemistry, biochemistry, molecular biology, cell biology, genetics, immunology and pharmacology, within the skill of the art. Such techniques are explained fully in the literature. See, e.g., Gennaro, A. R., ed. (1990) *Remington's Pharmaceutical Sciences*, 18$^{th}$ ed., Mack Publishing Co.; Hardman, J. G., Limbird, L. E., and Gilman, A. G., eds. (2001) *The Pharmacological Basis of Therapeutics*, 10$^{th}$ ed., McGraw-Hill Co.; Colowick, S. et al., eds., *Methods In Enzymology*, Academic Press, Inc.; Weir, D. M., and Blackwell, C. C., eds. (1986) *Handbook of Experimental Immunology*, Vols. I-IV, Blackwell Scientific Publications; Maniatis, T. et al., eds. (1989) *Molecular Cloning: A Laboratory Manual*, 2$^{nd}$ edition, Vols. I-III, Cold Spring Harbor Laboratory Press; Ausubel, F. M. et al., eds. (1999) *Short Protocols in Molecular Biology*, 4$^{th}$ edition, John Wiley & Sons; Ream et al., eds. (1998) *Molecular Biology Techniques: An Intensive Laboratory Course*, Academic Press; Newton, C. R., and Graham, A., eds. (1997) *PCR* (Introduction to Biotechniques Series), 2$^{nd}$ ed., Springer Verlag.

Invention

The present invention relates to the discovery that administration of an agent that inhibits HIF hydroxylase activity is therapeutically effective in treating chemotherapy-induced anemia in subjects who have or who are at risk for having chemotherapy-induced anemia, wherein such subjects are refractory to or are at risk for being refractory to treatment with recombinant human EPO.

Therefore, the present invention provides methods for treating or preventing chemotherapy-induced anemia in a subject in need. In various embodiments, the methods comprise treating or preventing chemotherapy-induced anemia in a subject, the method comprising administering to the patient an effective amount of an agent that inhibits HIF hydroxylase activity.

For purposes of this invention, a subject in need is a patient who has or who is at risk for having chemotherapy-induced anemia. In various aspects, a subject particularly suitable for treatment using the present methods and compounds is a subject who is undergoing, has undergone, or will undergo chemotherapy.

In the context of cancer, chemotherapy refers to the use of various cytotoxic agents to treat cancer. It is specifically contemplated that the present methods and compounds are used to treat chemotherapy-induced anemia, e.g., anemia that develops in associated with a chemotherapy regimen, in a subject who is undergoing treatment with any chemotherapeutic agent, or subjects who have undergone or who are expected to undergo such treatment.

Therefore, in one embodiment, the present invention provides a method for treating or preventing anemia of cancer in a subject having or at risk for having such a disease, wherein the subject is refractory to or is at risk for being refractory to recombinant human EPO therapy, and further wherein the subject is undergoing treatment with one or more chemotherapeutics. The treatment with the one or more chemotherapeutics may involve administration of the chemotherapeutic agents that is simultaneous, separate, or sequential to administration of the agent that inhibits HIF hydroyxlase activity.

Suitable chemotherapeutics will be well known to the skilled person in the art. Non-limiting examples of such chemotherapeutic agents include, for example, the chemotherapeutics may be selected from the group consisting of alkylating agents; nitrosoureas; antimetabolites; anthracyclines and related drugs; topoisomerase II inhibitors; mitotic inhibitors and corticosteroid hormones. Known alkylating agents include busulfan, cisplatin, carboplatin, chlorambucil, cyclophosphamide, ifosfamide, dacarbazine (DTIC), mechlorethamine (nitrogen mustard), melphalan and temozolomide. Known nitrosoureas include carmustine (BCNU) and lomustine (CCNU). Known antimetabolites include 5-fluorouracil, capecitabine, 6-mercaptopurine, methotrexate, gemcitabine, cytarabine (ara-C), fludarabine and pemetrexed. Known anthracyclines and related drugs include daunorubicin, doxorubicin (Adriamycin), epirubicin, idarubicin and mitoxantrone. Known topoisomerase II inhibitors include topotecan, irinotecan, etoposide (VP-16) and teniposide. Known mitotic inhibitors include taxanes (paclitaxel, docetaxel) and the vinca alkaloids (vinblastine, vincristine and vinorelbine). Known corticosteroid hormones include prednisone and dexamethasone.

The chemotherapeutics may also be selected from other known chemotherapeutics, e.g. L-asparaginase, dactinomycin, thalidomide, tretinoin, imatinib (Gleevec), gefitinib (Iressa), erlotinib (Tarceva), rituximab (Rituxan), bevacizumab (Avastin), anti-estrogens (tamoxifen, fulvestrant), aromatase inhibitors (anastrozole, exemestane, letrozole), progestins (megestrol acetate), anti-androgens (bicalutamide, flutamide) and LHRH agonists (leuprolide, goserelin).

It is particularly contemplated that the chemotherapeutic agent can be, for example, a microtubule poison, a DNA alkylating agent, etc. Suitable microtubule poisons include, but are not limited to, paclitaxel. Suitable DNA alkylating agents include, e.g., carboplatin, etc.

A subject suitable for treatment with the present methods and compounds is a subject who is refractory to or is at risk for being refractory to recombinant human EPO therapy. Whether or not a subject is refractory to recombinant human EPO therapy can be determined by an assessment of the subject's response or predicted response to treatment with recombinant human EPO. For example, in one particular embodiment, the response desired upon treatment with recombinant human EPO can be defined as an increase in hemoglobin of at least 2 g/dl over a twelve (12) week dosing regimen. If a subject does not display such a response within the required period of time, that subject is deemed refractory to treatment with recombinant human EPO. (See, e.g., Ludwig et al. (1994) Blood 84:1056-1063.)

The value of the desired increase in hemoglobin, used to determine whether or not a particular subject is refractory to EPO treatment, may vary depending on a number of factors, including age and gender. Various factors, including hemoglobin or Hb concentration, serum EPO levels, and hematocrit, can be used singly or in combination to assess whether a particular subject is refractory to or at risk for being refractory to recombinant human EPO therapy.

Thus, in various embodiments of the present invention, a subject can be a subject refractory to treatment with recombinant human EPO if treatment with recombinant human EPO according to a specific dosing regimen fails to increase the subject's hemoglobin level by at least 0.1-5.0 g/dL. In some embodiments, a subject is refractory to treatment with recombinant human EPO if such treatment fails to increase the subject's hemoglobin level by an amount of at least 0.2-5.0, 0.5-5.0, 1.0-5.0, 1.5-5.0, 2.0-5.0, 3.0-5.0 or 4.0-5.0 g/dL. According to further embodiments, the subject is a subject refractory to therapy using recombinant human EPO therapy if such therapy fails to increase the subject's hemoglobin level by an amount of at least 0.2-2.5, 0.4-2.5, 0.6-2.5, 0.8-2.5, 1.0-2.5, 1.2-2.5, 1.4-2.5, 1.6-2.5, 1.8-2.5, or 2-2.5 g/dL, respectively. Finally, in certain embodiments, the subject is a subject refractory to recombinant human EPO therapy if such therapy fails to raise the subject's hemoglobin to at least desired levels of at least 1.0-2.0, 1.1-2.0, 1.2-2.0, 1.3-2.0, 1.4-2.0, 1.5-2.0, 1.6-2.0, 1.7-2.0, 1.8-2.0, or 1.9-2.0 g/dL, respectively.

Other parameters can be used to determine whether a particular subject is refractory to recombinant human EPO therapy. For example, current guidelines relating to recombinant human EPO administration define target hemoglobin levels for an adult subject as 12 gm/dL. Therefore, in one embodiment, a subject is a subject refractory to recombinant human EPO therapy if treatment with acceptable doses over specific period of time fail to increase hemoglobin to at least 12 gm/dL. In other embodiments, a subject is a subject refractory to recombinant human EPO therapy if treatment with acceptable doses over specific period of time fail to increase hemoglobin to at least 10 gm/dL, or at least 11 gm/dL.

Similarly, current guidelines for recombinant human EPO administration define a target hematocrit level for an adult subject as a hematocrit of 36%. Thus, it is contemplated that, in certain embodiments, a subject is refractory to treatment with recombinant human EPO if dosing with recombinant human EPO fails, over a specified period of time, to raise the subject's hematocrit level to at least 36%. In various embodiments, the subject is refractory to treatment with recombinant human EPO if a recombinant human EPO dosing regimen fails to raise the subject's hematocrit to at least 30%, at least 33%, at least 36%, at least 39%, and at least 42%, respectively.

It is noted that various factors, including hemoglobin or Hb concentration, hematocrit, reticolycte or RBC count, serum ferritin levels, and serum EPO levels can be measured by any of the methods available in the art and can be used singly or in combination to determine whether a particular subject is refractory, or may be refractory, to treatment with recombinant EPO. For example, in one embodiment, it is contemplated that serum EPO levels and Hb concentration are used in combination to identify subjects suitable for treatment with the present methods and compounds. In a specific embodiment, the subject is a refractory subject suitable for treatment using the present methods if, after two weeks of therapy, the subject has a serum EPO level of or less than 100 mU/mL, and has demonstrated an increase in hemoglobin of less than 0.5 g/dL. In another aspect, the subject is a subject refractory to recombinant human EPO therapy if, after two weeks of recombinant human EPO therapy, a high serum ferritin level, for example, a serum ferritin level of greater than or equal to 400 ng/ml.

In particular, it is demonstrated herein that HIF hydroxylase inhibitors effectively treated chemotherapy-induced anemia in animal models of chemotherapy-induced anemia. (See, e.g., Examples 1, 2, and 3.)

The present invention demonstrates that methods and compounds of the invention are effective in treating or preventing the development of chemotherapy-induced anemia. Additionally, the present invention demonstrates that methods and compounds of the invention are useful for limiting weight loss associated with chemotherapy.

Methods

Various methods are provided herein. In one aspect, the methods comprise administering to a subject an agent that inhibits HIF hydoxylase activity. HIF hydroxylase activity can include, e.g., the activity of any enzyme selected from the group consisting of HIF prolyl hydroxylase, HIF asparaginyl hydroxylase, and HIF lysyl hydroxylase. In preferred embodiments, the enzyme is a HIF prolyl hydroxylase enzyme, e.g., EGLN-1, EGLN-2, EGLN-3, etc. (See, e.g., Taylor (2001) Gene 275:125-132; Epstein et al. (2001) Cell 107:43-54; and Bruick and McKnight (2001) Science 294: 1337-1340.)

A HIF hydroxylase is any enzyme capable of hydroyxlating a residue in the HIF protein. HIF hydroxylases include HIF prolyl hydroxylases. In certain embodiments, the residue hydroxylated by HIF prolyl hydroxylase includes the proline found within the motif LXXLAP, e.g., as occurs in the human HIF-1α native sequence at $L_{397}$TLLAP and $L_{559}$EMLAP. HIF prolyl hydroxylase includes members of the Egl-Nine (EGLN) gene family described by Taylor (2001, Gene 275: 125-132), and characterized by Aravind and Koonin (2001, Genome Biol 2:RESEARCH0007), Epstein et al. (2001, Cell 107:43-54), and Bruick and McKnight (2001, Science 294: 1337-1340). Examples of HIF prolyl hydroxylase enzymes include human SM-20 (EGLN1) (GenBank Accession No. AAG33965; Dupuy et al. (2000) Genomics 69:348-54), EGLN2 isoform 1 (GenBank Accession No. CAC42510; Taylor, supra), EGLN2 isoform 2 (GenBank Accession No. NP_060025), and EGLN3 (GenBank Accession No. CAC42511; Taylor, supra); mouse EGLN1 (GenBank Accession No. CAC42515), EGLN2 (GenBank Accession No. CAC42511), and EGLN3 (SM-20) (GenBank Accession No. CAC42517); and rat SM-20 (GenBank Accession No. AAA 19321). Additionally, HIF prolyl hydroxylase may include *Caenorhabditis elegans* EGL-9 (GenBank Accession No. AAD56365) and *Drosophila melanogaster* CG1114 gene product (GenBank Accession No. AAF52050). HIF prolyl hydroxylase also includes any fragment of the foregoing full-length proteins that retain at least one structural or functional characteristic.

An agent that inhibits HIF hydroxylase activity is any agent that reduces or otherwise modulates the activity of a HIF hydroxylase enzyme. In particular embodiments of the present invention, the agent that inhibits HIF hydroxylase activity is a structural mimetics of 2-oxoglutarate. Such compounds may inhibit the target 2-oxoglutarate dioxygenase enzyme family member competitively with respect to 2-oxoglutarate. (Majamaa et al. (1984) Eur J Biochem 138:239-245; and Majamaa et al. (1985) Biochem J 229:127-133.) Hydroxylase inhibitors specifically contemplated for use in the present methods are described, e.g., in Majamaa et al., supra; Kivirikko and Myllyhaiju (1998) Matrix Biol 16:357-368; Bickel et al. (1998) Hepatology 28:404-411; Friedman et al. (2000) Proc Natl Acad Sci USA 97:4736-4741; Franklin (1991) Biochem Soc Trans 19):812 815; Franklin et al. (2001) Biochem J 353:333-338; and International Publication Nos. WO 03/053977 and WO 03/049686, each incorporated by reference herein in its entirety. Exemplary HIF prolyl hydroxylase inhibitors, including Compound A [(1 Chloro-4-hydroxy-isoquinoline-3-carbonyl)-amino]-acetic acid]; Compound B [((S)-2-[(4-Hydroxy-7-phenoxy-6,7-dihydro-isoquinoline-3-carbonyl)-amino]-propionic acid]; Compound C [{[4-Hydroxy-7-(4-methoxy-phenoxy)-isoquinoline-3-carbonyl]-amino}-acetic acid]; Compound D [[(4-Hydroxy-1-methyl-7-phenoxy-isoquinoline-3-carbonyl)-amino]-acetic acid]; Compound E [[7-(4-Fluoro-phenoxy)-4-hydroxy-isoquinoline-3-carbonyl]-amino-acetic acid]; Compound F [4-Oxo-1,4-dihydro-[1,10]phenanthroline-3-carboxylic acid], Compound G [3-{[4-(3,3-Dibenzyl-ureido)-benzenesulfonyl]-[2-(4-methoxy-phenyl)-ethyl]-amino}-N-hydroxy-propionamide], Compound H [[(7-Chloro-3-hydroxy-quinoline-2-carbonyl)-amino]-acetic acid], Compound I [[(1-Chloro-4-hydroxy-7-methoxy-isoquinoline-3-carbonyl)-amino]-acetic acid], Compound J [[(6,7-Dichloro-4-hydroxy-isoquinoline-3-carbonyl)-amino]-acetic acid], Compound K [[(4-Hydroxy-7-phenoxy-isoquinoline-3-carbonyl)-amino]-acetic acid], Compound L [(S)-2-[(4-Hydroxy-7-phenylsulfanyl-isoquinoline-3-carbonyl)-amino]-propionic acid], Compound M [[(4-Hydroxy-1,7-diphenoxy-isoquinoline-3-carbonyl)-amino]-acetic acid], and Compound N [(4-hydroxy-7-phenylsulfanyl-isoquinoline-3-carbonyl)-amino]-acetic acid, can be used to demonstrate the methods of the invention described herein.

Compounds

In preferred methods, the present methods comprise administering to a subject an effective amount of a compound that stabilizes HIFα. Exemplary compounds are disclosed in, e.g., International Publication No. WO 03/049686, International Publication No. WO 03/053997, International Publication No. WO 04/108121, and International Publication No. WO 04/108681, each of which is incorporated herein by reference in their entireties.

For example, International Publication No. WO 03/049686, International Publication No. WO 03/053997, International Publication No. WO 04/108121, and International Publication No. WO 04/108681 disclose exemplary compounds according to Formula I, below. These compounds include, but are not limited to, compounds of Formulae Ia, Ib, Ic, and Id. Further exemplary compounds are according to Formula Ie, including, but not limited to, compounds of Formulae Ie(i), Ie(ii), Ie(iii), and Ie(iv), as described below. International Publication No. WO 03/049686 and International Publication No. WO 03/053997 disclose exemplary compounds according to Formula II, below. Exemplary compounds according to Formula III, shown below, are disclosed in International Publication No. WO 03/049686, International Publication No. WO 03/053997, and International Publication No. WO 04/108121. These compounds include, but are not limited to, compounds of Formula IIIa. Further exemplary compounds are according to Formula IV, as described below.

In certain embodiments, a compound of the invention is a compound that inhibits HIF hydroxylase activity. In various embodiments, the activity is due to a HIF prolyl hydroxylase, such as, for example, EGLN1, EGLN2, or EGLN3, etc. In other embodiments, the activity is due to a HIF asparaginyl hydroxylase, such as, for example, including, but not limited to, FIH. A preferred compound of the invention is a compound that inhibits HIF prolyl hydroxylase activity. The inhibition can be direct or indirect, can be competitive or non-competitive, etc.

In one aspect, a compound of the invention is any compound that inhibits or otherwise modulates the activity of a 2-oxoglutarate dioxygenase enzyme. 2-oxoglutarate dioxygenase enzymes include, but are not limited to, hydroxylase enzymes. Hydroxylase enzymes hydroxylate target substrate residues and include, for example, prolyl, lysyl, asparaginyl (asparagyl, aspartyl) hydroxylases, etc. Hydroxylases are sometimes described by target substrate, e.g., HIF hydroxylases, procollagen hydroxylases, etc., and/or by targeted residues within the substrate, e.g., prolyl hydroxylases, lysyl hydroxylases, etc., or by both, e.g., HIF prolyl hydroxylases, procollagen prolyl hydroxylases, etc. Representative 2-oxoglutarate dioxygenase enzymes include, but are not limited to, HIF hydroxylases, including HIF prolyl hydroxylases, e.g., EGLN1, EGLN2, and EGLN3, HIF asparaginyl hydroxylases, e.g., factor inhibiting HIF (FIH), etc.; procollagen hydroxylases, e.g., procollagen lysyl hydroxylases, procollagen prolyl hydroxylases, e.g., procollagen prolyl 3-hydroxylase, procollagen prolyl 4-hydroxylase α(I) and α(II), etc.; thymine 7-hydroxylase; aspartyl (asparaginyl) β-hydroxylase; ε-N-trimethyllysine hydroxylase; γ-butyrobetaine hydroxylase, etc. Although enzymatic activity can include any activity associated with any 2-oxoglutarate dioxygenase, the hydroxylation of amino acid residues within a substrate is specifically contemplated. Although hydroxylation of proline and/or asparagine residues within a substrate is specifically included, hydroxylation of other amino acids is also contemplated.

In one aspect, a compound of the invention that shows inhibitory activity toward one or more 2-oxoglutarate dioxygenase enzyme may also show inhibitory activity toward one or more additional 2-oxoglutarate dioxygenase enzymes, e.g., a compound that inhibits the activity of a HIF hydroxylase may additionally inhibit the activity of a collagen prolyl hydroyxlase, a compound that inhibits the activity of a HIF prolyl hydroylxase may additionally inhibit the activity of a HIF asparaginyl hydroylxase, etc.

In some aspects, compounds of the present invention include, for example, structural mimetics of 2-oxoglutarate. Such compounds may inhibit the target 2-oxoglutarate dioxygenase enzyme family member competitively with respect to 2-oxoglutarate and noncompetitively with respect to iron. (Majamaa et al. (1984) Eur J Biochem 138:239-245; and Majamaa et al. Biochem J 229:127-133.)

In certain embodiments, a compound of the present invention is a compound of Formula I. In particular embodiments, the 2-oxoglutarate mimetic is a pyridine-2-carboxamide including, but not limited to, compounds of Formula I. In particular embodiments, the 2-oxoglutarate mimetic is a quinoline-2-carboxamide including, but not limited to, compounds of Formula Ia. In other embodiments, the 2-oxoglutarate mimetic is an isoquinoline-3-carboxamide including, but not limited to, compounds of Formula Ib. In additional embodiments, the 2-oxoglutarate mimetic is a cinnoline-3-carboxamide including, but not limited to, compounds of Formula Ic, or is a beta-carboline-3-carboxamide including, but not limited to, compounds of Formula Id.

As stated above, in certain embodiments, a compounds of the present invention is a compound of Formula I

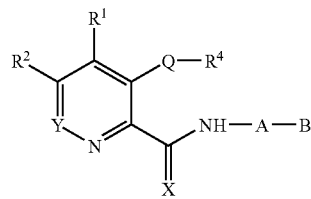
(I)

wherein

A is 1,2-arylidene, 1,3-arylidene, 1,4-arylidene; or ($C_1$-$C_4$)-alkylene, optionally substituted by one or two halogen, cyano, nitro, trifluoromethyl, ($C_1$-$C_6$)-alkyl, ($C_1$-$C_6$)-hydroxyalkyl, ($C_1$-$C_6$)-alkoxy, —O—[$CH_2$]$_x$—$C_fH_{(2f+1-g)}$Hal$_g$, ($C_1$-$C_6$)-fluoroalkoxy, ($C_1$-$C_8$)-fluoroalkenyloxy, ($C_1$-$C_8$)-fluoroalkynyloxy, —OCF$_2$Cl, —O—CF$_2$—CHFCl; ($C_1$-$C_6$)-alkylmercapto, ($C_1$-$C_6$)-alkylsulfinyl, ($C_1$-$C_6$)-alkylsulfonyl, ($C_1$-$C_6$)-alkylcarbonyl, ($C_1$-$C_6$)-alkoxycarbonyl, carbamoyl, N—($C_1$-$C_4$)-alkylcarbamoyl, N,N-di-($C_1$-$C_4$)-alkylcarbamoyl, ($C_1$-$C_6$)-alkylcarbonyloxy, ($C_3$-$C_8$)-cycloalkyl, phenyl, benzyl, phenoxy, benzyloxy, anilino, N-methylanilino, phenylmercapto, phenylsulfonyl, phenylsulfinyl, sulfamoyl, N—($C_1$-$C_4$)-alkylsulfamoyl, N,N-di-($C_1$-$C_4$)-alkylsulfamoyl; or by a substituted ($C_6$-$C_{12}$)-aryloxy, ($C_7$-$C_{11}$)-aralkyloxy, ($C_6$-$C_{12}$)-aryl, ($C_7$-$C_{11}$)-aralkyl radical, which carries in the aryl moiety one to five identical or different substituents selected from halogen, cyano, nitro, trifluoromethyl, ($C_1$-$C_6$)-alkyl, ($C_1$-$C_6$)-alkoxy, —O—[$CH_2$]$_x$—$C_fH_{(2f+1-g)}$Hal$_g$, —OCF$_2$Cl, —O—CF$_2$—CHFCl, ($C_1$-$C_6$)-alkylmercapto, ($C_1$-$C_6$)-alkylsulfinyl, ($C_1$-$C_6$)-alkylsulfonyl, ($C_1$-$C_6$)-alkylcarbonyl, ($C_1$-$C_6$)-alkoxycarbonyl, carbamoyl, N—($C_1$-$C_4$)-alkylcarbamoyl, N,N-di-($C_1$-$C_4$)-alkylcarbamoyl, ($C_1$-$C_6$)-alkylcarbonyloxy, ($C_3$-$C_8$)-cycloalkyl, sulfamoyl, N—($C_1$-$C_4$)-alkylsulfamoyl, N,N-di-($C_1$-$C_4$)-alkylsulfamoyl; or wherein A is —CR$^5$R$^6$ and R$^5$ and R$^6$ are each independently selected from hydrogen, ($C_1$-$C_6$)-alkyl, ($C_3$-$C_7$)-cycloalkyl, aryl, or a substituent of the α-carbon atom of an α-amino acid, wherein the amino acid is a natural L-amino acid or its D-isomer;

B is —CO$_2$H, —NH$_2$, —NHSO$_2$CF$_3$, tetrazolyl, imidazolyl, 3-hydroxyisoxazolyl, —CONHCOR''', —CONHSOR''', CONHSO$_2$R''', where R''' is aryl, heteroaryl, ($C_3$-$C_7$)-cycloalkyl, or ($C_1$-$C_4$)-alkyl, optionally monosubstituted by ($C_6$-$C_{12}$)-aryl, heteroaryl, OH, SH, ($C_1$-$C_4$)-alkyl, ($C_1$-$C_4$)-alkoxy, ($C_1$-$C_4$)-thioalkyl, ($C_1$-$C_4$)-sulfinyl, ($C_1$-$C_4$)-sulfonyl, CF$_3$, Cl, Br, F, I, NO2, —COOH, ($C_2$-$C_5$)-alkoxycarbonyl, NH$_2$, mono-($C_1$-$C_4$-alkyl)-amino, di-($C_1$-$C_4$-alkyl)-amino, or ($C_1$-$C_4$)-perfluoroalkyl;

or wherein B is a CO$_2$-G carboxyl radical, where G is a radical of an alcohol G-OH in which G is selected from ($C_1$-$C_{20}$)-alkyl radical, ($C_3$-$C_8$) cycloalkyl radical, ($C_2$-$C_{20}$)-alkenyl radical, ($C_3$-$C_8$)-cycloalkenyl radical, retinyl radical, ($C_2$-$C_{20}$)-alkynyl radical, ($C_4$-$C_{20}$)-alkenynyl radical, where the alkenyl, cycloalkenyl, alkynyl, and alkenynyl radicals contain one or more multiple bonds; ($C_6$-$C_{16}$)-carbocyclic aryl radical, ($C_7$-$C_{16}$)-carbocyclic aralkyl radical, heteroaryl radical, or heteroaralkyl radical, wherein a heteroaryl radical or heteroaryl moiety of a heteroaralkyl radical contains 5 or 6 ring atoms; and wherein radicals defined for G are substituted by one or more hydroxyl, halogen, cyano, trifluoromethyl, nitro, carboxyl, ($C_1$-$C_{12}$)-alkyl, ($C_3$-$C_8$)-cycloalkyl, ($C_5$-$C_8$)-cycloalkenyl, ($C_6$-$C_{12}$)-aryl, ($C_7$-$C_{16}$)-aralkyl, ($C_2$-$C_{12}$)-alkenyl, ($C_2$-$C_{12}$)-alkynyl, ($C_1$-$C_{12}$)-alkoxy, ($C_1$-$C_{12}$)-alkoxy-($C_1$-$C_{12}$)-alkyl, ($C_1$-$C_{12}$)-alkoxy-($C_1$-$C_{12}$)-alkoxy, ($C_6$-$C_{12}$)-aryloxy, ($C_7$-$C_{16}$)-aralkyloxy, ($C_1$-$C_8$)-hydroxyalkyl, —O—[$CH_2$]$_x$—$C_fH_{(2f+1-g)}$—F$_g$, —OCF$_2$Cl, —OCF$_2$—CHFCl, ($C_1$-$C_{12}$)-alkylcarbonyl, ($C_3$-$C_8$)-cycloalkylcarbonyl, ($C_6$-$C_{12}$)-arylcarbonyl, ($C_7$-$C_{16}$)-aralkylcarbonyl, cinnamoyl, ($C_2$-$C_{12}$)-alkenylcarbonyl, ($C_2$-$C_{12}$)-alkynylcarbonyl, ($C_1$-$C_{12}$)-alkoxycarbonyl, ($C_1$-$C_{12}$)-alkoxy-($C_1$-$C_{12}$)-alkoxycarbonyl, ($C_6$-$C_{12}$)-aryloxycarbonyl, ($C_7$-$C_{16}$)-aralkoxycarbonyl, ($C_3$-$C_8$)-cycloalkoxycarbonyl, ($C_2$-$C_{12}$)-alkenyloxycarbonyl, ($C_2$-$C_{12}$)-alkynyloxycarbonyl, acyloxy, ($C_1$-$C_{12}$)-alkoxycarbonyloxy, ($C_1$-$C_{12}$)-alkoxy-($C_1$-$C_{12}$)-alkoxycarbonyloxy, ($C_6$-$C_{12}$)-aryloxycarbonyloxy, ($C_7$-$C_{16}$) aralkyloxycarbonyloxy, ($C_3$-$C_8$)-cycloalkoxycarbonyloxy, ($C_2$-$C_{12}$)-alkenyloxycarbonyloxy, ($C_2$-$C_{12}$)-alkynyloxycarbonyloxy, carbamoyl, N—($C_1$-$C_{12}$)-alkylcarbamoyl, N,N-di($C_1$-$C_{12}$)-alkylcarbamoyl, N—($C_3$-$C_8$)-cycloalkyl-carbamoyl, N—($C_6$-$C_{16}$)-arylcarbamoyl, N—($C_7$-$C_{16}$)-aralkylcarbamoyl, N—($C_1$-$C_{10}$)-alkyl-N—($C_6$-$C_{16}$)-arylcarbamoyl, N—($C_1$, $C_{10}$)-alkyl-N—($C_7$-$C_{16}$)-aralkylcarbamoyl, N—(($C_1$-$C_{10}$)-alkoxy-($C_1$-$C_{10}$)-alkyl)-carbamoyl, N—(($C_6$-$C_{12}$)-aryloxy-($C_1$-$C_{10}$)alkyl)-carbamoyl, N—(($C_7$-$C_{16}$)-aralkyloxy-($C_1$-$C_{10}$)-alkyl)-carbamoyl, N—($C_1$, $C_{10}$)-alkyl-N—(($C_1$-$C_{10}$)-alkoxy-($C_1$-$C_{10}$)-alkyl)-carbamoyl, N—($C_7$, $C_{16}$)-alkyl-N—(($C_6$-$C_{16}$)-aryloxy-($C_1$-$C_{10}$)-alkyl)-carbamoyl, N—($C_1$, $C_{10}$)-alkyl-N—(($C_7$-$C_{16}$)-aralkyloxy-($C_1$-$C_{10}$)-alkyl)-carbamoyl, carbamoyloxy, N—($C_1$-$C_{12}$)-alkylcarbamoyloxy, N,N-di-($C_1$-$C_{12}$)-alkylcarbamoyloxy, N—($C_3$-$C_8$)-cycloalkylcarbamoyloxy, N—($C_6$-$C_{12}$)-arylcarbamoyloxy, N—($C_7$-$C_{16}$)-aralkylcarbamoyloxy, N—($C_1$-$C_{10}$)-alkyl-N—($C_6$-$C_{12}$)-arylcarbamoyloxy, N($C_1$-$C_{10}$)-alkyl-N—($C_7$-$C_{16}$)-aralkylcarbamoyloxy, N—(($C_1$-$C_{10}$)-alkyl)-carbamoyloxy, N—(($C_6$-$C_{12}$)-aryloxy-($C_1$-$C_{10}$)-alkyl)-carbamoyloxy, N—(($C_7$-$C_{16}$)-aralkyloxy-($C_1$-$C_{10}$)-alkyl)-carbamoyloxy, N—($C_1$-$C_{10}$)-alkyl-N—(($C_1$-$C_{10}$)-alkoxy-($C_1$-$C_{10}$)-alkyl)-carbamoyloxy, N—($C_1$-$C_{10}$)-alkyl-N—(($C_6$-$C_{12}$)-aryloxy-($C_1$-$C_{10}$)-alkyl)-carbamoyloxy, N—($C_1$-$C_{10}$)-alkyl-N—(($C_7$-$C_{16}$)- aralkyloxy-$(C_1$-$C_{10})$-alkyl)-carbamoyloxy, amino, $(C_1$-$C_{12})$-alkylamino, di-$(C_1$-$C_{12})$-alkylamino, $(C_3$-$C_8)$-cycloalkylamino, $(C_6$-$C_{12})$-alkenylamino, $(C_2$-$C_{12})$-alkynylamino, N—$(C_6$-$C_{12})$-arylamino, N—$(C_7$-$C_{11})$-aralkylamino, N-alkyl-aralkylamino, N-alkyl-arylamino, $(C_1$-$C_{12})$-alkoxyamino, $(C_1$-$C_{12})$-alkoxy-N—$(C_1$-$C_{10})$-alkylamino, $(C_1$-$C_{12})$-alkylcarbonylamino, $(C_3$-$C_8)$-cycloalkylcarbonylamino, $(C_6$-$C_{12})$ arylcarbonylamino, $(C_7$-$C_{16})$-aralkylcarbonylamino, $(C_1$-$C_{12})$-alkylcarbonyl-N—$(C_1$-$C_{10})$-alkylamino, $(C_3$-$C_8)$-cycloalkylcarbonyl-N—$(C_1$-$C_{10})$-alkylamino, $(C_6$-$C_{12})$-arylcarbonyl-N—$(C_1$-$C_{10})$alkylamino, $(C_7$-$C_{11})$-aralkylcarbonyl-N—$(C_1$-$C_{10})$-alkylamino, $(C_1$-$C_{12})$-alkylcarbonylamino-$(C_1$-$C_8)$-alkyl, $(C_3$-$C_8)$-cycloalkylcarbonylamino-$(C_1$-$C_8)$alkyl, $(C_6$-$C_{12})$-arylcarbonylamino-$(C_1$-$C_8)$-alkyl, $(C_7$-$C_{12})$-aralkylcarbonylamino$(C_1$-$C_8)$-alkyl, amino-$(C_1$-$C_{10})$-alkyl, N—$(C_1$-$C_{10})$ alkylamino-$(C_1$-$C_{10})$-alkyl, N.N-di-$(C_1$-$C_{10})$-alkylamino-$(C_1$-$C_{10})$-alkyl, $(C_3$-$C_8)$ cycloalkylamino-$(C_1$-$C_{10})$-alkyl, $(C_1$-$C_{12})$-alkylmercapto, $(C_1$-$C_{12})$-alkylsulfinyl, $(C_1$-$C_{12})$-alkylsulfonyl, $(C_6$-$C_{16})$-arylmercapto, $(C_6$-$C_{16})$-arylsulfinyl, $(C_6$-$C_{12})$-arylsulfonyl, $(C_7$-$C_{16})$-aralkylmercapto, $(C_7$-$C_{16})$-aralkylsulfinyl, $(C_7$-$C_{16})$-aralkylsulfonyl, sulfamoyl, N—$(C_1$-$C_{10})$-alkylsulfamoyl, N.N-di$(C_1$-$C_{10})$-alkylsulfamoyl, $(C_3$-$C_8)$-cycloalkylsulfamoyl, N—$(C_6$-$C_{12})$-alkylsulfamoyl, N—$(C_7$-$C_{16})$-aralkylsulfamoyl, N—$(C_1$-$C_{10})$-alkyl-N—$(C_6$-$C_{12})$-arylsulfamoyl, N—$(C_1$-$C_{10})$-alkyl-N—$(C_7$-$C_{16})$-aralkylsulfamoyl, $(C_1$-$C_{10})$-alkylsulfonamido, N—$((C_1$-$C_{10})$-alkyl)-$(C_1$-$C_{10})$-alkylsulfonamido, $(C_7$-$C_{16})$-aralkylsulfonamido, or N—$((C_1$-$C_{10})$-alkyl-$(C_7$-$C_{16})$-aralkylsulfonamido; wherein radicals which are aryl or contain an aryl moiety, may be substituted on the aryl by one to five identical or different hydroxyl, halogen, cyano, trifluoromethyl, nitro, carboxyl, $(C_1$-$C_{12})$-alkyl, $(C_3$-$C_8)$-cycloalkyl, $(C_6$-$C_{12})$-aryl, $(C_7$-$C_{16})$-aralkyl, $(C_1$-$C_{12})$-alkoxy, $(C_1$-$C_{12})$-alkoxy-$(C_1$-$C_{12})$alkyl, $(C_1$-$C_{12})$-alkoxy-$(C_{10}$-$C_{12})$ alkoxy, $(C_6$-$C_{12})$-aryloxy, $(C_7$-$C_{16})$-aralkyloxy, $(C_1$-$C_8)$-hydroxyalkyl, $(C_1$-$C_{12})$-alkylcarbonyl, $(C_3$-$C_8)$-cycloalkyl-carbonyl, $(C_6$-$C_{12})$-arylcarbonyl, $(C_7$-$C_{16})$ aralkylcarbonyl, $(C_1$-$C_{12})$-alkoxycarbonyl, $(C_1$-$C_{12})$-alkoxy-$(C_1$-$C_{12})$-alkoxycarbonyl, $(C_6$-$C_{12})$-aryloxycarbonyl, $(C_7$-$C_{16})$-aralkoxycarbonyl, $(C_3$-$C_8)$-cycloalkoxycarbonyl, $(C_2$-$C_{12})$-alkenyloxycarbonyl, $(C_2$-$C_{12})$-alkynyloxycarbonyl, $(C_1$-$C_{12})$-alkylcarbonyloxy, $(C_3$-$C_8)$-cycloalkylcarbonyloxy, $(C_6$-$C_{12})$-arylcarbonyloxy, $(C_7$-$C_{16})$-aralkylcarbonyloxy, cinnamoyloxy, $(C_2$-$C_{12})$-alkenylcarbonyloxy, $(C_2$-$C_{12})$-alkynylcarbonyloxy, $(C_1$-$C_{12})$-alkoxycarbonyloxy, $(C_1$-$C_{12})$-alkoxy-$(C_1$-$C_{12})$-alkoxycarbonyloxy, $(C_6$-$C_{12})$-aryloxycarbonyloxy, $(C_7$-$C_{16})$-aralkyloxycarbonyloxy, $(C_3$-$C_8)$-cycloalkoxycarbonyloxy, $(C_2$-$C_{12})$-alkenyloxycarbonyloxy, $(C_2$-$C_{12})$-alkynyloxycarbonyloxy, carbamoyl, N—$(C_1$-$C_{12})$-alkylcarbamoyl, N.N-di-$(C_1$-$C_{12})$-alkylcarbamoyl, N—$(C_3$-$C_8)$-cycloalkylcarbamoyl, N—$(C_6$-$C_{12})$-arylcarbamoyl, N—$(C_7$-$C_{16})$-aralkylcarbamoyl, N—$(C_1$-$C_{10})$-alkyl-N—$(C_6$-$C_{12})$-arylcarbamoyl, N—$(C_1$-$C_{10})$-alkyl-N—$(C_7$-$C_{16})$-aralkylcarbamoyl, N—$((C_1$-$C_{10})$-alkoxy-$(C_1$-$C_{10})$-alkyl)-carbamoyl, N—$((C_6$-$C_{12})$-aryloxy-$(C_1$-$C_{10})$-alkyl)-carbamoyl, N—$((C_7$-$C_{16})$-aralkyloxy-$(C_1$-$C_{10})$-alkyl)-carbamoyl, N—$(C_1$-$C_{10})$-alkyl-N—$((C_1$-$C_{10})$-alkoxy-$(C_1$-$C_{10})$-alkyl)-carbamoyl, N—$(C_1$-$C_{10})$-alkyl-N—$((C_6$-$C_{12})$-aryloxy-$(C_1$-$C_{10})$-alkyl)-carbamoyl, N—$(C_1$-$C_{10})$-alkyl-N—$((C_7$-$C_{16})$-aralkyloxy-$(C_1$-$C_{10})$-alkyl)-carbamoyl, carbamoyloxy, N—$(C_1$-$C_{12})$-alkylcarbamoyloxy, N.N-di-$(C_1$-$C_{12})$-alkylcarbamoyloxy, N—$(C_3$-$C_8)$-cycloalkylcarbamoyloxy, N—$(C_6$-$C_{12})$-arylcarbamoyloxy, N—$(C_7$-$C_{16})$-aralkylcarbamoyloxy, N—$(C_1$-$C_{10})$-alkyl-N—$(C_6$-$C_{12})$-arylcarbamoyloxy, N$(C_1$-$C_{10})$-alkyl-N—$(C_7$-$C_{16})$-aralkylcarbamoyloxy, N—$((C_1$-$C_{10})$-alkyl)-carbamoyloxy, N—$((C_6$-$C_{12})$-aryloxy-$(C_1$-$C_{10})$-alkyl)-carbamoyloxy, N—$((C_7$-$C_{16})$-aralkyloxy-$(C_1$-$C_{10})$-alkyl)-carbamoyloxy, N—$(C_1$-$C_{10})$-alkyl-N—$((C_1$-$C_{10})$-alkoxy-$(C_1$-$C_{10})$-alkyl)-carbamoyloxy, N—$(C_1$-$C_{10})$-alkyl-N—$((C_6$-$C_{12})$-aryloxy-$(C_1$-$C_{10})$-alkyl)-carbamoyloxy, N—$(C_1$-$C_{10})$-alkyl-N—$((C_7$-$C_{16})$-aralkyloxy-$(C_1$-$C_{10})$-alkyl)-carbamoyloxy, amino, $(C_1$-$C_{12})$-alkylamino, di-$(C_1$-$C_{12})$-alkylamino, $(C_3$-$C_8)$-cycloalkylamino, $(C_3$-$C_{12})$-alkenylamino, $(C_3$-$C_{12})$-alkynylamino, N—$(C_6$-$C_{12})$-arylamino, N—$(C_7$-$C_{11})$-aralkylamino, N-alkylaralkylamino, N-alkyl-arylamino, $(C_1$-$C_{12})$-alkoxyamino, $(C_1$-$C_{12})$-alkoxy-N—$(C_1$-$C_{10})$-alkylamino, $(C_1$-$C_{12})$-alkylcarbonylamino, $(C_3$-$C_8)$-cycloalkylcarbonylamino, $(C_6$-$C_{12})$-arylcarbonylamino, $(C_7$-$C_{16})$-alkylcarbonylamino, $(C_1$-$C_{12})$-alkylcarbonyl-N—$(C_1$-$C_{10})$-alkylamino, $(C_3$-$C_8)$-cycloalkylcarbonyl-N—$(C_1$-$C_{10})$-alkylamino, $(C_6$-$C_{12})$-arylcarbonyl-N—$(C_1$-$C_{10})$-alkylamino, $(C_7$-$C_{11})$-aralkylcarbonyl-N—$(C_1$-$C_{10})$-alkylamino, $(C_1$-$C_{12})$-alkylcarbonylamino-$(C_1$-$C_8)$-alkyl, $(C_3$-$C_8)$-cycloalkylcarbonylamino-$(C_1$-$C_8)$-alkyl, $(C_6$-$C_{12})$-arylcarbonylamino-$(C_1$-$C_8)$-alkyl, $(C_7$-$C_{16})$-aralkylcarbonylamino-$(C_1$-$C_8)$-alkyl, amino-$(C_1$-$C_{10})$-alkyl, N—$(C_1$-$C_{10})$-alkylamino-$(C_1$-$C_{10})$alkyl, N.N-di-$(C_1$-$C_{10})$-alkylamino-$(C_1$-$C_{10})$-alkyl, $(C_3$-$C_8)$-cycloalkylamino-$(C_1$-$C_{10})$-alkyl, $(C_1$-$C_{12})$-alkylmercapto, $(C_1$-$C_{12})$-alkylsulfinyl, $(C_1$-$C_{12})$-alkylsulfonyl, $(C_6$-$C_{12})$-arylmercapto, $(C_6$-$C_{12})$-arylsulfinyl, $(C_6$-$C_{12})$-arylsulfonyl, $(C_7$-$C_{16})$-aralkylmercapto, $(C_7$-$C_{16})$-aralkylsulfinyl, or $(C_7$-$C_{16})$-aralkylsulfonyl;

X is O or S;

Q is O, S, NR', or a bond;

where, if Q is a bond, $R^4$ is halogen, nitrile, or trifluoromethyl;

or where, if Q is O, S, or NR', $R^4$ is hydrogen, $(C_1$-$C_{10})$-alkyl radical, $(C_2$-$C_{10})$-alkenyl radical, $(C_2$-$C_{10})$-alkynyl radical, wherein alkenyl or alkynyl radical contains one or two C—C multiple bonds; unsubstituted fluoroalkyl radical of the formula —$[CH_2]_x$—$C_fH_{(2f+1-g)}$—$F_g$,$(C_1$-$C_8)$-alkoxy-$(C_1$-$C_6)$-alkyl radical, $(C_1$-$C_6)$-alkoxy-$(C_1$-$C_4)$-alkoxy-$(C_1$-$C_4)$-alkyl radical, aryl radical, heteroaryl radical, $(C_7$-$C_{11})$-aralkyl radical, or a radical of the Formula Z $$—[CH_2]_v—[O]_w—[CH_2]_t\text{-}E \qquad (Z)$$

where

E is a heteroaryl radical, a $(C_3$-$C_8)$-cycloalkyl radical, or a phenyl radical of the Formula F

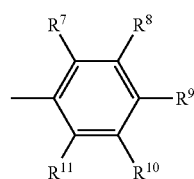

(F)

v is 0-6,
w is 0 or 1,
t is 0-3, and $R^7$, $R^8$, $R^9$, $R^{10}$, and $R^{11}$ are identical or different and are hydrogen, halogen, cyano, nitro, trifluoromethyl, $(C_1-C_6)$-alkyl, $(C_3-C_8)$-cycloalkyl, $(C_1-C_6)$-alkoxy, —O—$[CH_2]_x$—$C_fH_{(2f+1-g)}F_g$, —$OCF_2$—Cl, —O—$CF_2$—CHFCl, $(C_1-C_6)$-alkylmercapto, $(C_1-C_6)$-hydroxyalkyl, $(C_1-C_6)$-alkoxy-$(C_1-C_6)$-alkoxy, $(C_1-C_6)$-alkoxy-$(C_1-C_6)$-alkyl, $(C_1-C_6)$-alkylsulfinyl, $(C_1-C_6)$-alkylsulfonyl, $(C_1-C_6)$-alkylcarbonyl, $(C_1-C_8)$-alkoxycarbonyl, carbamoyl, N—$(C_1-C_8)$-alkylcarbamoyl, N,N-di-$(C_1-C_8)$-alkylcarbamoyl, or $(C_7-C_{11})$-aralkylcarbamoyl, optionally substituted by fluorine, chlorine, bromine, trifluoromethyl, $(C_1-C_6)$-alkoxy, N—$(C_3-C_8)$-cycloalkylcarbamoyl, N—$(C_3-C_8)$-cycloalkyl-$(C_1-C_4)$-alkylcarbamoyl, $(C_1-C_6)$-alkylcarbonyloxy, phenyl, benzyl, phenoxy, benzyloxy, $NR^yR^z$ wherein $R^y$ and $R^z$ are independently selected from hydrogen, $(C_1-C_{12})$-alkyl, $(C_1-C_8)$-alkoxy-$(C_1-C_8)$-alkyl, $(C_7-C_{12})$-aralkoxy-$(C_1-C_8)$-alkyl, $(C_6-C_{12})$-aryloxy-$(C_1-C_8)$-alkyl, $(C_3-C_{10})$-cycloalkyl, $(C_3-C_{12})$-alkenyl, $(C_3-C_{12})$-alkynyl, $(C_6-C_{12})$-aryl, $(C_7-C_{11})$-aralkyl, $(C_1-C_{12})$-alkoxy, $(C_7-C_{12})$aralkoxy, $(C_1-C_{12})$-alkylcarbonyl, $(C_3-C_8)$-cycloalkylcarbonyl, $(C_6-C_{12})$ arylcarbonyl, $(C_7-C_{16})$-aralkylcarbonyl; or further wherein $R^y$ and $R^z$ together are —$[CH_2]_h$, in which a $CH_2$ group can be replaced by O, S, N—$(C_1-C_4)$-alkylcarbonylimino, or N—$(C_1-C_4)$-alkoxycarbonylimino; phenylmercapto, phenylsulfonyl, phenylsulfinyl, sulfamoyl, N—$(C_1-C_8)$-alkylsulfamoyl, or N,N-di-$(C_1-C_8)$-alkylsulfamoyl; or alternatively $R^7$ and $R^8$, $R^8$ and $R^9$, $R^9$ and $R^{10}$, or $R^{10}$ and $R^{11}$, together are a chain selected from —$[CH_2]_n$— or —CH=CH—CH=CH—, where a $CH_2$ group of the chain is optionally replaced by O, S, SO, $SO_2$, or $NR^y$; and n is 3, 4, or 5; and if E is a heteroaryl radical, said radical can carry 1-3 substituents selected from those defined for $R^7$-$R^{11}$, or if E is a cycloalkyl radical, the radical can carry one substituent selected from those defined for $R^7$-$R^{11}$;

or where, if Q is NR', $R^4$ is alternatively R", where R' and R" are identical or different and are hydrogen, $(C_6-C_{12})$-aryl, $(C_7-C_{11})$-aralkyl, $(C_1-C_8)$-alkyl, $(C_1-C_8)$-alkoxy-$(C_1-C_8)$-alkyl, $(C_7-C_{12})$-aralkoxy-$(C_1-C_8)$-alkyl, $(C_6-C_{12})$-aryloxy-$(C_1-C_8)$-alkyl, $(C_1-C_{10})$-alkylcarbonyl, optionally substituted $(C_7-C_{16})$-aralkylcarbonyl, or optionally substituted $C_6-C_{12})$-arylcarbonyl; or R' and R" together are —$[CH_2]_h$, in which a $CH_2$ group can be replaced by O, S, N-acylimino, or N—$(C_1-C_{10})$-alkoxycarbonylimino, and h is 3 to 7.

Y is N or $CR^3$;

$R^1$, $R^2$ and $R^3$ are identical or different and are hydrogen, hydroxyl, halogen, cyano, trifluoromethyl, nitro, carboxyl, $(C_1-C_{20})$-alkyl, $(C_3-C_8)$-cycloalkyl, $(C_3-C_8)$cycloalkyl-$(C_1-C_{12})$-alkyl, $(C_3-C_8)$-cycloalkoxy, $(C_3-C_8)$-cycloalkyl-$(C_1-C_{12})$-alkoxy, $(C_3-C_8)$-cycloalkyloxy-$(C_1-C_{12})$-alkyl, $(C_3-C_8)$-cycloalkyloxy-$(C_1-C_{12})$-alkoxy, $(C_3-C_8)$-cycloalkyl-$(C_1-C_8)$-alkyl-$(C_1-C_6)$-alkoxy, $(C_3-C_8)$-cycloalkyl-$(C_1-C_8)$-alkoxy-$(C_1-C_6)$-alkyl, $(C_3-C_8)$-cycloalkyloxy-$(C_1-C_8)$-alkoxy-$(C_1-C_6)$-alkyl, $(C_3-C_8)$-cycloalkoxy-$(C_1-C_8)$-alkoxy-$(C_1-C_8)$-alkoxy, $(C_6-C_{12})$-aryl, $(C_7-C_{16})$-aralkyl, $(C_7-C_{16})$-aralkenyl, $(C_7-C_{16})$-aralkynyl, $(C_2-C_{20})$-alkenyl, $(C_2-C_{20})$-alkynyl, $(C_1-C_{20})$-alkoxy, $(C_2-C_{20})$-alkenyloxy, $(C_2-C_{20})$-alkynyloxy, retinyloxy, $(C_1-C_{20})$-alkoxy-$(C_1-C_{12})$-alkyl, $(C_1-C_{12})$-alkoxy-$(C_1-C_{12})$-alkoxy, $(C_1-C_{12})$-alkoxy-$(C_1-C_8)$-alkoxy-$(C_1-C_8)$-alkyl, $(C_6-C_{12})$-aryloxy, $(C_7-C_{16})$-aralkyloxy, $(C_6-C_{12})$-aryloxy-$(C_1-C_6)$-alkoxy, $(C_7-C_{16})$-aralkoxy-$(C_1-C_6)$-alkoxy, $(C_1-C_{16})$-hydroxyalkyl, $(C_6-C_{16})$-aryloxy-$(C_1-C_8)$-alkyl, $(C_7-C_{16})$-aralkoxy-$(C_1-C_6)$-alkyl, $(C_6-C_{12})$-aryloxy-$(C_1-C_8)$-alkoxy-$(C_1-C_6)$-alkyl, $(C_7-C_{12})$-aralkyloxy-$(C_1-C_8)$-alkoxy-$(C_1-C_6)$-alkyl, $(C_2-C_{20})$-alkenyloxy-$(C_1-C_6)$-alkyl, $(C_2-C_{20})$-alkynyloxy-$(C_1-C_6)$-alkyl, retinyloxy-$(C_1-C_6)$-alkyl, —O—$[CH_2]_xC_fH_{(2f+1-g)}F_g$, —$OCF_2$Cl, —$OCF_2$—CHFCl, $(C_1-C_{20})$-alkylcarbonyl, $(C_3-C_8)$-cycloalkylcarbonyl, $(C_6-C_{12})$-arylcarbonyl, $(C_7-C_{16})$-aralkylcarbonyl, cinnamoyl, $(C_2-C_{20})$-alkenylcarbonyl, $(C_2-C_{20})$-alkynylcarbonyl, $(C_1-C_{20})$-alkoxycarbonyl, $(C_1-C_{12})$-alkoxy-$(C_1-C_{12})$-alkoxycarbonyl, $(C_6-C_{12})$-aryloxycarbonyl, $(C_7-C_{16})$-aralkoxycarbonyl, $(C_3-C_8)$-cycloalkoxycarbonyl, $(C_2-C_{20})$-alkenyloxycarbonyl, retinyloxycarbonyl, $(C_2-C_{20})$-alkynyloxycarbonyl, $(C_6-C_{12})$-aryloxy-$(C_1-C_6)$-alkoxycarbonyl, $(C_7-C_{16})$-aralkoxy-$(C_1-C_6)$-alkoxycarbonyl, $(C_3-C_8)$-cycloalkyl-$(C_1-C_6)$-alkoxycarbonyl, $(C_3-C_8)$-cycloalkoxy-$(C_1-C_6)$-alkoxycarbonyl, $(C_1-C_{12})$-alkylcarbonyloxy, $(C_3-C_8)$-cycloalkylcarbonyloxy, $(C_6-C_{12})$-arylcarbonyloxy, $(C_7-C_{16})$-aralkylcarbonyloxy, cinnamoyloxy, $(C_2-C_{12})$-alkenylcarbonyloxy, $(C_2-C_{12})$-alkynylcarbonyloxy, $(C_1-C_{12})$-alkoxycarbonyloxy, $(C_1-C_{12})$-alkoxy-$(C_1-C_{12})$-alkoxycarbonyloxy, $(C_6-C_{12})$-aryloxycarbonyloxy, $(C_7-C_{16})$-aralkyloxycarbonyloxy, $(C_3-C_8)$-cycloalkoxycarbonyloxy, $(C_2-C_{12})$-alkenyloxycarbonyloxy, $(C_2-C_{12})$-alkynyloxycarbonyloxy, carbamoyl, N—$(C_1-C_{12})$-alkylcarbamoyl, N,N-di-$(C_1-C_{12})$-alkylcarbamoyl, N—$(C_3-C_8)$-cycloalkylcarbamoyl, N,N-dicyclo-$(C_3-C_8)$-alkylcarbamoyl, N—$(C_1-C_{10})$-alkyl-N—$(C_3-C_8)$-cycloalkylcarbamoyl, N—$((C_3-C_8)$-cycloalkyl-$(C_1-C_6)$-alkyl)-carbamoyl, N—$(C_1-C_6)$-alkyl-N—$((C_3-C_8)$-cycloalkyl-$(C_1-C_6)$-alkyl)-carbamoyl, N-(+)-dehydroabietylcarbamoyl, N—$(C_1-C_6)$-alkyl-N-(+)-dehydroabietylcarbamoyl, N—$(C_6-C_{12})$-arylcarbamoyl, N—$(C_7-C_{16})$-aralkylcarbamoyl, N—$(C_1-C_{10})$-alkyl-N—$(C_6-C_{16})$-arylcarbamoyl, N—$(C_1-C_{10})$-alkyl-N—$(C_7-C_{16})$-aralkylcarbamoyl, N—$((C_1-C_{18})$-alkoxy-$(C_1-C_{10})$-alkyl)-carbamoyl, N—$((C_6-C_{16})$-aryloxy-$(C_1-C_{10})$-alkyl)-carbamoyl, N—$((C_7-C_{16})$-aralkyloxy-$(C_1-C_{10})$-alkyl)-carbamoyl, N—$(C_1-C_{10})$-alkyl-N—$((C_1-C_{10})$-alkoxy-$(C_1-C_{10})$-alkyl)-carbamoyl, N—$(C_1-C_{10})$-alkyl-N—$((C_6-C_{12})$-aryloxy-$(C_1-C_{10})$-alkyl)-carbamoyl, N—$(C_1-C_{10})$-alkyl-N—$((C_7-C_{16})$-aralkyloxy-$(C_1-C_{10})$-alkyl)-carbamoyl; $CON(CH_2)_h$, in which a $CH_2$ group can be replaced by O, S, N—$(C_1-C_8)$-alkylimino, N—$(C_3-C_8)$-cycloalkylimino, N—$(C_3-C_8)$-cycloalkyl-$(C_1-C_4)$-alkylimino, N—$(C_6-C_{12})$-arylimino, N—$(C_7-C_{16})$-aralkylimino, N—$(C_1-C_4)$-alkoxy-$(C_1-C_6)$-alkylimino, and h is from 3 to 7; a carbamoyl radical of the Formula R

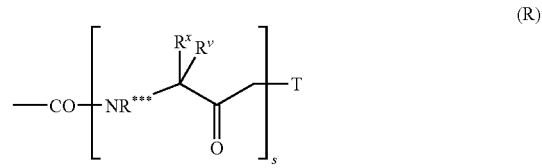

(R)

in which $R^x$ and $R^y$ are each independently selected from hydrogen, $(C_1-C_6)$-alkyl, $(C_3-C_7)$-cycloalkyl, aryl, or the substituent of an α-carbon of an α-amino acid, to which the L- and D-amino acids belong, s is 1-5, T is OH, or NR*R**, and R*, R and R* are identical or different and are selected from hydrogen, ($C_6$-$C_{12}$)-aryl, ($C_7$-$C_{11}$)-aralkyl, ($C_1$-$C_8$)-alkyl, ($C_3$-$C_8$)-cycloalkyl, (+)-dehydroabietyl, ($C_1$-$C_8$)-alkoxy-($C_1$-$C_8$)-alkyl, ($C_7$-$C_{12}$)-aralkoxy-($C_1$-$C_8$)-alkyl, ($C_6$-$C_{12}$)-aryloxy-($C_1$-$C_8$)-alkyl, ($C_1$-$C_{10}$)-alkanoyl, optionally substituted ($C_7$-$C_{16}$)-aralkanoyl, optionally substituted ($C_6$-$C_{12}$)-aroyl; or R* and R** together are —[$CH_2$]$_h$, in which a $CH_2$ group can be replaced by O, S, SO, $SO_2$, N-acylamino, N—($C_1$-$C_{10}$)-alkoxycarbonylimino, N—($C_1$-$C_8$)-alkylimino, N—($C_3$-$C_8$)-cycloalkylimino, N—($C_3$-$C_8$)-cycloalkyl-($C_1$-$C_4$)-alkylimino, N—($C_6$-$C_{12}$)-arylimino, N—($C_7$-$C_{16}$)-aralkylimino, N—($C_1$-$C_4$)-alkoxy-($C_1$-$C_6$)-alkylimino, and h is from 3 to 7; carbamoyloxy, N—($C_1$-$C_{12}$)-alkylcarbamoyloxy, N,N-di-($C_1$-$C_{12}$)-alkylcarbamoyloxy, N—($C_3$-$C_8$)-cycloalkylcarbamoyloxy, N—($C_6$-$C_{12}$)-arylcarbamoyloxy, N—($C_7$-$C_{16}$)-aralkylcarbamoyloxy, N—($C_1$-$C_{10}$)-alkyl-N—($C_6$-$C_{12}$)-arylcarbamoyloxy, N—($C_1$-$C_{10}$)-alkyl-N—($C_7$-$C_{16}$)-aralkylcarbamoyloxy, N—(($C_1$-$C_{10}$)-alkyl)-carbamoyloxy, N—(($C_6$-$C_{12}$)-aryloxy-($C_1$-$C_{10}$)-alkyl)-carbamoyloxy, N—(($C_7$-$C_{16}$)-aralkyloxy-($C_1$-$C_{10}$)-alkyl)-carbamoyloxy, N—($C_1$-$C_{10}$)-alkyl-N—(($C_1$-$C_{10}$)-alkoxy-($C_1$-$C_{10}$)-alkyl)-carbamoyloxy, N—($C_1$-$C_{10}$)-alkyl-N—(($C_6$-$C_{12}$)-aryloxy-($C_1$-$C_{10}$)-alkyl)-carbamoyloxy, N—($C_1$-$C_{10}$)-alkyl-N—(($C_7$-$C_{16}$)-aralkyloxy-($C_1$-$C_{10}$)-alkyl)-carbamoyloxyamino, ($C_1$-$C_{12}$)-alkylamino, di-($C_1$-$C_{12}$)-alkylamino, ($C_3$-$C_8$)-cycloalkylamino, ($C_3$-$C_{12}$)-alkenylamino, ($C_3$-$C_{12}$)-alkynylamino, N—($C_6$-$C_{12}$)-arylamino, N—($C_7$-$C_{11}$)-aralkylamino, N-alkyl-aralkylamino, N-alkyl-arylamino, ($C_1$-$C_{12}$)-alkoxyamino, ($C_1$-$C_{12}$)-alkoxy-N—($C_1$-$C_{10}$)-alkylamino, ($C_1$-$C_{12}$)-alkanoylamino, ($C_3$-$C_8$)-cycloalkanoylamino, ($C_6$-$C_{12}$)-aroylamino, ($C_7$-$C_{16}$)-aralkanoylamino, ($C_1$-$C_{12}$)-alkanoyl-N—($C_1$-$C_{10}$)-alkylamino, ($C_3$-$C_8$)-cycloalkanoyl-N—($C_1$-$C_{10}$)-alkylamino, ($C_6$-$C_{12}$)-aroyl-N—($C_1$-$C_{10}$)-alkylamino, ($C_7$-$C_{11}$)-aralkanoyl-N—($C_1$-$C_{10}$)-alkylamino, ($C_1$-$C_{12}$)-alkanoylamino-($C_1$-$C_8$)-alkyl, ($C_3$-$C_8$)-cycloalkanoylamino-($C_1$-$C_8$)-alkyl, ($C_6$-$C_{12}$)-aroylamino-($C_1$-$C_8$)-alkyl, ($C_7$-$C_{16}$)-aralkanoylamino-($C_1$-$C_8$)-alkyl, amino-($C_1$-$C_{10}$)-alkyl, N—($C_1$-$C_{10}$)-alkylamino-($C_1$-$C_{10}$)-alkyl, N,N-di-($C_1$-$C_{10}$)-alkylamino-($C_1$-$C_{10}$)-alkyl, ($C_3$-$C_8$)-cycloalkylamino($C_1$-$C_{10}$)-alkyl, ($C_1$-$C_{20}$)-alkylmercapto, ($C_1$-$C_{20}$)-alkylsulfinyl, ($C_1$-$C_{20}$)-alkylsulfonyl, ($C_6$-$C_{12}$)-arylmercapto, ($C_6$-$C_{12}$)-arylsulfinyl, ($C_6$-$C_{12}$)-arylsulfonyl, ($C_7$-$C_{16}$)-aralkylmercapto, ($C_7$-$C_{16}$)-aralkylsulfinyl, ($C_7$-$C_{16}$)-aralkylsulfonyl, ($C_1$-$C_{12}$)-alkylmercapto-($C_1$-$C_6$)-alkyl, ($C_1$-$C_{12}$)-alkylsulfinyl-($C_1$-$C_6$)-alkyl, ($C_1$-$C_{12}$)-alkylsulfonyl-($C_1$-$C_6$)-alkyl, ($C_6$-$C_{12}$)-arylmercapto-($C_1$-$C_6$)-alkyl, ($C_6$-$C_{12}$)-arylsulfinyl-($C_1$-$C_6$)-alkyl, ($C_6$-$C_{12}$)-arylsulfonyl-($C_1$-$C_6$)-alkyl, ($C_7$-$C_{16}$)-aralkylmercapto-($C_1$-$C_6$)-alkyl, ($C_7$-$C_{16}$)-aralkylsulfinyl-($C_1$-$C_6$)-alkyl, ($C_7$-$C_{16}$)-aralkylsulfonyl-($C_1$-$C_6$)-alkyl, sulfamoyl, N—($C_1$-$C_{10}$)-alkylsulfamoyl, N,N-di-($C_1$-$C_{10}$)-alkylsulfamoyl, ($C_3$-$C_8$)-cycloalkylsulfamoyl, N—($C_6$-$C_{12}$)-arylsulfamoyl, N—($C_7$-$C_{16}$)-aralkylsulfamoyl, N—($C_1$-$C_{10}$)-alkyl-N—($C_6$-$C_{12}$)-arylsulfamoyl, N—($C_1$-$C_{10}$)-alkyl-N—($C_7$-$C_{16}$)-aralkylsulfamoyl, ($C_1$-$C_{10}$)-alkylsulfonamido, N—(($C_1$-$C_{10}$)-alkyl)-($C_1$-$C_{10}$)-alkylsulfonamido, ($C_7$-$C_{16}$)-aralkylsulfonamido, and N—(($C_1$-$C_{10}$)-alkyl-($C_7$-$C_{16}$)-aralkylsulfonamido;

where an aryl radical may be substituted by 1 to 5 substituents selected from hydroxyl, halogen, cyano, trifluoromethyl, nitro, carboxyl, ($C_2$-$C_{16}$)-alkyl, ($C_3$-$C_8$)-cycloalkyl, ($C_3$-$C_8$)-cycloalkyl-($C_1$-$C_{12}$)-alkyl, ($C_3$-$C_8$)-cycloalkoxy, ($C_3$-$C_8$)-cycloalkyl-($C_1$-$C_{12}$)-alkoxy, ($C_3$-$C_8$)-cycloalkyloxy-($C_1$-$C_{12}$)-alkyl, ($C_3$-$C_8$)-cycloalkyloxy-($C_1$-$C_{12}$)-alkoxy, ($C_3$-$C_8$)-cycloalkyl-($C_1$-$C_8$)-alkyl-($C_1$-$C_6$)-alkoxy, ($C_3$-$C_8$)-cycloalkyl($C_1$-$C_8$)-alkoxy-($C_1$-$C_6$)-alkyl, ($C_3$-$C_8$)-cycloalkyloxy-($C_1$-$C_8$)-alkoxy-($C_1$-$C_6$)-alkyl, ($C_3$-$C_8$)-cycloalkoxy-($C_1$-$C_8$)-alkoxy-($C_1$-$C_8$)-alkoxy, ($C_6$-$C_{12}$)-aryl, ($C_7$-$C_{16}$)-aralkyl, ($C_2$-$C_{16}$)-alkenyl, ($C_2$-$C_{12}$)-alkynyl, ($C_1$-$C_{16}$)-alkoxy, ($C_1$-$C_{16}$)-alkenyloxy, ($C_1$-$C_{12}$)-alkoxy-($C_1$-$C_{12}$)-alkyl, ($C_1$-$C_{12}$)-alkoxy-($C_1$-$C_{12}$)-alkoxy, ($C_1$-$C_{12}$)-alkoxy($C_1$-$C_8$)-alkoxy-($C_1$-$C_8$)-alkyl, ($C_6$-$C_{12}$)-aryloxy, ($C_7$-$C_{16}$)-aralkyloxy, ($C_6$-$C_{12}$)-aryloxy-($C_1$-$C_6$)-alkoxy, ($C_7$-$C_{16}$)-aralkoxy-($C_1$-$C_6$)-alkoxy, ($C_1$-$C_8$)-hydroxyalkyl, ($C_6$-$C_{16}$)-aryloxy-($C_1$-$C_8$)-alkyl, ($C_7$-$C_{16}$)-aralkoxy-($C_1$-$C_8$)-alkyl, ($C_6$-$C_{12}$)-aryloxy-($C_1$-$C_8$)-alkoxy-($C_1$-$C_6$)-alkyl, ($C_7$-$C_{12}$)-aralkyloxy-($C_1$-$C_8$)-alkoxy-($C_1$-$C_6$)-alkyl, —O—[$CH_2$]$_x$$CfH_{(2f+1-g)}F_g$, —$OCF_2Cl$, —$OCF_2$—CHFCl, ($C_1$-$C_{12}$)-alkylcarbonyl, ($C_3$-$C_8$)-cycloalkylcarbonyl, ($C_6$-$C_{12}$)-arylcarbonyl, ($C_7$-$C_{16}$)-aralkylcarbonyl, ($C_1$-$C_{12}$)-alkoxycarbonyl, ($C_1$-$C_{12}$)-alkoxy-($C_1$-$C_{12}$)-alkoxycarbonyl, ($C_6$-$C_{12}$)-aryloxycarbonyl, ($C_7$-$C_{16}$)-aralkoxycarbonyl, ($C_3$-$C_8$)-cycloalkoxycarbonyl, ($C_2$-$C_{12}$)-alkenyloxycarbonyl, ($C_2$-$C_{12}$)-alkynyloxycarbonyl, ($C_6$-$C_{12}$)-aryloxy-($C_1$-$C_6$)-alkoxycarbonyl, ($C_7$-$C_{16}$)-aralkoxy-($C_1$-$C_6$)-alkoxycarbonyl, ($C_3$-$C_8$)-cycloalkyl-($C_1$-$C_6$)-alkoxycarbonyl, ($C_3$-$C_8$)-cycloalkoxy-($C_1$-$C_6$)-alkoxycarbonyl, ($C_1$-$C_{12}$)-alkylcarbonyloxy, ($C_3$-$C_8$)-cycloalkylcarbonyloxy, ($C_6$-$C_{12}$)-arylcarbonyloxy, ($C_7$-$C_{16}$)-aralkylcarbonyloxy, cinnamoyloxy, ($C_2$-$C_{12}$)-alkenylcarbonyloxy, ($C_2$-$C_{12}$)-alkynylcarbonyloxy, ($C_1$-$C_{12}$)-alkoxycarbonyloxy, ($C_1$-$C_{12}$)-alkoxy-($C_1$-$C_{12}$)-alkoxycarbonyloxy, ($C_6$-$C_{12}$)-aryloxycarbonyloxy, ($C_7$-$C_{16}$)-aralkyloxycarbonyloxy, ($C_3$-$C_8$)-cycloalkoxycarbonyloxy, ($C_2$-$C_{12}$)-alkenyloxycarbonyloxy, ($C_2$-$C_{12}$)-alkynyloxycarbonyloxy, carbamoyl, N—($C_1$-$C_{12}$)-alkylcarbamoyl, N,N-di($C_1$-$C_{12}$)-alkylcarbamoyl, N—($C_3$-$C_8$)-cycloalkylcarbamoyl, N,N-dicyclo-($C_3$-$C_8$)-alkylcarbamoyl, N—($C_1$-$C_{10}$)-alkyl-N—($C_3$-$C_8$)-cycloalkylcarbamoyl, N—(($C_3$-$C_8$)-cycloalkyl-($C_1$-$C_6$)-alkyl)carbamoyl, N—($C_1$-$C_6$)-alkyl-N—(($C_3$-$C_8$)-cycloalkyl-($C_1$-$C_6$)-alkyl)carbamoyl, N-(+)-dehydroabietylcarbamoyl, N—($C_1$-$C_6$)-alkyl-N-(+)-dehydroabietylcarbamoyl, N—($C_6$-$C_{12}$)-arylcarbamoyl, N—($C_7$-$C_{16}$)-aralkylcarbamoyl, N—($C_1$-$C_{10}$)-alkyl-N—($C_6$-$C_{16}$)-arylcarbamoyl, N—($C_1$-$C_{10}$)-alkyl-N—($C_7$-$C_{16}$)-aralkylcarbamoyl, N—(($C_1$-$C_{16}$)-alkoxy-($C_1$-$C_{10}$)-alkyl)carbamoyl, N—(($C_6$-$C_{16}$)-aryloxy-($C_1$-$C_{10}$)-alkyl)carbamoyl, N—(($C_7$-$C_{16}$)-aralkyloxy-($C_1$-$C_{10}$)-alkyl)carbamoyl, N—($C_1$-$C_{10}$)-alkyl-N—(($C_1$-$C_{10}$)-alkoxy-($C_1$-$C_{10}$)-alkyl)carbamoyl, N—($C_1$-$C_{10}$)-alkyl-N—(($C_6$-$C_{12}$)-aryloxy-($C_1$-$C_{10}$)-alkyl)carbamoyl, N—($C_1$-$C_{10}$)-alkyl-N—(($C_7$-$C_{16}$)-aralkyloxy-($C_1$-$C_{10}$)-alkyl)-carbamoyl, $CON(CH_2)_h$, in which a $CH_2$ group can be replaced by, O, S, N—($C_1$-$C_8$)-alkylimino, N—($C_3$-$C_8$)-cycloalkylimino, N—($C_3$-$C_8$)-cycloalkyl-($C_1$-$C_4$)-alkylimino, N—($C_6$-$C_{12}$)-arylimino, N—($C_7$-$C_{16}$)-aralkylimino, N—($C_1$-$C_4$)-alkoxy-($C_1$-$C_6$)-alkylimino, and h is from 3 to 7; carbamoyloxy, N—($C_1$-$C_{12}$)-alkylcarbamoyloxy, N,N-di-($C_1$-$C_{12}$)-alkylcarbamoyloxy, N—($C_3$-$C_8$)-cycloalkylcarbamoyloxy, N—($C_6$-$C_{16}$)-arylcarbamoyloxy, N—($C_7$-$C_{16}$)-aralkylcarbamoyloxy, N—($C_1$-$C_{10}$)-alkyl-N—($C_6$-$C_{12}$)-arylcarbamoyloxy, N—($C_1$-$C_{10}$)-alkyl-N—($C_7$-$C_{16}$)-aralkylcarbamoyloxy, N—((C$_1$-C$_{10}$)-alkyl)carbamoyloxy, N—((C$_6$-C$_{12}$)-aryloxy-(C$_1$-C$_{10}$)-alkyl)carbamoyloxy, N—((C$_7$-C$_{16}$)-aralkyloxy-(C$_1$-C$_{10}$)-alkyl)carbamoyloxy, N—(C$_1$-C$_{10}$)-alkyl-N—((C$_1$-C$_{10}$)-alkoxy-(C$_1$-C$_{10}$)-alkyl)carbamoyloxy, N—(C$_1$-C$_{10}$)-alkyl-N—((C$_6$-C$_{12}$)-aryloxy-(C$_1$-C$_{10}$)-alkyl)carbamoyloxy, N—(C$_1$-C$_{10}$)-alkyl-N—((C$_7$-C$_{16}$)-aralkyloxy-(C$_1$-C$_{10}$)-alkyl)carbamoyloxy, amino, (C$_1$-C$_{12}$)-alkylamino, di-(C$_1$-C$_{12}$)-alkylamino, (C$_3$-C$_8$)-cycloalkylamino, (C$_3$-C$_{12}$)-alkenylamino, (C$_3$-C$_{12}$)-alkynylamino, N—(C$_6$-C$_{12}$)-arylamino, N—(C$_7$-C$_{11}$)-aralkylamino, N-alkyl-aralkylamino, N-alkyl-arylamino, (C$_1$-C$_{12}$)-alkoxyamino, (C$_1$-C$_{12}$)-alkoxy-N—(C$_1$-C$_{10}$)-alkylamino, (C$_1$-C$_{12}$)-alkanoylamino, (C$_3$-C$_8$)-cycloalkanoylamino, (C$_6$-C$_{12}$)-aroylamino, (C$_7$-C$_{16}$)-aralkanoylamino, (C$_1$-C$_{12}$)-alkanoyl-N-(C$_1$-C$_{10}$)-alkylamino, (C$_3$-C$_8$)-cycloalkanoyl-N—(C$_1$-C$_{10}$)-alkylamino, (C$_6$-C$_{12}$)-aroyl-N—(C$_1$-C$_{10}$)-alkylamino, (C$_7$-C$_{11}$)-aralkanoyl-N—(C$_1$-C$_{10}$)-alkylamino, (C$_1$-C$_{12}$)-alkanoylamino-(C$_1$-C$_8$)-alkyl, (C$_3$-C$_8$)-cycloalkanoylamino-(C$_1$-C$_8$)-alkyl, (C$_6$-C$_{12}$)-aroylamino-(C$_1$-C$_8$)-alkyl, (C$_7$-C$_{16}$)-aralkanoylamino-(C$_1$-C$_8$)-alkyl, amino-(C$_1$-C$_{10}$)-alkyl, N—(C$_1$-C$_{10}$)-alkylamino-(C$_1$-C$_{10}$)-alkyl, N,N-di-(C$_1$-C$_{10}$)-alkylamino-(C$_1$-C$_{10}$)-alkyl, (C$_3$-C$_8$)-cycloalkylamino-(C$_1$-C$_{10}$)-alkyl, (C$_1$-C$_{12}$)-alkylmercapto, (C$_1$-C$_{12}$)-alkylsulfinyl, (C$_1$-C$_{12}$)-alkylsulfonyl, (C$_6$-C$_{16}$)-arylmercapto, (C$_6$-C$_{16}$)-arylsulfinyl, (C$_6$-C$_{16}$)-arylsulfonyl, (C$_7$-C$_{16}$)-aralkylmercapto, (C$_7$-C$_{16}$)-aralkylsulfinyl, or (C$_7$-C$_{16}$)-aralkylsulfonyl;

or wherein R$^1$ and R$^2$, or R$^2$ and R$^3$ form a chain [CH$_2$]$_o$, which is saturated or unsaturated by a C=C double bond, in which 1 or 2 CH$_2$ groups are optionally replaced by O, S, SO, SO$_2$, or NR', and R' is hydrogen, (C$_6$-C$_{12}$)-aryl, (C$_1$-C$_8$)-alkyl, (C$_1$-C$_8$)-alkoxy-(C$_1$-C$_8$)-alkyl, (C$_7$-C$_{12}$)-aralkoxy-(C$_1$-C$_8$)-alkyl, (C$_6$-C$_{12}$)-aryloxy-(C$_1$-C$_8$)-alkyl, (C$_1$-C$_{10}$)-alkanoyl, optionally substituted (C$_7$-C$_{16}$)-aralkanoyl, or optionally substituted (C$_6$-C$_{12}$)-aroyl; and o is 3, 4 or 5;

or wherein the radicals R$^1$ and R$^2$, or R$^2$ and R$^3$, together with the pyridine or pyridazine carrying them, form a 5,6,7,8-tetrahydroisoquinoline ring, a 5,6,7,8-tetrahydroquinoline ring, or a 5,6,7,8-tetrahydrocinnoline ring;

or wherein R$^1$ and R$^2$, or R$^2$ and R$^3$ form a carbocyclic or heterocyclic 5- or 6-membered aromatic ring;

or where R$^1$ and R$^2$, or R$^2$ and R$^3$, together with the pyridine or pyridazine carrying them, form an optionally substituted heterocyclic ring systems selected from thienopyridines, furanopyridines, pyridopyridines, pyrimidinopyridines, imidazopyridines, thiazolopyridines, oxazolopyridines, quinoline, isoquinoline, and cinnoline; where quinoline, isoquinoline or cinnoline preferably satisfy the Formulae Ia, Ib and Ic:

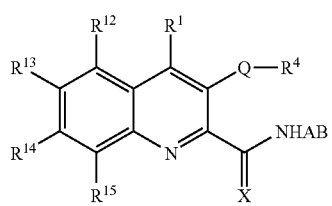

(Ia)

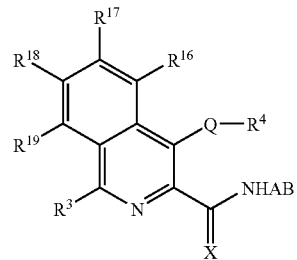

(Ib)

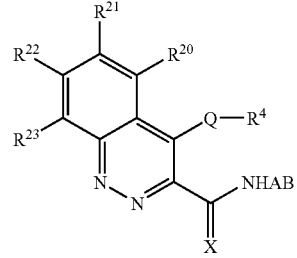

(Ic)

and the substituents R$^{12}$ to R$^{23}$ in each case independently of each other have the meaning of R$^1$, R$^2$ and R$^3$;

or wherein the radicals R$^1$ and R$^2$, together with the pyridine carrying them, form a compound of Formula Id:

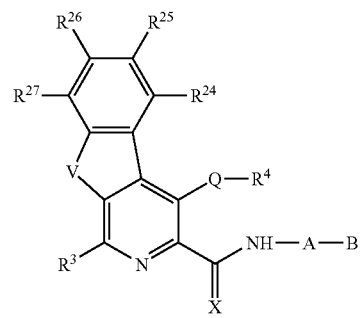

(Id)

where
V is S, O, or NR$^k$, and R$^k$ is selected from hydrogen, (C$_1$-C$_6$)-alkyl, aryl, or benzyl; where an aryl radical may be optionally substituted by 1 to 5 substituents as defined above; and
R$^{24}$, R$^{25}$, R$^{26}$, and R$^{27}$ in each case independently of each other have the meaning of R$^1$, R$^2$ and R$^3$;
f is 1 to 8;
g is 0 or 1 to (2f+1);
x is 0 to 3; and
h is 3 to 7;
including the physiologically active salts, esters, and prodrugs derived therefrom.

Exemplary compounds according to Formula I are described in European Patent Nos. EP0650960 and EP0650961. All compounds listed in EP0650960 and EP0650961, in particular, those listed in the compound claims and the final products of the working examples, are hereby incorporated into the present application by reference herein. Additionally, exemplary compounds according to Formula I are described in U.S. Pat. No. 5,658,933. All compounds listed in U.S. Pat. No. 5,658,933, in particular, those listed in the compound claims and the final products of the working examples, are hereby incorporated into the present application by reference herein.

Additional compounds according to Formula I are substituted heterocyclic carboxyamides described in U.S. Pat. No. 5,620,995; 3-hydroxypyridine-2-carboxamidoesters described in U.S. Pat. No. 6,020,350; sulfonamidocarbonylpyridine-2-carboxamides described in U.S. Pat. No. 5,607,954; and sulfonamidocarbonyl-pyridine-2-carboxamides and sulfonamidocarbonyl-pyridine-2-carboxamide esters described in U.S. Pat. Nos. 5,610,172 and 5,620,996. All compounds listed in these patents, in particular, those compounds listed in the compound claims and the final products of the working examples, are hereby incorporated into the present application by reference herein.

Exemplary compounds according to Formula Ia are described in U.S. Pat. Nos. 5,719,164 and 5,726,305. All compounds listed in the foregoing patents, in particular, those listed in the compound claims and the final products of the working examples, are hereby incorporated into the present application by reference herein. Exemplary compounds according to Formula Ib are described in U.S. Pat. No. 6,093,730. All compounds listed in U.S. Pat. No. 6,093,730, in particular, those listed in the compound claims and the final products of the working examples, are hereby incorporated into the present application by reference herein In certain embodiments, compounds of the invention are pyridine-2-carboxamides. In one embodiment, the compound is selected from a compound of the Formula I, wherein A is —$CR^5R^6$—, and $R^5$ and $R^6$ are each independently selected from the group consisting of hydrogen, ($C_1$-$C_6$)-alkyl, ($C_3$-$C_7$)-cycloalkyl, aryl, or a substituent of the α-carbon atom of an α-amino acid, wherein the amino acid is a natural L-amino acid or its D-isomer;

B is —$CO_2H$ or a $CO_2$-G carboxyl radical, where G is a radical of an alcohol G-OH in which G is selected from the group consisting of ($C_1$-$C_{20}$)-alkyl radical, ($C_3$-$C_8$) cycloalkyl radical, ($C_2$-$C_{20}$)-alkenyl radical, ($C_3$-$C_8$)-cycloalkenyl radical, retinyl radical, ($C_2$-$C_{20}$)-alkynyl radical, ($C_4$-$C_{20}$)-alkenynyl radical;

X is O;

Q is O;

$R^4$ is selected from the group consisting of hydrogen, ($C_1$-$C_{10}$)-alkyl, ($C_2$-$C_{10}$)-alkenyl, ($C_2$-$C_{10}$)-alkynyl, wherein alkenyl or alkynyl contains one or two C═C multiple bonds; unsubstituted fluoroalkyl radical of the formula —$[CH_2]_x$—$C_fH_{(2f+1-g)}$—$F_g$, aryl, heteroaryl, and ($C_7$-$C_{11}$)-aralkyl;

Y is $CR^3$;

$R^1$, $R^2$ and $R^3$ are identical or different and are selected from the group consisting of hydrogen, hydroxyl, halogen, cyano, trifluoromethyl, nitro, carboxyl; ($C_1$-$C_{20}$)-alkyl, ($C_3$-$C_8$)-cycloalkyl, ($C_3$-$C_8$)-cycloalkoxy, ($C_6$-$C_{12}$)-aryl, ($C_7$-$C_{16}$)-aralkyl, ($C_7$-$C_{16}$)-aralkenyl, ($C_7$-$C_{16}$)-aralkynyl, ($C_2$-$C_{20}$)-alkenyl, ($C_2$-$C_{20}$)-alkynyl, ($C_1$-$C_{20}$)-alkoxy, ($C_2$-$C_{20}$)-alkenyloxy, ($C_2$-$C_{20}$)-alkynyloxy, retinyloxy, ($C_6$-$C_{12}$)-aryloxy, ($C_7$-$C_{16}$)-aralkyloxy, ($C_1$-$C_{16}$)-hydroxyalkyl, —O—$[CH_2]_xC_fH_{(2f+1-g)}$$F_g$, —$OCF_2Cl$, —$OCF_2$—$CHFCl$, ($C_1$-$C_{20}$)-alkylcarbonyl, ($C_3$-$C_8$)-cycloalkylcarbonyl, ($C_6$-$C_2$)-arylcarbonyl, ($C_7$-$C_{16}$)-aralkylcarbonyl, cinnamoyl, ($C_2$-$C_{20}$)-alkenylcarbonyl, ($C_2$-$C_{20}$)-alkynylcarbonyl, ($C_1$-$C_{20}$)-alkoxycarbonyl, ($C_6$-$C_{12}$)-aryloxycarbonyl, ($C_7$-$C_{16}$)-aralkoxycarbonyl, ($C_3$-$C_8$)-cycloalkoxycarbonyl, ($C_2$-$C_{20}$)-alkenyloxycarbonyl, retinyloxycarbonyl, ($C_2$-$C_{20}$)-alkynyloxycarbonyl, ($C_1$-$C_{12}$)-alkylcarbonyloxy, ($C_3$-$C_8$)-cycloalkylcarbonyloxy, ($C_6$-$C_{12}$)-arylcarbonyloxy, ($C_7$-$C_{16}$)-aralkylcarbonyloxy, cinnamoyloxy, ($C_2$-$C_{12}$)-alkenylcarbonyloxy, ($C_2$-$C_{12}$)-alkynylcarbonyloxy, ($C_1$-$C_{12}$)-alkoxycarbonyloxy, ($C_6$-$C_{12}$)-aryloxycarbonyloxy, ($C_7$-$C_{16}$)-aralkyloxycarbonyloxy, ($C_3$-$C_8$)-cycloalkoxycarbonyloxy, ($C_2$-$C_{12}$)-alkenyloxycarbonyloxy, ($C_2$-$C_{12}$)-alkynyloxycarbonyloxy, carbamoyl, N—($C_1$-$C_{12}$)-alkylcarbamoyl, N,N-di-($C_1$-$C_{12}$)-alkylcarbamoyl, N—($C_3$-$C_8$)-cycloalkylcarbamoyl, N,N-dicyclo-($C_3$-$C_8$)-alkylcarbamoyl, N—($C_1$-$C_{10}$)-alkyl-N—($C_3$-$C_8$)-cycloalkylcarbamoyl, N—(($C_3$-$C_8$)-cycloalkyl-($C_1$-$C_6$)-alkyl)carbamoyl, N—($C_1$-$C_6$)-alkyl-N—(($C_3$-$C_8$)-cycloalkyl-($C_1$-$C_6$)-alkyl)carbamoyl, N-(+)-dehydroabietylcarbamoyl, N—($C_1$-$C_6$)-alkyl-N-(+)-dehydroabietylcarbamoyl, N—($C_6$-$C_{12}$)-arylcarbamoyl, N—($C_7$-$C_{16}$)-aralkylcarbamoyl, N—($C_1$-$C_{10}$)-alkyl-N—($C_6$-$C_{16}$)-arylcarbamoyl, N—($C_1$-$C_{10}$)-alkyl-N—($C_7$-$C_{16}$)-aralkylcarbamoyl, N—(($C_1$-$C_{16}$)-alkoxy-($C_1$-$C_{10}$)-alkyl)carbamoyl, N—(($C_6$-$C_{16}$)-aryloxy-($C_1$-$C_{10}$)-alkyl)carbamoyl, N—(($C_7$-$C_{16}$)-aralkyloxy-($C_1$-$C_{10}$)-alkyl)carbamoyl, N—($C_1$-$C_{10}$)-alkyl-N—(($C_1$-$C_{10}$)-alkoxy-($C_1$-$C_{10}$)-alkyl)carbamoyl, N—($C_1$-$C_{10}$)-alkyl-N—(($C_6$-$C_{12}$)-aryloxy-($C_1$-$C_{10}$)-alkyl)carbamoyl, N—($C_1$-$C_{10}$)-alkyl-N—(($C_7$-$C_{16}$)-aralkyloxy-($C_1$-$C_{10}$)-alkyl)-carbamoyl, carbamoyloxy, N—($C_1$-$C_{12}$)-alkylcarbamoyloxy, N,N-di-($C_1$-$C_{12}$)-alkylcarbamoyloxy, N—($C_3$-$C_8$)-cycloalkylcarbamoyloxy, N—($C_6$-$C_{12}$)-arylcarbamoyloxy, N—($C_7$-$C_{16}$)-aralkylcarbamoyloxy, N—($C_1$-$C_{10}$)-alkyl-N—($C_6$-$C_{12}$)-arylcarbamoyloxy, N—($C_1$-$C_{10}$)-alkyl-N—($C_7$-$C_{16}$)-aralkylcarbamoyloxy, N—(($C_1$-$C_{10}$)-alkyl)-carbamoyloxy, N—($C_1$-$C_{10}$)-alkyl-N—(($C_7$-$C_{16}$)-aralkyloxy-($C_1$-$C_{10}$)-alkyl)-carbamoyloxyamino, ($C_1$-$C_{12}$)-alkylamino, di-($C_1$-$C_{12}$)-alkylamino, ($C_3$-$C_8$)-cycloalkylamino, ($C_3$-$C_{12}$)-alkenylamino, ($C_3$-$C_{12}$)-alkynylamino, N—($C_6$-$C_{12}$)-arylamino, N—($C_7$-$C_{11}$)-aralkylamino, N-alkyl-aralkylamino, N-alkyl-arylamino, ($C_1$-$C_{12}$)-alkoxyamino, ($C_1$-$C_{12}$)-alkoxy-N—($C_1$-$C_{10}$)-alkylamino, ($C_1$-$C_{12}$)-alkanoylamino, ($C_3$-$C_8$)-cycloalkanoylamino, ($C_6$-$C_{12}$)-aroylamino, ($C_7$-$C_{16}$)-aralkanoylamino, ($C_1$-$C_{12}$)-alkanoyl-N—($C_1$-$C_{10}$)-alkylamino, ($C_3$-$C_8$)-cycloalkanoyl-N—($C_1$-$C_{10}$)-alkylamino, ($C_6$-$C_{12}$)-aroyl-N—($C_1$-$C_{10}$)-alkylamino, ($C_7$-$C_{11}$)-aralkanoyl-N—($C_1$-$C_{10}$)-alkylamino, amino-($C_1$-$C_{10}$)-alkyl, ($C_1$-$C_{20}$)-alkylmercapto, ($C_1$-$C_{20}$)-alkylsulfinyl, ($C_1$-$C_{20}$)-alkylsulfonyl, ($C_6$-$C_{12}$)-arylmercapto, ($C_6$-$C_{12}$)-arylsulfinyl, ($C_6$-$C_{12}$)-arylsulfonyl, ($C_7$-$C_{16}$)-aralkylmercapto, ($C_7$-$C_{16}$)-aralkylsulfinyl, ($C_7$-$C_{16}$)-aralkylsulfonyl, sulfamoyl, N—($C_1$-$C_{10}$)-alkylsulfamoyl, N,N-di-($C_1$-$C_{10}$)-alkylsulfamoyl, ($C_3$-$C_8$)-cycloalkylsulfamoyl, N—($C_6$-$C_{12}$)-arylsulfamoyl, N—($C_7$-$C_{16}$)-aralkylsulfamoyl, N—($C_1$-$C_{10}$)-alkyl-N—($C_6$-$C_{12}$)-arylsulfamoyl, N—($C_1$-$C_{10}$)-alkyl-N—($C_7$-$C_{16}$)-aralkylsulfamoyl, ($C_1$-$C_{10}$)-alkylsulfonamido, ($C_7$-$C_{16}$)-aralkylsulfonamido, and N—(($C_1$-$C_{10}$)-alkyl-($C_7$-$C_{16}$)-aralkylsulfonamido; where an aryl radical may be substituted by 1 to 5 substituents selected from hydroxyl, halogen, cyano, trifluoromethyl, nitro, carboxyl, ($C_2$-$C_{16}$)-alkyl, ($C_3$-$C_8$)-cycloalkyl, ($C_3$-$C_8$)-cycloalkoxy, ($C_6$-$C_{12}$)-aryl, ($C_7$-$C_{16}$)-aralkyl, ($C_2$-$C_{16}$)-alkenyl, ($C_2$-$C_{12}$)-alkynyl, ($C_1$-$C_{16}$)-alkoxy, ($C_1$-$C_{16}$)-alkenyloxy, ($C_6$-$C_{12}$)-aryloxy, ($C_7$-$C_{16}$)-aralkyloxy, ($C_1$-$C_8$)-hydroxyalkyl, —O—$[CH_2]_xC_fH_{(2f+1-g)}F_g$, —$OCF_2Cl$, and —$OCF_2$—$CHFCl$;

x is 0 to 3;
f is 1 to 8; and
g is 0 or 1 to (2f+1);
including the physiologically active salts, esters, and prodrugs derived therefrom.

Pyridine-2-carboxamides of Formula I include, but are not limited to, [(3-methoxy-pyridine-2-carbonyl)-amino]-acetic acid, 3-methoxypyridine-2-carboxylic acid N—(((hexadecyloxy)-carbonyl)-methyl)-amide hydrochloride, 3-methoxypyridine-2-carboxylic acid N—(((1-octyloxy)-carbonyl)-methyl)-amide, 3-methoxypyridine-2-carboxylic acid N—(((hexyloxy)-carbonyl)-methyl)-amide, 3-methoxypyridine-2-carboxylic acid N—(((butyloxy)-carbonyl)-methyl)-amide, 3-methoxypyridine-2-carboxylic acid N—(((2-nonyloxy)-carbonyl)-methyl)-amide racemate, 3-methoxypyridine-2-carboxylic acid N—(((heptyloxy)-carbonyl)-methyl)-amide, 3-benzyloxypyridine-2-carboxylic acid N—(((octyloxy)-carbonyl)-methyl)-amide, 3-benzyloxypyridine-2-carboxylic acid N—(((butyloxy)-carbonyl)-methyl)-amide, 5-(((3-(1-butyloxy)-propyl)-amino)-carbonyl)-3-methoxypyridine-2-carboxylic acid N—((benzyloxycarbonyl)-methyl)-amide, 5-(((3-(1-butyloxy)-propyl)-amino)-carbonyl)-3-methoxypyridine-2-carboxylic acid N—(((1-butyloxy)-carbonyl)-methyl)-amide, 5-(((3-lauryloxy)-propyl)amino)-carbonyl)-3-methoxypyridine-2-carboxylic acid N—(((benzyloxy)-carbonyl)-methyl)-amide, [(3-hydroxy-pyridine-2-carbonyl)-amino]-acetic acid, and [(3-methoxy-pyridine-2-carbonyl)-amino]-acetic acid.

In certain embodiments, compounds of the invention are quinoline-2-carboxamides. In one embodiment, the compound is selected from a compound of the Formula Ia wherein A is —$CR^5R^6$—, and $R^5$ and $R^6$ are each independently selected from the group consisting of hydrogen, ($C_1$-$C_6$)-alkyl, ($C_3$-$C_7$)-cycloalkyl, aryl, or a substituent of the α-carbon atom of an α-amino acid, wherein the amino acid is a natural L-amino acid or its D-isomer;

B is —$CO_2H$ or a $CO_2$-G carboxyl radical, where G is a radical of an alcohol G-OH in which G is selected from the group consisting of ($C_1$-$C_{20}$)-alkyl radical, ($C_3$-$C_8$) cycloalkyl radical, ($C_2$-$C_{20}$)-alkenyl radical, ($C_3$-$C_8$)-cycloalkenyl radical, retinyl radical, ($C_2$-$C_{20}$)-alkynyl radical, ($C_4$-$C_{20}$)-alkenynyl radical;

X is O;
Q is O;
$R^4$ is selected from the group consisting of hydrogen, ($C_1$-$C_{10}$)-alkyl, ($C_2$-$C_{10}$)-alkenyl, ($C_2$-$C_{10}$)-alkynyl, wherein alkenyl or alkynyl contains one or two C—C multiple bonds; unsubstituted fluoroalkyl radical of the formula —$[CH_2]_x$—$C_fH_{(2f+19-g)}$—$F_g$, aryl, heteroaryl, and ($C_7$-$C_{11}$)-aralkyl;

$R^1$, $R^{12}$, $R^{13}$, $R^{14}$ and $R^{15}$ are identical or different and are selected from the group consisting of hydrogen, hydroxyl, halogen, cyano, trifluoromethyl, nitro, carboxyl; ($C_1$-$C_{20}$)-alkyl, ($C_3$-$C_8$)-cycloalkyl, ($C_3$-$C_8$)-cycloalkoxy, ($C_6$-$C_{12}$)-aryl, ($C_7$-$C_{16}$)-aralkyl, ($C_7$-$C_{16}$)-aralkenyl, ($C_7$-$C_{16}$)-aralkynyl, ($C_2$-$C_{20}$)-alkenyl, ($C_2$-$C_{20}$)-alkynyl, ($C_1$-$C_{20}$)-alkoxy, ($C_2$-$C_{20}$)-alkenyloxy, ($C_2$-$C_{20}$)-alkynyloxy, retinyloxy, ($C_6$-$C_{12}$)-aryloxy, ($C_7$-$C_{16}$)-aralkyloxy, ($C_1$-$C_{16}$)-hydroxyalkyl, —O—$[CH_2]_xC_fH_{(2f+1-g)}F_g$, —$OCF_2Cl$, —$OCF_2$—$CHFCl$, ($C_1$-$C_{20}$)-alkylcarbonyl, ($C_3$-$C_8$)-cycloalkylcarbonyl, ($C_6$-$C_{12}$)-arylcarbonyl, ($C_7$-$C_{16}$)-aralkylcarbonyl, cinnamoyl, ($C_2$-$C_{20}$)-alkenylcarbonyl, ($C_2$-$C_{20}$)-alkynylcarbonyl, ($C_1$-$C_{20}$)-alkoxycarbonyl, ($C_6$-$C_{12}$)-aryloxycarbonyl, ($C_7$-$C_{16}$)-aralkoxycarbonyl, ($C_3$-$C_8$)-cycloalkoxycarbonyl, ($C_2$-$C_{20}$)-alkenyloxycarbonyl, retinyloxycarbonyl, ($C_2$-$C_{20}$)-alkynyloxycarbonyl, ($C_1$-$C_{12}$)-alkylcarbonyloxy, ($C_3$-$C_8$)-cycloalkylcarbonyloxy, ($C_6$-$C_{12}$)-arylcarbonyloxy, ($C_7$-$C_{16}$)-aralkylcarbonyloxy, cinnamoyloxy, ($C_2$-$C_{12}$)-alkenylcarbonyloxy, ($C_2$-$C_{12}$)-alkynylcarbonyloxy, ($C_1$-$C_{12}$)-alkoxycarbonyloxy, ($C_6$-$C_2$)-aryloxycarbonyloxy, ($C_7$-$C_{16}$)-aralkyloxycarbonyloxy, ($C_3$-$C_8$)-cycloalkoxycarbonyloxy, ($C_2$-$C_{12}$)-alkenyloxycarbonyloxy, ($C_2$-$C_{12}$)-alkynyloxycarbonyloxy, carbamoyl, N—($C_1$-$C_2$)-alkylcarbamoyl, N,N-di-($C_1$-$C_{12}$)-alkylcarbamoyl, N—($C_3$-$C_8$)-cycloalkylcarbamoyl, N,N-dicyclo-($C_3$-$C_8$)-alkylcarbamoyl, N—($C_1$-$C_{10}$)-alkyl-N—($C_3$-$C_8$)-cycloalkylcarbamoyl, N—(($C_3$-$C_8$)-cycloalkyl-($C_1$-$C_6$)-alkyl)-carbamoyl, N-(+)-dehydroabietylcarbamoyl, N—($C_1$-$C_6$)-alkyl-N-(+)-dehydroabietylcarbamoyl, N—($C_6$-$C_{12}$)-arylcarbamoyl, N—($C_7$-$C_{16}$)-aralkylcarbamoyl, N—($C_1$-$C_{10}$)-alkyl-N—($C_6$-$C_{16}$)-arylcarbamoyl, N—($C_1$-$C_{10}$)-alkyl-N—($C_7$-$C_{16}$)-aralkylcarbamoyl, carbamoyloxy, N—($C_1$-$C_{12}$)-alkylcarbamoyloxy, N,N-di-($C_1$-$C_{12}$)-alkylcarbamoyloxy, N—($C_3$-$C_8$)-cycloalkylcarbamoyloxy, N—($C_6$-$C_{12}$)-arylcarbamoyloxy, N—($C_7$-$C_{16}$)-aralkylcarbamoyloxy, N—($C_1$-$C_{10}$)-alkyl-N—($C_6$-$C_{12}$)-arylcarbamoyloxy, N—($C_1$-$C_{10}$)-alkyl-N—($C_7$-$C_{16}$)-aralkylcarbamoyloxy, N—(($C_1$-$C_{10}$)-alkyl)-carbamoyloxy, N—($C_1$-$C_{10}$)-alkyl-N—(($C_7$-$C_{16}$)-aralkyloxy-($C_1$-$C_{10}$)-alkyl)-carbamoyloxyamino, ($C_1$-$C_{12}$)-alkylamino, di-($C_1$-$C_{12}$)-alkylamino, ($C_3$-$C_8$)-cycloalkylamino, ($C_3$-$C_{12}$)-alkenylamino, ($C_3$-$C_2$)-alkynylamino, N—($C_6$-$C_{12}$)-arylamino, N—($C_7$-$C_{11}$)-aralkylamino, N-alkyl-aralkylamino, N-alkyl-arylamino, ($C_1$-$C_{12}$)-alkoxyamino, ($C_1$-$C_{12}$)-alkoxy-N—($C_1$-$C_{10}$)-alkylamino, ($C_1$-$C_{12}$)-alkanoylamino, ($C_3$-$C_8$)-cycloalkanoylamino, ($C_6$-$C_{12}$)-aroylamino, ($C_7$-$C_{16}$)-aralkanoylamino, ($C_1$-$C_{12}$)-alkanoyl-N—($C_1$-$C_{10}$)-alkylamino, ($C_3$-$C_8$)-cycloalkanoyl-N—($C_1$-$C_{10}$)-alkylamino, ($C_6$-$C_{12}$)-aroyl-N—($C_1$-$C_{10}$)-alkylamino, ($C_7$-$C_{11}$)-aralkanoyl-N—($C_1$-$C_{10}$)-alkylamino, amino-($C_1$-$C_{10}$)-alkyl, ($C_1$-$C_{20}$)-alkylmercapto, ($C_1$-$C_{20}$)-alkylsulfinyl, ($C_1$-$C_{20}$)-alkylsulfonyl, ($C_6$-$C_{12}$)-arylmercapto, ($C_6$-$C_{12}$)-arylsulfinyl, ($C_6$-$C_{12}$)-arylsulfonyl, ($C_7$-$C_{16}$)-aralkylmercapto, ($C_7$-$C_{16}$)-aralkylsulfinyl, ($C_7$-$C_{16}$)-aralkylsulfonyl, sulfamoyl, N—($C_1$-$C_{10}$)-alkylsulfamoyl, N,N-di-($C_1$-$C_{10}$)-alkylsulfamoyl, ($C_3$-$C_8$)-cycloalkylsulfamoyl, N—($C_6$-$C_{12}$)-arylsulfamoyl, N—($C_7$-$C_{16}$)-aralkylsulfamoyl, N—($C_1$-$C_{10}$)-alkyl-N—($C_6$-$C_{12}$)-arylsulfamoyl, N—($C_1$-$C_{10}$)-alkyl-N—($C_7$-$C_{16}$)-aralkylsulfamoyl, ($C_1$-$C_{10}$)-alkylsulfonamido, ($C_7$-$C_{16}$)-aralkylsulfonamido, and N—(($C_1$-$C_{10}$)-alkyl-($C_7$-$C_{16}$)-aralkylsulfonamido; where an aryl radical may be substituted by 1 to 5 substituents selected from hydroxyl, halogen, cyano, trifluoromethyl, nitro, carboxyl, ($C_2$-$C_{16}$)-alkyl, ($C_3$-$C_8$)-cycloalkyl, ($C_3$-$C_8$)-cycloalkoxy, ($C_6$-$C_{12}$)-aryl, ($C_7$-$C_{16}$)-aralkyl, ($C_2$-$C_{16}$)-alkenyl, ($C_2$-$C_{12}$)-alkynyl, ($C_1$-$C_{16}$)-alkoxy, ($C_1$-$C_{16}$)-alkenyloxy, ($C_6$-$C_{12}$)-aryloxy, ($C_7$-$C_{16}$)-aralkyloxy, ($C_1$-$C_8$)-hydroxyalkyl, —O—$[CH_2]_xC_fH_{(2f+1-g)}F_g$, —$OCF_2Cl$, and —$OCF_2$—$CHFCl$;

x is 0 to 3;
f is 1 to 8; and
g is 0 or 1 to (2f+1);
including the physiologically active salts, esters, and prodrugs derived therefrom.

Quinoline-2-carboxamides of Formula Ia include, but are not limited to, N—((3-Hydroxy-6-isopropoxy-quinoline-2-carbonyl)-amino)-acetic acid, N—((6-(1-butyloxy)-3-hydroxyquinolin-2-yl)-carbonyl)-glycine, [(3-hydroxy-6-trifluoromethoxy-quinoline-2-carbonyl)-amino]-acetic acid, [(7-Chloro-3-hydroxy-quinoline-2-carbonyl)-amino]-acetic acid] (Compound H), and [(6-chloro-3-hydroxy-quinoline-2-carbonyl)-amino]-acetic acid.

In certain embodiments, compounds of the invention are isoquinoline-3-carboxamides. In one embodiment, the compound is selected from a compound of the Formula Ib wherein A is —$CR^5R^6$—, and $R^5$ and $R^6$ are each independently selected from the group consisting of hydrogen, ($C_1$-$C_6$)-alkyl, ($C_3$-$C_7$)-cycloalkyl, aryl, or a substituent of the α-carbon atom of an α-amino acid, wherein the amino acid is a natural L-amino acid or its D-isomer;

B is —$CO_2H$ or a $CO_2$-G carboxyl radical, where G is a radical of an alcohol G-OH in which G is selected from the group consisting of ($C_1$-$C_{20}$)-alkyl radical, ($C_3$-$C_8$) cycloalkyl radical, ($C_2$-$C_{20}$)-alkenyl radical, ($C_3$-$C_8$)-cycloalkenyl radical, retinyl radical, ($C_2$-$C_{20}$)-alkynyl radical, ($C_4$-$C_{20}$)-alkenynyl radical;

X is O;

Q is O;

$R^4$ is selected from the group consisting of hydrogen, ($C_1$-$C_{10}$)-alkyl, ($C_2$-$C_{10}$)-alkenyl, ($C_2$-$C_{10}$)-alkynyl, wherein alkenyl or alkynyl contains one or two C≡C multiple bonds; unsubstituted fluoroalkyl radical of the formula —$[CH_2]_x$—$C_fH_{(2f+1-g)}$—$F_g$, aryl, heteroaryl, and ($C_7$-$C_{11}$)-aralkyl;

$R^3$, $R^{16}$, $R^{17}$, $R^{18}$ and $R^{19}$ are identical or different and are selected from the group consisting of hydrogen, hydroxyl, halogen, cyano, trifluoromethyl, nitro, carboxyl; ($C_1$-$C_{20}$)-alkyl, ($C_3$-$C_8$)-cycloalkyl, ($C_3$-$C_8$)-cycloalkoxy, ($C_6$-$C_{12}$)-aryl, ($C_7$-$C_{16}$)-aralkyl, ($C_7$-$C_{16}$)-aralkenyl, ($C_7$-$C_{16}$)-aralkynyl, ($C_2$-$C_{20}$)-alkenyl, ($C_2$-$C_{20}$)-alkynyl, ($C_1$-$C_{20}$)-alkoxy, ($C_2$-$C_{20}$)-alkenyloxy, ($C_2$-$C_{20}$)-alkynyloxy, retinyloxy, ($C_6$-$C_{12}$)-aryloxy, ($C_7$-$C_{16}$)-aralkyloxy, ($C_1$-$C_{16}$)-hydroxyalkyl, —O—$[CH_2]_xC_fH_{(2f+1-g)}F_g$, —$OCF_2Cl$, —$OCF_2$—$CHFCl$, ($C_1$-$C_{20}$)-alkylcarbonyl, ($C_3$-$C_8$)-cycloalkylcarbonyl, ($C_6$-$C_{12}$)-arylcarbonyl, ($C_7$-$C_6$)-aralkylcarbonyl, cinnamoyl, ($C_2$-$C_{20}$)-alkenylcarbonyl, ($C_2$-$C_{20}$)-alkynylcarbonyl, ($C_1$-$C_{20}$)-alkoxycarbonyl, ($C_6$-$C_{12}$)-aryloxycarbonyl, ($C_7$-$C_{16}$)-aralkoxycarbonyl, ($C_3$-$C_8$)-cycloalkoxycarbonyl, ($C_2$-$C_{20}$)-alkenyloxycarbonyl, retinyloxycarbonyl, ($C_2$-$C_{20}$)-alkynyloxycarbonyl, ($C_1$-$C_{12}$)-alkylcarbonyloxy, ($C_3$-$C_8$)-cycloalkylcarbonyloxy, ($C_6$-$C_{12}$)-arylcarbonyloxy, ($C_7$-$C_{16}$)-aralkylcarbonyloxy, cinnamoyloxy, ($C_2$-$C_{12}$)-alkenylcarbonyloxy, ($C_2$-$C_{12}$)-alkynylcarbonyloxy, ($C_1$-$C_{12}$)-alkoxycarbonyloxy, ($C_6$-$C_{12}$)-aryloxycarbonyloxy, ($C_7$-$C_{16}$)-aralkyloxycarbonyloxy, ($C_3$-$C_8$)-cycloalkoxycarbonyloxy, ($C_2$-$C_{12}$)-alkenyloxycarbonyloxy, ($C_2$-$C_{12}$)-alkynyloxycarbonyloxy, carbamoyl, N—($C_1$-$C_{12}$)-alkylcarbamoyl, N,N-di-($C_1$-$C_{12}$)-alkylcarbamoyl, N—($C_3$-$C_8$)-cycloalkylcarbamoyl, N,N-dicyclo-($C_3$-$C_8$)-alkylcarbamoyl, N—($C_1$-$C_{10}$)-alkyl-N—($C_3$-$C_8$)-cycloalkylcarbamoyl, N—(($C_3$-$C_8$)-cycloalkyl-($C_1$-$C_6$)-alkyl)-carbamoyl, N-(+)-dehydroabietylcarbamoyl, N—($C_1$-$C_6$)-alkyl-N-(+)-dehydroabietylcarbamoyl, N—($C_6$-$C_{12}$)-arylcarbamoyl, N—($C_7$-$C_{16}$)-aralkylcarbamoyl, N—($C_1$-$C_{10}$)-alkyl-N—($C_6$-$C_{16}$)-arylcarbamoyl, N—($C_1$-$C_{10}$)-alkyl-N—($C_7$-$C_{16}$)-aralkylcarbamoyl, carbamoyloxy, N—($C_1$-$C_{12}$)-alkylcarbamoyloxy, N,N-di-($C_1$-$C_{12}$)-alkylcarbamoyloxy, N—($C_3$-$C_8$)-cycloalkylcarbamoyloxy, N—($C_6$-$C_{12}$)-arylcarbamoyloxy, N—($C_7$-$C_{16}$)-aralkylcarbamoyloxy, N—($C_1$-$C_{10}$)-alkyl-N—($C_6$-$C_{12}$)-arylcarbamoyloxy, N—($C_1$-$C_{10}$)-alkyl-N—($C_7$-$C_{16}$)-aralkylcarbamoyloxy, N—(($C_1$-$C_{10}$)-alkyl)-carbamoyloxy, N—($C_1$-$C_{10}$)-alkyl-N—(($C_7$-$C_{16}$)-aralkyloxy-($C_1$-$C_{10}$)-alkyl)-carbamoyloxyamino, ($C_1$-$C_{12}$)-alkylamino, di-($C_1$-$C_{12}$)-alkylamino, ($C_3$-$C_8$)-cycloalkylamino, ($C_3$-$C_{12}$)-alkenylamino, ($C_3$-$C_{12}$)-alkynylamino, N—($C_6$-$C_{12}$)-arylamino, N—($C_7$-$C_{11}$)-aralkylamino, N-alkyl-aralkylamino, N-alkyl-arylamino, ($C_1$-$C_{12}$)-alkoxyamino, ($C_1$-$C_{12}$)-alkoxy-N—($C_1$-$C_{10}$)-alkylamino, ($C_1$-$C_{12}$)-alkanoylamino, ($C_3$-$C_8$)-cycloalkanoylamino, ($C_6$-$C_{12}$)-aroylamino, ($C_7$-$C_{16}$)-aralkanoylamino, ($C_1$-$C_2$)-alkanoyl-N—($C_1$-$C_{10}$)-alkylamino, ($C_3$-$C_8$)-cycloalkanoyl-N—($C_1$-$C_{10}$)-alkylamino, ($C_6$-$C_{12}$)-aroyl-N—($C_1$-$C_{10}$)-alkylamino, ($C_7$-$C_{11}$)-aralkanoyl-N—($C_1$-$C_{10}$)-alkylamino, amino-($C_1$-$C_{10}$)-alkyl, ($C_1$-$C_{20}$)-alkylmercapto, ($C_1$-$C_{20}$)-alkylsulfinyl, ($C_1$-$C_{20}$)-alkylsulfonyl, ($C_6$-$C_{12}$)-arylmercapto, ($C_6$-$C_{12}$)-arylsulfinyl, ($C_6$-$C_{12}$)-arylsulfonyl, ($C_7$-$C_{16}$)-aralkylmercapto, ($C_7$-$C_{16}$)-aralkylsulfinyl, ($C_7$-$C_{16}$)-aralkylsulfonyl, sulfamoyl, N—($C_1$-$C_{10}$)-alkylsulfamoyl, N,N-di-($C_1$-$C_{10}$)-alkylsulfamoyl, ($C_3$-$C_8$)-cycloalkylsulfamoyl, N—($C_6$-$C_{12}$)-arylsulfamoyl, N—($C_7$-$C_{16}$)-aralkylsulfamoyl, N—($C_1$-$C_{10}$)-alkyl-N—($C_6$-$C_{12}$)-arylsulfamoyl, N—($C_1$-$C_{10}$)-alkyl-N—($C_7$-$C_{16}$)-aralkylsulfamoyl, ($C_1$-$C_{10}$)-alkylsulfonamido, ($C_7$-$C_{16}$)-aralkylsulfonamido, and N—(($C_1$-$C_{10}$)-alkyl-($C_7$-$C_{16}$)-aralkylsulfonamido; where an aryl radical may be substituted by 1 to 5 substituents selected from hydroxyl, halogen, cyano, trifluoromethyl, nitro, carboxyl, ($C_2$-$C_{16}$)-alkyl, ($C_3$-$C_8$)-cycloalkyl, ($C_3$-$C_8$)-cycloalkoxy, ($C_6$-$C_{12}$)-aryl, ($C_7$-$C_{16}$)-aralkyl, ($C_2$-$C_{16}$)-alkenyl, ($C_2$-$C_{12}$)-alkynyl, ($C_1$-$C_{16}$)-alkoxy, ($C_1$-$C_{16}$)-alkenyloxy, ($C_6$-$C_{12}$)-aryloxy, ($C_7$-$C_{16}$)-aralkyloxy, ($C_1$-$C_8$)-hydroxyalkyl, —O—$[CH_2]_xC_fH_{(2f+1-g)}F_g$, —$OCF_2Cl$, and —$OCF_2$—$CHFCl$;

x is 0 to 3;

f is 1 to 8; and g is 0 or 1 to (2f+1);

including the physiologically active salts, esters, and prodrugs derived therefrom.

In another embodiment, compounds of the invention are isoquinoline-3-carboxamides, such as disclosed in WO 2004/108681, represented by Formula Ie

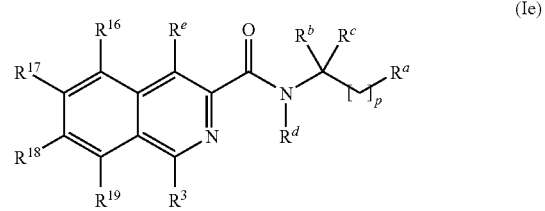

wherein p is zero or one;

$R^a$ is —COOH or —$WR^{50}$; provided that when $R^a$ is —COOH then p is zero and when R' is —$WR^{50}$ then p is one;

W is selected from the group consisting of oxygen, —S(O)$_n$— and —$NR^{51}$— where n is zero, one or two, $R^{51}$ is selected from the group consisting of hydrogen, alkyl, substituted alkyl, acyl, aryl, substituted aryl, heteroaryl, substituted heteroaryl, heterocyclic and substituted heterocyclic and $R^{50}$ is selected from the group consisting of hydrogen, alkyl, substituted alkyl, aryl, substituted aryl, heteroaryl, substituted heteroaryl, heterocyclic and substituted heterocyclic, or when W is —NR$^9$— then R$^{50}$ and R$^{51}$, together with the nitrogen atom to which they are bound, can be joined to form a heterocyclic or a substituted heterocyclic group, provided that when W is —S(O)$_n$— and n is one or two, then R$^{50}$ is not hydrogen;

R$^3$ is selected from the group consisting of hydrogen, alkyl, substituted alkyl, alkoxy, substituted alkoxy, amino, substituted amino, aminoacyl, aryl, substituted aryl, halo, heteroaryl, substituted heteroaryl, heterocyclic, substituted heterocyclic, and —XR$^{60}$ where X is oxygen, —S(O)$_n$— or —NR$^{70}$— where n is zero, one or two; R$^{60}$ is selected from the group consisting of alkyl, substituted alkyl, aryl, substituted aryl, heteroaryl, substituted heteroaryl, heterocyclic and substituted heterocyclic; and R$^{70}$ is hydrogen, alkyl or aryl; or, when X is —NR$^{70}$—, then R$^{60}$ and R$^{70}$, together with the nitrogen atom to which they are bound, can be joined to form a heterocyclic or substituted heterocyclic group;

R$^{17}$ and R$^{18}$ are independently selected from the group consisting of hydrogen, alkyl, substituted alkyl, aryl, substituted aryl, heteroaryl, substituted heteroaryl, halo, hydroxy, cyano, —S(O)$_n$—N(R$^{80}$)—R$^{80}$ where n is 0, 1, or 2, —NR$^{80}$C(O)NR$^{80}$R$^{80}$, —XR$^{80}$ where X is oxygen, —S(O)$_n$— or —NR$^{90}$— where n is zero, one or two, each R$^{80}$ is independently selected from the group consisting of hydrogen, alkyl, substituted alkyl, aryl, substituted aryl, cycloalkyl, substituted cycloalkyl, heteroaryl, substituted heteroaryl, heterocyclic and substituted heterocyclic provided that when X is —SO— or —SO$_2$—, then R$^{80}$ is not hydrogen, and R$^{90}$ is selected from the group consisting of hydrogen, alkyl, aryl, or R$^{17}$, R$^{18}$ together with the carbon atom pendent thereto, form an aryl substituted aryl, heteroaryl, or substituted heteroaryl;

R$^{16}$ and R$^{19}$ are independently selected from the group consisting of hydrogen, halo, alkyl, substituted alkyl, alkoxy, substituted alkoxy, aryl, substituted aryl, heteroaryl, substituted heteroaryl and —XR$^{60}$ where X is oxygen, —S(O)$_n$— or —NR$^{70}$— where n is zero, one or two, R$^{60}$ is selected from the group consisting of alkyl, substituted alkyl, aryl, substituted aryl, heteroaryl, substituted heteroaryl, heterocyclic and substituted heterocyclic, and R$^{70}$ is hydrogen, alkyl or aryl or, when X is —NR$^{70}$—, then R$^{70}$ and R$^{60}$, together with the nitrogen atom to which they are bound, can be joined to form a heterocyclic or substituted heterocyclic group;

R$^b$ is selected from the group consisting of hydrogen, deuterium and methyl;

R$^c$ is selected from the group consisting of hydrogen, deuterium, alkyl and substituted alkyl; alternatively, R$^b$ and R$^c$ and the carbon pendent thereto can be joined to form cycloalkyl, substituted cycloalkyl, heterocyclic or substituted heterocyclic group;

R$^d$ is selected from the group consisting of hydrogen and alkyl or Rd together with Re and the nitrogen pendent thereto can be joined to form a heterocyclic or substituted heterocyclic group; and R$^d$ is selected from the group consisting of hydroxy, alkoxy, substituted alkoxy, acyloxy, cycloalkoxy, substituted cycloalkoxy, aryloxy, substituted aryloxy, heteroaryloxy, substituted heteroaryloxy, aryl, —S(O)$_n$—R$^{95}$ wherein R$^{95}$ is selected from the group consisting of alkyl, substituted alkyl, cycloalkyl, substituted cycloalkyl, aryl, substituted aryl, heteroaryl and substituted heteroaryl and n is zero, one or two;

and pharmaceutically acceptable salts, esters, and prodrugs thereof.

In one embodiment, the compounds of Formula Ie are represented by Formula Ie(i)

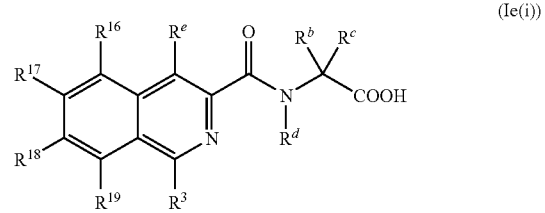

wherein R$^3$, R$^{16}$, R$^{17}$, R$^{18}$, R$^{19}$, R$^b$, R$^c$, R$^d$, and R$^e$ are as defined above in the discussion for Formula Ie; and pharmaceutically acceptable salts, esters, and prodrugs thereof.

In particular embodiments, the invention is directed to compounds of Formula Ie(i) wherein R$^3$ is selected from the group consisting of hydrogen, alkyl, substituted alkyl, alkoxy, substituted alkoxy, aryl, substituted aryl, halo, heteroaryl, substituted heteroaryl, heterocyclic, substituted heterocyclic, and —XR$^{60}$ where X is oxygen, —S(O)$_n$— or —NR$^{70}$— where n is zero, one or two, R$^{60}$ is selected from the group consisting of alkyl, substituted alkyl, aryl, substituted aryl, heteroaryl, substituted heteroaryl, heterocyclic and substituted heterocyclic, and R$^{70}$ is hydrogen, alkyl or aryl;

R$^{17}$ and R$^{18}$ are independently selected from the group consisting of hydrogen, alkyl, substituted alkyl, alkoxy, substituted alkoxy, aryl, substituted aryl, heteroaryl, substituted heteroaryl, halo, hydroxy, cyano, —XR$^{80}$ where X is oxygen, —S(O)$_n$— or —NR$^{90}$— where n is zero, one or two, R$^{80}$ is selected from the group consisting of alkyl, substituted alkyl, aryl, substituted aryl, heteroaryl, substituted heteroaryl, heterocyclic and substituted heterocyclic, and R$^{90}$ is hydrogen, alkyl or aryl;

R$^{16}$ and R$^{19}$ are independently selected from the group consisting of hydrogen, halo, alkyl, substituted alkyl, alkoxy, substituted alkoxy, aryl, substituted aryl, heteroaryl, substituted heteroaryl and —XR$^{60}$ where X is oxygen, —S(O)$_n$— or —NR$^{70}$— where n is zero, one or two, R$^{60}$ is selected from the group consisting of alkyl, substituted alkyl, aryl, substituted aryl, heteroaryl, substituted heteroaryl, heterocyclic and substituted heterocyclic, and R$^{70}$ is hydrogen, alkyl or aryl;

R$^b$ is selected from the group consisting of hydrogen and methyl;

R$^c$ is selected from the group consisting of alkyl and substituted alkyl; or R$^a$ and R$^b$ may be joined to form a cycloalkyl, substituted cycloalkyl, heterocyclic or substituted heterocyclic; and R$^d$ is selected from the group consisting of hydrogen and alkyl or R$^d$ together with R$^c$ and the nitrogen pendent thereto forms a heterocyclic or substituted heterocyclic group; and R$^e$ is hydroxy;

and pharmaceutically acceptable salts, esters, and prodrugs thereof.

In another embodiment, the compounds of Formula Ie are represented by the Formula Ie(ii)

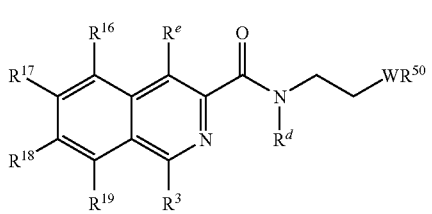

(Ie(ii))

wherein $R^3$, $R^{16}$, $R^{17}$, $R^{18}$, $R^{19}$, $R^d$, $R^e$, and $WR^{50}$ are as defined above in the discussion for Formula Ie; and pharmaceutically acceptable salts, esters, and prodrugs thereof.

In particular embodiments, the invention is directed to compounds of Formula Ie(ii) wherein
W is selected from the group consisting of oxygen, —S(O)$_n$— and —NR$^{51}$— where n is zero, one or two, $R^{51}$ is selected from the group consisting of hydrogen, alkyl, substituted alkyl, acyl, aryl, substituted aryl, heteroaryl, substituted heteroaryl, heterocyclic and substituted heterocyclic;
$R^{50}$ is selected from the group consisting of hydrogen, alkyl, substituted alkyl, aryl, substituted aryl, heteroaryl, substituted heteroaryl, heterocyclic and substituted heterocyclic;
$R^d$ is selected from hydrogen and alkyl;
$R^e$ is hydroxy;
$R^{17}$ and $R^{18}$ are independently selected from the group consisting of hydrogen, alkyl, substituted alkyl, alkoxy, substituted alkoxy, aryl, substituted aryl, heteroaryl, substituted heteroaryl, halo, hydroxy, cyano, —XR$^{80}$ where X is oxygen, —S(O)$_n$— or —NR$^{90}$— where n is zero, one or two, $R^{80}$ is selected from the group consisting of alkyl, substituted alkyl, aryl, substituted aryl, heteroaryl, substituted heteroaryl, heterocyclic and substituted heterocyclic, and $R^{90}$ is hydrogen, alkyl or aryl; and
$R^{16}$ and $R^{19}$ are independently selected from the group consisting of hydrogen, halo, alkyl, substituted alkyl, alkoxy, substituted alkoxy, aryl, substituted aryl, heteroaryl, substituted heteroaryl and —XR$^{60}$ where X is oxygen, —S(O)$_n$— or —NR$^{70}$— where n is zero, one or two, $R^{60}$ is selected from the group consisting of alkyl, substituted alkyl, aryl, substituted aryl, heteroaryl, substituted heteroaryl, heterocyclic and substituted heterocyclic, and $R^{70}$ is hydrogen, alkyl or aryl;
and pharmaceutically acceptable salts, esters, and prodrugs thereof.

In another embodiment, the compounds of Formula Ie are represented by the Formula Ie(iii)

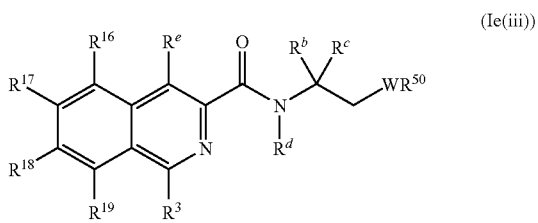

(Ie(iii))

wherein $R^3$, $R^{16}$, $R^{17}$, $R^{18}$, $R^{19}$, $R^b$, $R^c$, $R^d$, $R^e$, and $WR^{50}$ are as defined above in the discussion for Formula Ie; and pharmaceutically acceptable salts, esters, and prodrugs thereof.

In particular embodiments, the invention is directed to compounds of Formula Ie(iii) wherein
W is selected from the group consisting of oxygen, —S(O)$_n$— and —NR$^{51}$— where n is zero, one or two, $R^{51}$ is selected from the group consisting of hydrogen, alkyl, substituted alkyl, aryl, substituted aryl, heteroaryl, substituted heteroaryl, heterocyclic and substituted heterocyclic;
$R^{50}$ is selected from the group consisting of hydrogen, alkyl, substituted alkyl, aryl, substituted aryl, heteroaryl, substituted heteroaryl, heterocyclic and substituted heterocyclic;
$R^3$ is selected from the group consisting of hydrogen, alkyl, substituted alkyl, alkoxy, substituted alkoxy, aryl, substituted aryl, halo, heteroaryl, substituted heteroaryl, heterocyclic, substituted heterocyclic, and —XR$^{60}$ where X is oxygen, —S(O)$_n$— or —NR$^{70}$— where n is zero, one or two, $R^{60}$ is selected from the group consisting of alkyl, substituted alkyl, aryl, substituted aryl, heteroaryl, substituted heteroaryl, heterocyclic and substituted heterocyclic, and $R^{70}$ is hydrogen, alkyl, or aryl;
$R^{17}$ and $R^{18}$ are independently selected from the group consisting of hydrogen, alkyl, substituted alkyl, alkoxy, substituted alkoxy, aryl, substituted aryl, heteroaryl, substituted heteroaryl, halo, hydroxy, cyano, —XR$^{80}$ where X is oxygen, —S(O)$_n$— or —NR$^{90}$— where n is zero, one or two, $R^{80}$ is selected from the group consisting of alkyl, substituted alkyl, aryl, substituted aryl, heteroaryl, substituted heteroaryl, heterocyclic and substituted heterocyclic, and $R^{90}$ is hydrogen, alkyl, or aryl;
$R^{16}$ and $R^{19}$ are independently selected from the group consisting of hydrogen, halo, alkyl, substituted alkyl, alkoxy, substituted alkoxy, aryl, substituted aryl, heteroaryl, substituted heteroaryl and —XR$^{60}$ where X is oxygen, —S(O)$_n$— or —NR$^{70}$ where n is zero, one or two, $R^{60}$ is selected from the group consisting of alkyl, substituted alkyl, aryl, substituted aryl, heteroaryl, substituted heteroaryl, heterocyclic and substituted heterocyclic, and $R^{70}$ is hydrogen, alkyl, or aryl;
$R^b$ is selected from the group consisting of hydrogen and methyl;
$R^c$ is selected from the group consisting of alkyl and substituted alkyl; or $R^b$ and $R^c$ can be joined to form cycloalkyl, substituted cycloalkyl, heterocyclic or substituted heterocyclic
$R^d$ is selected from the group consisting of hydrogen and alkyl or $R^d$ together with $R^c$ and the nitrogen pendent thereto forms a heterocyclic or substituted heterocyclic group; and
$R^e$ is hydroxy;
and pharmaceutically acceptable salts, esters, and prodrugs thereof.

In another embodiment, the compounds of Formula Ie are represented by the Formula Ie(iv)

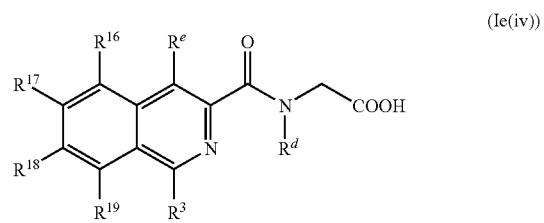

(Ie(iv))

wherein $R^3$, $R^6$, $R^{27}$, $R^{18}$, $R^{19}$, Rd, and Re are as defined above in the discussion for Formula Ie; and pharmaceutically acceptable salts, esters, and prodrugs thereof.

In one particular embodiment, the invention is directed to compounds of Formula Ie(iv) wherein $R^d$ is selected from hydrogen and alkyl;

$R^e$ is hydroxy;

$R^3$ is selected from the group consisting of hydrogen, alkyl, substituted alkyl, alkoxy, substituted alkoxy, aryl, substituted aryl, halo, heteroaryl, substituted heteroaryl, heterocyclic, substituted heterocyclic, and —$XR^{60}$ where X is oxygen, —$S(O)_n$— or —$NR^{70}$— where n is zero, one or two, $R^{60}$ is selected from the group consisting of alkyl, substituted alkyl, aryl, substituted aryl, heteroaryl, substituted heteroaryl, heterocyclic and substituted heterocyclic, and $R^{70}$ is hydrogen, alkyl or aryl;

$R^{17}$ and $R^{18}$ are independently selected from the group consisting of hydrogen, alkyl, substituted alkyl, aryl, substituted aryl, heteroaryl, substituted heteroaryl, halo, hydroxy, cyano, —$XR^{80}$ where X is oxygen, —$S(O)_n$— or —$NR^{90}$— where n is zero, one or two, $R^{80}$ is selected from the group consisting of alkyl, substituted alkyl, aryl, substituted aryl, heteroaryl, substituted heteroaryl, heterocyclic and substituted heterocyclic, and $R^{90}$ is hydrogen, alkyl or aryl; and $R^{16}$ and $R^{19}$ are independently selected from the group consisting of hydrogen, halo, alkyl, substituted alkyl, alkoxy, substituted alkoxy, aryl, substituted aryl, heteroaryl, substituted heteroaryl and —$XR^{60}$ where X is oxygen, —$S(O)_n$— or —$NR^{70}$— where n is zero, one or two, $R^{60}$ is selected from the group consisting of alkyl, substituted alkyl, aryl, substituted aryl, heteroaryl, substituted heteroaryl, heterocyclic and substituted heterocyclic, and $R^{70}$ is hydrogen, alkyl or aryl;

and pharmaceutically acceptable salts, esters, and prodrugs thereof.

In certain embodiments of compounds of Formula Ie including, but not limited to, certain compounds of Formulae Ie(i), Ie(ii), Ie(iii), and Ie(iv), $R^3$ is selected from the group consisting of hydrogen, alkyl, substituted alkyl, halo, alkoxy, aryloxy, substituted aryloxy, substituted aryl, alkylthio, aminoacyl, aryl, substituted amino, heteroaryl, heteroaryloxy, —$S(O)_n$-aryl, —$S(O)_n$-substituted aryl, —$S(O)_n$-heteroaryl, and —$S(O)_n$-substituted heteroaryl, where n is zero, one or two. In particular embodiments, $R^3$ is selected from the group consisting of (3-methoxyphenyl)sulfanyl; (4-chlorophenyl)sulfanyl; (4-methylphenyl)sulfanyl; 2-fluorophenoxy; 2-methoxyphenoxy; (2-methoxyphenyl)sulfanyl 3-fluorophenoxy; 3-methoxyphenoxy; 4-(methylcarbonylamino)phenoxy; 4-(methylsulfonamido)phenoxy; 4-fluorophenoxy; 4-methoxyphenoxy; 4-methoxyphenylsulfanyl; 4-methylphenyl; bromo; chloro; dimethylaminomethyl; ethoxy; ethylsulfanyl; hydrogen; isopropyl; methoxy; methoxymethyl; methyl; N,N-dimethylaminocarbonyl; naphth-2-yloxy; naphthylsulfanyl; phenoxy; phenyl; phenylamino; phenylsulfinyl; phenylsulfanyl; pyridin-2-yloxy; pyridin-2-yl; and pyridin-2-ylsulfanyl.

In certain embodiments of compounds of Formula Ie including, but not limited to, certain compounds of Formulae Ie(i), Ie(ii), Ie(iii), and Ie(iv), $R^{16}$ is hydrogen or phenyl.

In certain embodiments of compounds of Formula Ie including, but not limited to, certain compounds of Formulae Ie(i), Ie(ii), Ie(iii), and Ie(iv), $R^{17}$ is selected from the group consisting of: substituted aryloxy, substituted alkoxy, alkoxy, substituted alkyl, alkyl, amino, cycloalkyloxy, hydrogen, halo, aryl, —$S(O)_n$-aryl, —$S(O)_n$-substituted aryl, —$S(O)_n$-heteroaryl, and —$S(O)_n$-substituted heteroaryl, where n is zero, one or two, aminocarbonylamino, and heteroaryloxy. In particular embodiments, $R^{17}$ is selected from the group consisting of amino; (4-methyl)phenyl-sulfonylaminophenoxy; 3,4-difluorophenoxy; 3,5-difluorophenoxy; 3-fluoro-5-methoxy-phenoxy; 3-chloro-4-fluorophenoxy 4-$CF_3$—O-phenoxy; 4-$CF_3$-phenoxy; 4-chlorophenoxy; 4-fluorophenoxy; 4-(4-fluorophenoxy)phenoxy; 4-methoxyphenoxy; benzyloxy; bromo; butoxy; $CF_3$; chloro; cyclohexyloxy; hydrogen; iodo; isopropoxy; phenoxy; phenyl; phenylsulfanyl; phenylsulfonyl; phenylsulfinyl; phenylurea; pyridin-1-ylsulfanyl; pyridin-3-yloxy; and pyridin-4-ylsulfanyl.

In certain embodiments of compounds of Formula Ie including, but not limited to, certain compounds of Formulae Ie(i), Ie(ii), Ie(iii), and Ie(iv), $R^{18}$ is selected from the group consisting of substituted amino, aryloxy, substituted aryloxy, alkoxy, substituted alkoxy, halo, hydrogen, alkyl, substituted alkyl, aryl, —$S(O)_n$-aryl, —$S(O)_n$-substituted aryl, —$S(O)_n$-cycloalkyl, where n is zero, one or two, aminocarbonylamino, heteroaryloxy, and cycloalkyloxy. In particular embodiments, $R^{18}$ is selected from the group consisting of (4-methoxy)phenylsulfonylamino; 2,6-dimethylphenoxy; 3,4-difluorophenoxy; 3,5-difluorophenoxy; 3-chloro-4-fluorophenoxy; 3-methoxy-4-fluorophenoxy; 3-methoxy-5-fluorophenoxy; 4-(methylsulfonamido)phenoxy; 4-(phenylsulfonamido)phenoxy; 4-$CF_3$—O-phenoxy; 4-$CF_3$-phenoxy; 4-chlorophenoxy; 4-fluorophenoxy; 4-(4-fluorophenoxy)phenoxy; 4-methoxyphenoxy; 4-nitrophenoxy; benzyloxy; bromo; butoxy; $CF_3$; chloro; cyclohexyloxy; cyclohexylsulfanyl; cyclohexylsulfonyl; fluoro; hydrogen; iodo; isopropoxy; methyl; phenoxy; phenyl; phenylsulfanyl; phenylsulfinyl; phenylsulfonyl; phenylurea; pyridin-1-ylsulfanyl; pyridin-3-yloxy; and pyridin-4-ylsulfanyl.

Alternatively, $R^{17}$ and $R^{18}$, combined with the carbon atoms pendent thereto, are joined to form an aryl group. In a particular embodiment, the aryl group is phenyl.

In certain embodiments of compounds of Formula Ie including, but not limited to, certain compounds of Formulae Ie(i), Ie(ii), Ie(iii), and Ie(iv), $R^{19}$ is selected from the group consisting of: substituted arylthio, halo, hydrogen, substituted alkyl and aryl. In particular embodiments, $R^{19}$ is selected from the group consisting of 4-chlorophenyl sulfanyl; chloro; hydrogen; methoxymethyl; and phenyl.

In certain embodiments of compounds of Formulae Ie, including but not limited to, certain compounds of Formulae Ie(i) and Ie(iii), $R^b$ is selected from the group consisting of hydrogen, deuterium, aryl and alkyl. In particular embodiments, $R^b$ is selected from the group consisting of phenyl, hydrogen, deuterium and methyl.

In certain embodiments of compounds of Formula Ie including, but not limited to certain compounds of Formulae Ie(i) and Ie(iii), $R^c$ is selected from the group consisting of preferably hydrogen, deuterium, alkyl, substituted alkyl, and substituted amino. In particular embodiments, $R^c$ is selected from the group consisting of 4-aminobutyl; 4-hydroxybenzyl; benzyl; carboxylmethyl; deuterium; hydroxymethyl; imidazol-4-ylmethyl; isopropyl; methyl; and propyl.

Alternatively, $R^b$, $R^c$, and the carbon atom pendent thereto join to form a cycloalkyl and more preferably cyclopropyl.

In certain embodiments of compounds of Formula Ie including, but not limited to, certain compounds of Formulae Ie(i) and Ie(iii), $R^d$ is hydrogen, alkyl or substituted alkyl. In particular embodiments, $R^d$ is hydrogen, methyl or carboxylmethyl (—$CH_2C(O)OH$). Alternatively, $R^c$, $R^d$, and the carbon atom and nitrogen atom respectively pendent thereto join to form a heterocyclic group and more preferably pyrrolidinyl.

In certain embodiments of compounds of Formula Ie including, but not limited to, certain compounds of Formulae Ie(i), Ie(ii), Ie(iii) and Ie(iv), $R^e$ is selected from the group consisting of hydrogen, hydroxy, alkoxy, substituted alkoxy, cycloalkoxy, substituted cycloalkoxy, thiol, acyloxy and aryl. In particular embodiments, Re is selected from the group consisting of hydroxy; benzyloxy; ethoxy; thiol; methoxy; methylcarbonyloxy; and phenyl.

In certain embodiments of compounds of Formulae Ie including, but not limited to, certain compounds of Formulae Ie(ii) and Ie(iii), $WR^{50}$ is selected from the group consisting of amino, substituted amino, aminoacyl, hydroxy, and alkoxy. In particular embodiments, $WR^{50}$ is selected from the group consisting of amino; dimethylamino; hydroxy; methoxy; and methylcarbonylamino.

Isoquinoline-3-carboxamides of Formula Ib and Formula Ie include, but are not limited to, N—((1-chloro-4-hydroxy-7-(2-propyloxy) isoquinolin-3-yl)-carbonyl)-glycine, N—((1-chloro-4-hydroxy-6-(2-propyloxy) isoquinolin-3-yl)-carbonyl)-glycine, N—((1-chloro-4-hydroxy-isoquinoline-3-carbonyl)-amino)-acetic acid (Compound A), [[(1-chloro-4-hydroxy-7-methoxy-isoquinoline-3-carbonyl)-amino]-acetic acid] (Compound I), N—((1-chloro-4-hydroxy-6-methoxyisoquinolin-3-yl)-carbonyl)-glycine, N—((7-butyloxy)-1-chloro-4-hydroxyisoquinolin-3-yl)-carbonyl)-glycine, N—((6-benzyloxy-1-chloro-4-hydroxy-isoquinoline-3-carbonyl)-amino)-acetic acid, ((7-benzyloxy-1-chloro-4-hydroxy-isoquinoline-3-carbonyl)-amino)-acetic acid methyl ester, N—((7-benzyloxy-1-chloro-4-hydroxy-isoquinoline-3-carbonyl)-amino)-acetic acid, N—((8-chloro-4-hydroxyisoquinolin-3-yl)-carbonyl)-glycine, N—((7-butoxy-4-hydroxy-isoquinoline-3-carbonyl)-amino)-acetic acid, [(1,7-dichloro-4-hydroxy-isoquinoline-3-carbonyl)-amino]-acetic acid, [[(6,7-dichloro-4-hydroxy-isoquinoline-3-carbonyl)-amino]-acetic acid] (compound J), {[4-hydroxy-1-(naphthalen-2-yloxy)-isoquinoline-3-carbonyl]-amino}-acetic acid, {[4-hydroxy-1-(4-methoxy-phenoxy)-isoquinoline-3-carbonyl]-amino}-acetic acid, {[4-hydroxy-1-(3-methoxy-phenoxy)-isoquinoline-3-carbonyl]-amino}-acetic acid, {[1-(3-fluoro-phenoxy)-4-hydroxy-isoquinoline-3-carbonyl]-amino}-acetic acid, {[1-(4-fluoro-phenoxy)-4-hydroxy-isoquinoline-3-carbonyl]-amino}-acetic acid, {[1-(2-fluoro-phenoxy)-4-hydroxy-isoquinoline-3-carbonyl]-amino}-acetic acid, {[4-hydroxy-1-(2-methoxy-phenoxy)-isoquinoline-3-carbonyl]-amino}-acetic acid, [(4-hydroxy-1-phenylamino-isoquinoline-3-carbonyl)-amino]-acetic acid, [(1-chloro-4-methoxy-isoquinoline-3-carbonyl)-amino]-acetic acid, [(1-chloro-4-ethoxy-isoquinoline-3-carbonyl)-amino]-acetic acid, [(4-hydroxy-1-methoxy-isoquinoline-3-carbonyl)-amino]-acetic acid, [(1-ethoxy-4-hydroxy-isoquinoline-3-carbonyl)-amino]-acetic acid, [(4-hydroxy-1-phenyl-isoquinoline-3-carbonyl)-amino]-acetic acid, [(4-hydroxy-1-methyl-isoquinoline-3-carbonyl)-amino]-acetic acid, [(4-hydroxy-1-methoxymethyl-isoquinoline-3-carbonyl)-amino]-acetic acid, [(1-dimethylcarbamoyl-4-hydroxy-isoquinoline-3-carbonyl)-amino]-acetic acid, [(4-hydroxy-1-methyl-6-phenoxy-isoquinoline-3-carbonyl)-amino]-acetic acid, [(4-hydroxy-1-methyl-7-phenoxy-isoquinoline-3-carbonyl)-amino]-acetic acid (Compound D), [(4-benzyloxy-1-methyl-7-phenoxy-isoquinoline-3-carbonyl)-amino]-acetic acid, [(4-ethoxy-1-methyl-7-phenoxy-isoquinoline-3-carbonyl)-amino]-acetic acid, [(1-dimethylcarbamoyl-4-hydroxy-7-phenoxy-isoquinoline-3-carbonyl)-amino]-acetic acid, [(4-hydroxy-1-methoxymethyl-7-phenoxy-isoquinoline-3-carbonyl)-amino]-acetic acid, [(4-hydroxy-1-p-tolyl-isoquinoline-3-carbonyl)-amino]-acetic acid, {[7-(4-fluoro-phenoxy)-4-hydroxy-1-methyl-isoquinoline-3-carbonyl]-amino}-acetic acid, {[1-chloro-4-hydroxy-7-(4-methoxy-phenoxy)-isoquinoline-3-carbonyl]-amino}-acetic acid, {[4-hydroxy-7-(4-methoxy-phenoxy)-isoquinoline-3-carbonyl]-amino}-acetic acid (Compound C), {[1-chloro-4-hydroxy-6-(4-methoxy-phenoxy)-isoquinoline-3-carbonyl]-amino}-acetic acid, {[4-hydroxy-6-(4-methoxy-phenoxy)-isoquinoline-3-carbonyl]-amino}-acetic acid, {[1-chloro-4-hydroxy-7-(4-trifluoromethyl-phenoxy)-isoquinoline-3-carbonyl]-amino}-acetic acid, {[4-hydroxy-7-(4-trifluoromethyl-phenoxy)-isoquinoline-3-carbonyl]-amino}-acetic acid, {[1-chloro-4-hydroxy-6-(4-trifluoromethyl-phenoxy)-isoquinoline-3-carbonyl]-amino}-acetic acid, {[4-hydroxy-6-(4-trifluoromethyl-phenoxy)-isoquinoline-3-carbonyl]-amino}-acetic acid, {[1-chloro-7-(4-fluoro-phenoxy)-4-hydroxy-isoquinoline-3-carbonyl]-amino}-acetic acid, {[7-(4-fluoro-phenoxy)-4-hydroxy-isoquinoline-3-carbonyl]-amino}-acetic acid (Compound E), {[1-chloro-6-(4-fluoro-phenoxy)-4-hydroxy-isoquinoline-3-carbonyl]-amino}-acetic acid, {[6-(4-fluoro-phenoxy)-4-hydroxy-isoquinoline-3-carbonyl]-amino}-acetic acid, [(7-benzenesulfinyl-4-hydroxy-isoquinoline-3-carbonyl)-amino]-acetic acid, [(7-benzenesulfonyl-4-hydroxy-isoquinoline-3-carbonyl)-amino]-acetic acid, [(6-benzenesulfinyl-4-hydroxy-isoquinoline-3-carbonyl)-amino]-acetic acid, [(6-benzenesulfonyl-4-hydroxy-isoquinoline-3-carbonyl)-amino]-acetic acid, {[4-hydroxy-7-(4-methoxy-benzenesulfonylamino)-isoquinoline-3-carbonyl]-amino}-acetic acid, [(4-hydroxy-1-phenylsulfanyl-isoquinoline-3-carbonyl)-amino]-acetic acid, {[1-(4-chloro-phenylsulfanyl)-4-hydroxy-isoquinoline-3-carbonyl]-amino}-acetic acid, [(4-hydroxy-1-p-tolylsulfanyl-isoquinoline-3-carbonyl)-amino]-acetic acid, {[4-hydroxy-1-(3-methoxy-phenylsulfanyl)-isoquinoline-3-carbonyl]-amino}-acetic acid, {[4-hydroxy-1-(2-methoxy-phenylsulfanyl)-isoquinoline-3-carbonyl]-amino}-acetic acid, {[4-hydroxy-1-(naphthalen-2-ylsulfanyl)-isoquinoline-3-carbonyl]-amino}-acetic acid, [(1-benzenesulfinyl-4-hydroxy-isoquinoline-3-carbonyl)-amino]-acetic acid, [(1-benzenesulfonyl-4-hydroxy-isoquinoline-3-carbonyl)-amino]-acetic acid, [(1-chloro-4-hydroxy-6,7-diphenoxy-isoquinoline-3-carbonyl)-amino]-acetic acid, [[(4-Hydroxy-1,7-diphenoxy-isoquinoline-3-carbonyl)-amino]-acetic acid] (Compound M), [(4-hydroxy-6,7-diphenoxy-isoquinoline-3-carbonyl)-amino]-acetic acid, {[4-hydroxy-7-(4-nitro-phenoxy)-isoquinoline-3-carbonyl]-amino}-acetic acid, [(4-mercapto-7-phenoxy-isoquinoline-3-carbonyl)-amino]-acetic acid, [(4-mercapto-7-trifluoromethyl-isoquinoline-3-carbonyl)-amino]-acetic acid, {[7-(4-chloro-phenoxy)-4-hydroxy-isoquinoline-3-carbonyl]-amino}-acetic acid, {[6-(4-chloro-phenoxy)-4-hydroxy-isoquinoline-3-carbonyl]-amino}-acetic acid, {[6-(3-fluoro-5-methoxy-phenoxy)-4-hydroxy-isoquinoline-3-carbonyl]-amino}-acetic acid, {[7-(3-fluoro-5-methoxy-phenoxy)-4-hydroxy-isoquinoline-3-carbonyl]-amino}-acetic acid, {[7-(3,4-difluoro-phenoxy)-4-hydroxy-isoquinoline-3-carbonyl]-amino}-acetic acid, {[6-(3,4-difluoro-phenoxy)-4-hydroxy-isoquinoline-3-carbonyl]-amino}-acetic acid, {[4-hydroxy-7-(4-trifluoromethoxy-phenoxy)-isoquinoline-3-carbonyl]-amino}-acetic acid, {[4-hydroxy-6-(4-trifluoromethoxy-phenoxy)-isoquinoline-3-carbonyl]-amino}-acetic acid, 2-(S)-{[7-(4-chloro-phenoxy)-4-hydroxy-isoquinoline-3-carbonyl]-amino}-propionic acid, 2-(S)-{[6-(4-chloro-phenoxy)-4-hydroxy-isoquinoline-3-carbonyl]-amino}-propionic acid, 2-{[7-(3,4-difluoro-phenoxy)-4-hydroxy-isoquinoline-3-carbonyl]-amino}-propionic acid, 2-(S)-[(4-hydroxy-7-phenylsulfanyl-isoquinoline-3-carbonyl)-amino]-propionic acid (Compound L), 2-(R)-[(4-hydroxy-7-phenylsulfanyl-isoquinoline-3-carbonyl)-amino]-propionic acid, 2-(R)-[(4-hydroxy-7-phenoxy-isoquinoline-3-carbonyl)-amino]-propionic acid, (S)-2-[(4-Hydroxy-7-phenoxy-isoquinoline-3-carbonyl)-amino]-propionic acid (Compound B), 2-(S)-{[4-hydroxy-7-(4-methoxy-phenoxy)-isoquinoline-3-carbonyl]-amino}-propionic acid, 2-(S)-[(7-benzenesulfonyl-4-hydroxy-isoquinoline-3-carbonyl)-amino]-propionic acid, (R)-2-[(4-hydroxy-1-methoxymethyl-7-phenoxy-isoquinoline-3-carbonyl)-amino]-propionic acid, (S)-2-[(4-hydroxy-1-methoxymethyl-7-phenoxy-isoquinoline-3-carbonyl)-amino]-propionic acid, (S)-2-[(4-mercapto-7-phenoxy-isoquinoline-3-carbonyl)-amino]-propionic acid, (S)-2-{[1-(4-chloro-phenylsulfanyl)-4-hydroxy-isoquinoline-3-carbonyl]-amino}-propionic acid, (R)-2-{[1-(4-chloro-phenylsulfanyl)-4-hydroxy-isoquinoline-3-carbonyl]-amino}-propionic acid, [(4-hydroxy-7-phenylsulfanyl-isoquinoline-3-carbonyl)-amino]-acetic acid (Compound N), [(4-hydroxy-6-phenylsulfanyl-isoquinoline-3-carbonyl)-amino]-acetic acid, [(1-chloro-4-hydroxy-7-phenylsulfanyl-isoquinoline-3-carbonyl)-amino]-acetic acid, [(1-chloro-4-hydroxy-6-phenylsulfanyl-isoquinoline-3-carbonyl)-amino]-acetic acid, [(1-bromo-4-hydroxy-7-phenylsulfanyl-isoquinoline-3-carbonyl)-amino]-acetic acid, [(1-bromo-4-hydroxy-6-phenylsulfanyl-isoquinoline-3-carbonyl)-amino]-acetic acid, [(4-hydroxy-7-phenoxy-isoquinoline-3-carbonyl)-amino]-acetic acid (Compound K), [(4-hydroxy-6-phenoxy-isoquinoline-3-carbonyl)-amino]-acetic acid, [(1-chloro-4-hydroxy-7-phenoxy-isoquinoline-3-carbonyl)-amino]-acetic acid, [(1-chloro-4-hydroxy-6-phenoxy-isoquinoline-3-carbonyl)-amino]-acetic acid, [(1-bromo-4-hydroxy-7-phenoxy-isoquinoline-3-carbonyl)-amino]-acetic acid, [(1-bromo-4-hydroxy-6-phenoxy-isoquinoline-3-carbonyl)-amino]-acetic acid, {[7-(2,6-dimethyl-phenoxy)-4-hydroxy-isoquinoline-3-carbonyl]-amino}-acetic acid, {[1-chloro-7-(2,6-dimethyl-phenoxy)-4-hydroxy-isoquinoline-3-carbonyl]-amino}-acetic acid, {[1-bromo-7-(2,6-dimethyl-phenoxy)-4-hydroxy-isoquinoline-3-carbonyl]-amino}-acetic acid, [(1-bromo-7-chloro-4-hydroxy-isoquinoline-3-carbonyl)-amino]-acetic acid, [(1-bromo-6-chloro-4-hydroxy-isoquinoline-3-carbonyl)-amino]-acetic acid, [(1-bromo-4-hydroxy-7-trifluoromethyl-isoquinoline-3-carbonyl)-amino]-acetic acid, [(1-bromo-4-hydroxy-6-trifluoromethyl-isoquinoline-3-carbonyl)-amino]-acetic acid, [(4-hydroxy-1-phenoxy-isoquinoline-3-carbonyl)-amino]-acetic acid, [(1,7-dibromo-4-hydroxy-isoquinoline-3-carbonyl)-amino]-acetic acid, [(7-bromo-1-chloro-4-hydroxy-isoquinoline-3-carbonyl)-amino]-acetic acid, [(6-bromo-4-hydroxy-isoquinoline-3-carbonyl)-amino]-acetic acid, [(1-bromo-7-fluoro-4-hydroxy-isoquinoline-3-carbonyl)-amino]-acetic acid, [(7-fluoro-4-hydroxy-isoquinoline-3-carbonyl)-amino]-acetic acid, [(1-chloro-7-fluoro-4-hydroxy-isoquinoline-3-carbonyl)-amino]-acetic acid, [(1-bromo-4-hydroxy-isoquinoline-3-carbonyl)-amino]-acetic acid, [(4-hydroxy-6-phenyl-isoquinoline-3-carbonyl)-amino]-acetic acid, [(4-hydroxy-7-phenyl-isoquinoline-3-carbonyl)-amino]-acetic acid, [(1-chloro-4-hydroxy-6-phenyl-isoquinoline-3-carbonyl)-amino]-acetic acid, [(1-chloro-4-hydroxy-7-phenyl-isoquinoline-3-carbonyl)-amino]-acetic acid, [(1-bromo-4-hydroxy-6-phenyl-isoquinoline-3-carbonyl)-amino]-acetic acid, [(1-bromo-4-hydroxy-7-phenyl-isoquinoline-3-carbonyl)-amino]-acetic acid, [(4-hydroxy-5-phenyl-isoquinoline-3-carbonyl)-amino]-acetic acid, [(4-hydroxy-8-phenyl-isoquinoline-3-carbonyl)-amino]-acetic acid, [(1-chloro-4-hydroxy-5-phenyl-isoquinoline-3-carbonyl)-amino]-acetic acid, [(1-chloro-4-hydroxy-8-phenyl-isoquinoline-3-carbonyl)-amino]-acetic acid, [(1-bromo-4-hydroxy-5-phenyl-isoquinoline-3-carbonyl)-amino]-acetic acid, [(1-bromo-4-hydroxy-8-phenyl-isoquinoline-3-carbonyl)-amino]-acetic acid, [(1-ethylsulfanyl-4-hydroxy-isoquinoline-3-carbonyl)-amino]-acetic acid, {[4-hydroxy-1-(4-methoxy-phenylsulfanyl)-isoquinoline-3-carbonyl]-amino}-acetic acid, [(1-chloro-4-hydroxy-7-iodo-isoquinoline-3-carbonyl)-amino]-acetic acid, [(1-chloro-4-hydroxy-6-iodo-isoquinoline-3-carbonyl)-amino]-acetic acid, [(4-hydroxy-7-iodo-isoquinoline-3-carbonyl)-amino]-acetic acid, [(1-bromo-4-hydroxy-7-methyl-isoquinoline-3-carbonyl)-amino]-acetic acid, [(1-bromo-7-butoxy-4-hydroxy-isoquinoline-3-carbonyl)-amino]-acetic acid, [(1-bromo-6-butoxy-4-hydroxy-isoquinoline-3-carbonyl)-amino]-acetic acid, [carboxymethyl-(1-chloro-4-hydroxy-isoquinoline-3-carbonyl)-amino]-acetic acid; [carboxymethyl-(1-chloro-4-hydroxy-6-isopropoxy-isoquinoline-3-carbonyl)-amino]-acetic acid; 1-chloro-4-hydroxy-isoquinoline-3-carboxylic acid (2-amino-ethyl)-amide (trifluoro-acetic acid salt); 1-chloro-4-hydroxy-isoquinoline-3-carboxylic acid (2-methoxy-ethyl)-amide; 1-chloro-4-hydroxy-isoquinoline-3-carboxylic acid (2-hydroxy-ethyl)-amide; 1-chloro-4-hydroxy-isoquinoline-3-carboxylic acid (2-dimethylamino-ethyl)-amide; 1-chloro-4-hydroxy-isoquinoline-3-carboxylic acid (2-acetylamino-ethyl)-amide; 1-chloro-4-hydroxy-6-isopropoxy-isoquinoline-3-carboxylic acid (2-hydroxy-ethyl)-amide; 1-chloro-4-hydroxy-6-isopropoxy-isoquinoline-3-carboxylic acid (2-methoxy-ethyl)-amide; 1-chloro-4-hydroxy-6-isopropoxy-isoquinoline-3-carboxylic acid (2-amino-ethyl)-amide (trifluoro-acetic acid salt); 1-chloro-4-hydroxy-6-isopropoxy-isoquinoline-3-carboxylic acid (2-dimethylamino-ethyl)-amide; 1-chloro-4-hydroxy-7-isopropoxy-isoquinoline-3-carboxylic acid (2-amino-ethyl)-amide (trifluoro-acetic acid salt); 1-chloro-4-hydroxy-7-isopropoxy-isoquinoline-3-carboxylic acid (2-methoxy-ethyl)-amide; 1-chloro-4-hydroxy-7-isopropoxy-isoquinoline-3-carboxylic acid (2-dimethylamino-ethyl)-amide; 1-chloro-4-hydroxy-7-isopropoxy-isoquinoline-3-carboxylic acid (2-hydroxy-ethyl)-amide; (R)-2-[(1-chloro-4-hydroxy-isoquinoline-3-carbonyl)-amino]-3-hydroxy-propionic acid, (S)-2-[(1-chloro-4-hydroxy-isoquinoline-3-carbonyl)-amino]-3-hydroxy-propionic acid, (R)-2-[(1-chloro-4-hydroxy-6-isopropoxy-isoquinoline-3-carbonyl)-amino]-3-hydroxy-propionic acid, (S)-2-[(1-chloro-4-hydroxy-6-isopropoxy-isoquinoline-3-carbonyl)-amino]-3-hydroxy-propionic acid, (R)-2-[(1-chloro-4-hydroxy-7-isopropoxy-isoquinoline-3-carbonyl)-amino]-3-hydroxy-propionic acid, (S)-2-[(1-chloro-4-hydroxy-7-isopropoxy-isoquinoline-3-carbonyl)-amino]-3-hydroxy-propionic acid, 2-[(1-chloro-4-hydroxy-isoquinoline-3-carbonyl)-amino]-2-methyl-propionic acid, 2-[(1-chloro-4-hydroxy-6-isopropoxy-isoquinoline-3-carbonyl)-amino]-2-methyl-propionic acid, (R)-2-[(1-chloro-4-hydroxy-isoquinoline-3-carbonyl)-amino]-3-(1h-imidazol-4-yl)-propionic acid (trifluoro-acetic acid salt), (S)-2-[(1-chloro-4-hydroxy-isoquinoline-3-carbonyl)-amino]-3-(1 h-imidazol-4-yl)-propionic acid (trifluoro-acetic acid salt), (R)-2-[(1-chloro-4-hydroxy-isoquinoline-3-carbonyl)-amino]-3-methyl-butyric acid, (S)-2-[(1-chloro-4-hydroxy-isoquinoline-3-carbonyl)-amino]-3-methyl-butyric acid, (R)-2-[(1-chloro-4-hydroxy-6-isopropoxy-isoquinoline-3-carbonyl)-amino]-3-methyl-butyric acid, (S)-2-[(1-chloro-4-hydroxy-6-isopropoxy-isoquinoline-3-carbonyl)-amino]-3-methyl-butyric acid, (R)-2-[(1-chloro-4-hydroxy-7-isopropoxy-isoquinoline-3-carbonyl)-amino]-3-methyl-butyric acid, (S)-2-[(1-chloro-4-hydroxy-7-isopropoxy-isoquinoline-3-carbonyl)-amino]-3-methyl-butyric acid, (S)-

2-[(6-benzyloxy-1-chloro-4-hydroxy-isoquinoline-3-carbonyl)-amino]-3-methyl-butyric acid, (R)-2-[(1-chloro-4-hydroxy-isoquinoline-3-carbonyl)-amino]-3-phenyl-propionic acid, (S)-2-[(1-chloro-4-hydroxy-isoquinoline-3-carbonyl)-amino]-3-phenyl-propionic acid, (R)-2-[(1-chloro-4-hydroxy-6-isopropoxy-isoquinoline-3-carbonyl)-amino]-3-phenyl-propionic acid, (S)-2-[(1-chloro-4-hydroxy-6-isopropoxy-isoquinoline-3-carbonyl)-amino]-3-phenyl-propionic acid, (R)-2-[(1-chloro-4-hydroxy-7-isopropoxy-isoquinoline-3-carbonyl)-amino]-3-phenyl-propionic acid, (S)-2-[(1-chloro-4-hydroxy-7-isopropoxy-isoquinoline-3-carbonyl)-amino]-3-phenyl-propionic acid, (R)-2-[(1-chloro-4-hydroxy-isoquinoline-3-carbonyl)-amino]-3-(4-hydroxy-phenyl)-propionic acid, (S)-2-[(1-chloro-4-hydroxy-isoquinoline-3-carbonyl)-amino]-3-(4-hydroxy-phenyl)-propionic acid, (R)-2-[(1-chloro-4-hydroxy-6-isopropoxy-isoquinoline-3-carbonyl)-amino]-3-(4-hydroxy-phenyl)-propionic acid, (S)-2-[(1-chloro-4-hydroxy-6-isopropoxy-isoquinoline-3-carbonyl)-amino]-3-(4-hydroxy-phenyl)-propionic acid, (R)-2-[(1-chloro-4-hydroxy-7-isopropoxy-isoquinoline-3-carbonyl)-amino]-3-(4-hydroxy-phenyl)-propionic acid, (S)-2-[(1-chloro-4-hydroxy-7-isopropoxy-isoquinoline-3-carbonyl)-amino]-3-(4-hydroxy-phenyl)-propionic acid, (R)-2-[(1-chloro-4-hydroxy-6-isopropoxy-isoquinoline-3-carbonyl)-amino]-pentanoic acid, (S)-2-[(1-chloro-4-hydroxy-6-isopropoxy-isoquinoline-3-carbonyl)-amino]-pentanoic acid, (R)-1-(1-chloro-4-hydroxy-isoquinoline-3-carbonyl)-pyrrolidine-2-carboxylic acid, (S)-1-(1-chloro-4-hydroxy-isoquinoline-3-carbonyl)-pyrrolidine-2-carboxylic acid, (R)-1-(1-chloro-4-hydroxy-6-isopropoxy-isoquinoline-3-carbonyl)-pyrrolidine-2-carboxylic acid, (S)-1-(1-chloro-4-hydroxy-6-isopropoxy-isoquinoline-3-carbonyl)-pyrrolidine-2-carboxylic acid, (R)-6-amino-2-[(1-chloro-4-hydroxy-isoquinoline-3-carbonyl)-amino]-hexanoic acid (trifluoro-acetic acid salt), (S)-6-amino-2-[(1-chloro-4-hydroxy-isoquinoline-3-carbonyl)-amino]-hexanoic acid (trifluoro-acetic acid salt), (R)-6-amino-2-[(1-chloro-4-hydroxy-6-isopropoxy-isoquinoline-3-carbonyl)-amino]-hexanoic acid, trifluoroacetic acid salt, (S)-6-amino-2-[(1-chloro-4-hydroxy-6-isopropoxy-isoquinoline-3-carbonyl)-amino]-hexanoic acid (trifluoro-acetic acid salt), (R)-6-amino-2-[(1-chloro-4-hydroxy-7-isopropoxy-isoquinoline-3-carbonyl)-amino]-hexanoic acid, trifluoroacetic acid salt, (S)-6-amino-2-[(1-chloro-4-hydroxy-7-isopropoxy-isoquinoline-3-carbonyl)-amino]-hexanoic acid (trifluoro-acetic acid salt), (R)-2-[(1-chloro-4-hydroxy-isoquinoline-3-carbonyl)-amino]-succinic acid, (S)-2-[(1-chloro-4-hydroxy-isoquinoline-3-carbonyl)-amino]-succinic acid, (R)-2-[(1-chloro-4-hydroxy-6-isopropoxy-isoquinoline-3-carbonyl)-amino]-succinic acid, (S)-2-[(1-chloro-4-hydroxy-6-isopropoxy-isoquinoline-3-carbonyl)-amino]-succinic acid, (R)-2-[(1-chloro-4-hydroxy-7-isopropoxy-isoquinoline-3-carbonyl)-amino]-succinic acid, (R)-2-[(6-benzyloxy-1-chloro-4-hydroxy-isoquinoline-3-carbonyl)-amino]-propionic acid, (S)-2-[(7-benzyloxy-1-chloro-4-hydroxy-isoquinoline-3-carbonyl)-amino]-propionic acid, (R)-2-[(7-benzyloxy-1-chloro-4-hydroxy-isoquinoline-3-carbonyl)-amino]-propionic acid, (S)-2-[(1-chloro-4-hydroxy-isoquinoline-3-carbonyl)-amino]-propionic acid, (R)-2-[(1-chloro-4-hydroxy-isoquinoline-3-carbonyl)-amino]-propionic acid, (S)-2-[(6-isopropoxy-1-chloro-4-hydroxy-isoquinoline-3-carbonyl)-amino]-propionic acid, (R)-2-[6-isopropoxy-1-chloro-4-hydroxy-isoquinoline-3-carbonyl)-amino]-propionic acid, (S)-2-[(7-isopropoxy-1-chloro-4-hydroxy-isoquinoline-3-carbonyl)-amino-propionic acid, (R)-2-[(7-isopropoxy-1-chloro-4-hydroxy-isoquinoline-3-carbonyl)-amino] propionic acid, {[7-(3,5-difluoro-phenoxy)-4-hydroxy-isoquinoline-3-carbonyl]-amino}-acetic acid, {[6-(3,5-difluoro-phenoxy)-4-hydroxy-isoquinoline-3-carbonyl]-amino}-acetic acid, ({7-[4-(4-fluoro-phenoxy)-phenoxy]-4-hydroxy-isoquinoline-3-carbonyl}-amino)-acetic acid, ({6-[4-(4-fluoro-phenoxy)-phenoxy]4-hydroxy-isoquinoline-3-carbonyl}-amino)-acetic acid, {[7-(3-chloro-4-fluoro-phenoxy)-4-hydroxy-isoquinoline-3-carbonyl]-amino}-acetic acid, {[6-(3-chloro-4-fluoro-phenoxy)-4-hydroxy-isoquinoline-3-carbonyl]-amino}-acetic acid, (S)-2-{[7-(3-fluoro-5-methoxy-phenoxy)-4-hydroxy-isoquinoline-3-carbonyl]-amino}-propionic acid, 2-(S)-[(7-cyclohexyloxy-4-hydroxy-isoquinoline-3-carbonyl)-amino]-propionic acid, 2-(S)-{[7-(4-fluoro-phenoxy)-4-hydroxy-1-methyl-isoquinoline-3-carbonyl]-amino}-propionic acid, 2-(S)-{[7-(4-fluoro-phenoxy)-4-hydroxy-isoquinoline-3-carbonyl]-amino}-propionic acid, 2-(S)-[(4-hydroxy-1-methyl-7-phenoxy-isoquinoline-3-carbonyl)-amino]-propionic acid, 2-(S)-[(4-hydroxy-1-methyl-7-phenylsulfanyl-isoquinoline-3-carbonyl)-amino]-propionic acid, 2-(S)-{[4-hydroxy-7-(4-trifluoromethyl-phenoxy)-isoquinoline-3-carbonyl]-amino}-propionic acid, {[7-(4-chloro-phenoxy)-4-hydroxy-1-methyl-isoquinoline-3-carbonyl]-amino}-acetic acid, {[6-(4-chloro-phenoxy)-4-hydroxy-1-methyl-isoquinoline-3-carbonyl]-amino}-acetic acid, {[7-(3,5-difluoro-phenoxy)-4-hydroxy-1-methyl-isoquinoline-3-carbonyl]-amino}-acetic acid, {[4-hydroxy-7-(4-methoxy-phenoxy)-1-methyl-isoquinoline-3-carbonyl]-amino}-acetic acid, {[4-hydroxy-6-(4-methoxy-phenoxy)-1-methyl-isoquinoline-3-carbonyl]-amino}-acetic acid, [(6-cyclohexyloxy-4-hydroxy-isoquinoline-3-carbonyl)-amino]-acetic acid, [(7-cyclohexyloxy-4-hydroxy-isoquinoline-3-carbonyl)-amino]-acetic acid, [(7-cyclohexyloxy-4-hydroxy-1-methyl-isoquinoline-3-carbonyl)-amino]-acetic acid, [(7-cyclohexylsulfanyl-4-hydroxy-isoquinoline-3-carbonyl)-amino]-acetic acid, [(7-cyclohexanesulfonyl-4-hydroxy-isoquinoline-3-carbonyl)-amino]-acetic acid, [(4-hydroxy-1-isobutyl-isoquinoline-3-carbonyl)-amino]-acetic acid, [(1-ethyl-4-hydroxy-7-phenoxy-isoquinoline-3-carbonyl)-amino]-acetic acid, [(1-dimethylaminomethyl-4-hydroxy-7-phenylsulfanyl-isoquinoline-3-carbonyl)-amino]-acetic acid, [(4-hydroxy-1-methyl-7-phenylsulfanyl-isoquinoline-3-carbonyl)-amino]-acetic acid, {[4-hydroxy-1-methyl-7-(4-trifluoromethyl-phenoxy)-isoquinoline-3-carbonyl]-amino}-acetic acid.

In certain aspects, compounds of the present invention include 4-oxo-[1,10]-phenanthrolines. Exemplary 4-oxo-[1,10]-phenanthrolines are disclosed in, e.g., International Publication No. WO 03/049686 and International Publication No. WO 03/053997, and include compounds of Formula II

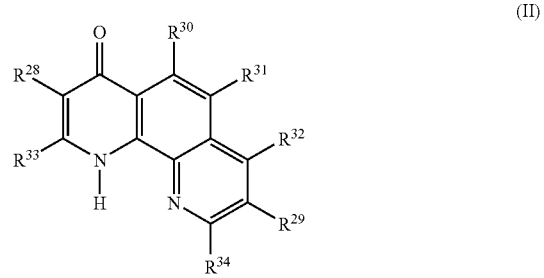

(II)

where $R^{28}$ is hydrogen, nitro, amino, cyano, halogen, $(C_1\text{-}C_4)$-alkyl, carboxy or a metabolically labile ester derivative thereof, $(C_1-C_4)$-alkylamino, di-$(C_1-C_4)$-alkylamino, $(C_1-C_6)$-alkoxycarbonyl, $(C_2-C_4)$-alkanoyl, hydroxy-$(C_1-C_4)$-alkyl, carbamoyl, N—$(C_1-C_4)$-alkylcarbamoyl, $(C_1-C_4)$-alkylthio, $(C_1-C_4)$-alkylsulfinyl, $(C_1-C_4)$-alkylsulfonyl, phenylthio, phenylsulfinyl, phenylsulfonyl, said phenyl or phenyl groups being optionally substituted with 1 to 4 identical or different halogen, $(C_1-C_4)$-alkyoxy, $(C_1-C_4)$-alkyl, cyano, hydroxy, trifluoromethyl, fluoro-$(C_1-C_4)$-alkylthio, fluoro-$(C_1-C_4)$-alkylsulfinyl, fluoro-$(C_1-C_4)$-alkylsulfonyl, $(C_1-C_4)$-alkoxy-$(C_2-C_4)$-alkoxycarbonyl, N,N-di-[$(C_1-C_4)$-alkyl]carbamoyl-$(C_1-C_4)$-alkoxycarbonyl, $(C_1-C_4)$-alkylamino-$(C_2-C_4)$-alkoxycarbonyl, di-$(C_1-C_4)$-alkylamino-$(C_2-C_4)$-alkoxycarbonyl, $(C_1-C_4)$-alkoxy-$(C_2-C_4)$-alkoxy-$(C_2-C_4)$-alkoxycarbonyl, $(C_2-C_4)$-alkanoyloxy-$C_1-C_4)$-alkyl, or N-[amino-$(C_2-C_8)$-alkyl]-carbamoyl;

$R^{29}$ is hydrogen, hydroxy, amino, cyano, halogen, $(C_1-C_4)$-alkyl, carboxy or metabolically labile ester derivative thereof, $(C_1-C_4)$-alkylamino, di-$(C_1-C_4)$-alkylamino, $(C_1-C_6)$-alkoxycarbonyl, $(C_2-C_4)$-alkanoyl, $(C_1-C_4)$-alkoxy, carboxy-$(C_1-C_4)$-alkoxy, $(C_1-C_4)$-alkoxycarbonyl-$(C_1-C_4)$-alkoxy, carbamoyl, N—$(C_1-C_8)$-alkylcarbamoyl, N,N-di-$(C_1-C_8)$-alkylcarbamoyl, N-[amino-$(C_2-C_8)$-alkyl]-carbamoyl, N—[$(C_1-C_4)$-alkylamino-$(C_1-C_8)$-alkyl]-carbamoyl, N-[di-$(C_1-C_4)$-alkylamino-$(C_1-C_8)$-alkyl]]-carbamoyl, N-cyclohexylcarbamoyl, N-[cyclopentyl]-carbamoyl, N—$(C_1-C_4)$-alkylcyclohexylcarbamoyl, N—$(C_1-C_4)$-alkylcyclopentylcarbamoyl, N-phenylcarbamoyl, N—$(C_1-C_4)$-alkyl-N-phenylcarbamoyl, N,N-diphenylcarbamoyl, N-[phenyl-$(C_1-C_4)$-alkyl]-carbamoyl, N—$(C_1-C_4)$-alkyl-N-[phenyl-$(C_1-C_4)$-alkyl]-carbamoyl, or N,N-di-[phenyl-$(C_1-C_4)$-alkyl]-carbamoyl, said phenyl or phenyl groups being optionally substituted with 1 to 4 identical or different halogen, $(C_1-C_4)$-alkyoxy, $(C_1-C_4)$-alkyl, cyano, hydroxy, trifluoromethyl, N—[$(C_2-C_4)$-alkanoyl]-carbamoyl, N—[$(C_1-C_4)$-alkoxycarbonyl]-carbamoyl, N-[fluoro-$(C_2-C_6)$-alkyl]-carbamoyl, N,N-[fluoro-$(C_2-C_6)$-alkyl]-N—$(C_1-C_4)$-alkylcarbamoyl, N,N-[di-fluoro-$(C_2-C_6)$-alkyl]carbamoyl, pyrrolidin-1-ylcarbonyl, piperidinocarbonyl, piperazin-1-ylcarbonyl, morpholinocarbonyl, wherein the heterocyclic group, is optionally substituted with 1 to 4, $(C_1-C_4)$-alkyl, benzyl, 1,2,3,4-tetrahydro-isoquinolin-2-ylcarbonyl, N,N-[di-$(C_1-C_4)$-alkyl]-thiocarbamoyl, N—$(C_2-C_4)$-alkanoylamino, or N—[$(C_1-C_4)$-alkoxycarbonyl]-amino;

$R^{30}$ is hydrogen, $(C_1-C_4)$-alkyl, $(C_2-C_4)$-alkoxy, halo, nitro, hydroxy, fluoro-(1-4C)alkyl, or pyridinyl;

$R^{31}$ is hydrogen, $(C_1-C_4)$-alkyl, $(C_2-C_4)$-alkoxy, halo, nitro, hydroxy, fluoro-$(C_1-C_4)$-alkyl, pyridinyl, or methoxy;

$R^{32}$ is hydrogen, hydroxy, amino, $(C_1-C_4)$-alkylamino, di-$(C_1-C_4)$-alkylamino, halo, $(C_1-C_4)$-alkoxy-$(C_2-C_4)$-alkoxy, fluoro-$(C_1-C_6)$-alkoxy, pyrrolidin-1-yl, piperidino, piperazin-1-yl, or morpholino, wherein the heterocyclic group is optionally substituted with 1 to 4 identical or different $(C_1-C_4)$-alkyl or benzyl; and $R^{33}$ and $R^{34}$ are individually selected from hydrogen, $(C_1-C_4)$-alkyl, and $(C_1-C_4)$-alkoxy;

including pharmaceutically-acceptable salts, esters, and pro-drugs derived therefrom.

Exemplary compounds of Formula II are described in U.S. Pat. Nos. 5,916,898 and 6,200,974, and International Publication No. WO 99/21860. All compounds listed in the foregoing patents and publication, in particular, those listed in the compound claims and the final products of the working examples, are hereby incorporated into the present application by reference herein. Exemplary compounds of Formula II include 4-oxo-1,4-dihydro-[1,10]phenanthroline-3-carboxylic acid (Compound F; see, e.g., Seki et al. (1974) Chem Abstracts 81:424, No. 21), 3-carboxy-5-hydroxy-4-oxo-3,4-dihydro-1,10-phenanthroline, 3-carboxy-5-methoxy-4-oxo-3,4-dihydro-1,10-phenanthroline, 5-methoxy-4-oxo-1,4-dihydro-[1,10]phenanthroline-3-carboxylic acid ethyl ester, 5-methoxy-4-oxo-1,4-dihydro-[1,10]phenanthroline-3-carboxylic acid, and 3-carboxy-8-hydroxy-4-oxo-3,4-dihydro-1,10-phenanthroline.

In certain aspects, compounds of the present invention include aryl-sulfono-amino-hydroxamates. Exemplary aryl-sulfono-amino-hydroxamates are disclosed in, e.g., International Publication No. WO 03/049686, International Publication No. WO 03/053997, and International Publication No. WO 04/108121. Such compounds include compounds of Formula III

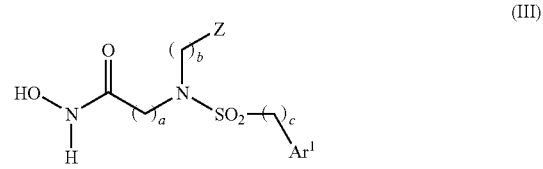

(III)

or pharmaceutically acceptable salts thereof, wherein:

a is an integer from 1 to 4;

b is an integer from 0 to 4;

c is an integer from 0 to 4;

Z is selected from the group consisting of $(C_3-C_{10})$ cycloalkyl, $(C_3-C_{10})$ cycloalkyl independently substituted with one or more $Y^1$, 3-10 membered heterocycloalkyl and 3-10 membered heterocycloalkyl independently substituted with one or more $Y^1$; $(C_5-C_{20})$ aryl, $(C_5-C_{20})$ aryl independently substituted with one or more $Y^1$, 5-20 membered heteroaryl and 5-20 membered heteroaryl independently substituted with one or more $Y^1$;

$Ar^1$ is selected from the group consisting of $(C_5-C_{20})$ aryl, $(C_5-C_{20})$ aryl independently substituted with one or more $Y^2$, 5-20 membered heteroaryl and 5-20 membered heteroaryl independently substituted with one or more $Y^2$;

each $Y^1$ is independently selected from the group consisting of a lipophilic functional group, $(C_5-C_{20})$ aryl, $(C_6-C_{26})$ alkaryl, 5-20 membered heteroaryl and 6-26 membered alk-heteroaryl;

each $Y^2$ is independently selected from the group consisting of —R', —OR', —OR", —SR', —SR", —NR'R', —NO_2, —CN, -halogen, -trihalomethyl, trihalomethoxy, —C(O)R', —C(O)OR', —C(O)NR'R', —C(O)NR'R', —C(NR'R')=NOR', —NR'—C(O)R', —SO_2R', —SO_2R", —NR'-SO_2—R', —NR'—C(O)—NR'R', tetrazol-5-yl, —NR'—C(O)—OR', —C(NR'R')=NR', —S(O)—R', —S(O)—R", and —NR'—C(S)—NR'R'; and each R' is independently selected from the group consisting of —H, $(C_1-C_8)$ alkyl, $(C_2-C_8)$ alkenyl, and $(C_2-C_8)$ alkynyl; and each R" is independently selected from the group consisting of $(C_5-C_{20})$ aryl and $(C_5-C_{20})$ aryl independently substituted with one or more —OR', —SR', —NR'R', —NO_2, —CN, halogen or trihalomethyl groups, or wherein c is 0 and $Ar^1$ is an N' substituted urea-aryl, the compound has the structural Formula IIIa:

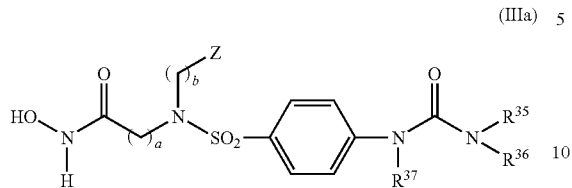

or pharmaceutically acceptable salts thereof, wherein:
a, b, and Z are as defined above; and
$R^{35}$ and $R^{36}$ are each independently selected from the group consisting of hydrogen, $(C_1-C_8)$ alkyl, $(C_2-C_8)$ alkenyl, $(C_2-C_8)$ alkynyl, $(C_3-C_{10})$ cycloalkyl, $(C_5-C_{20})$ aryl, $(C_5-C_{20})$ substituted aryl, $(C_6-C_{26})$ alkaryl, $(C_6-C_{26})$ substituted alkaryl, 5-20 membered heteroaryl, 5-20 membered substituted heteroaryl, 6-26 membered alk-heteroaryl, and 6-26 membered substituted alk-heteroaryl; and
$R^{37}$ is independently selected from the group consisting of hydrogen, $(C_1-C_8)$ alkyl, $(C_2-C_8)$ alkenyl, and $(C_2-C_8)$ alkynyl.

Exemplary compounds of Formula III are described in International Publication No. WO 00/50390. All compounds listed in WO 00/50390, in particular, those listed in the compound claims and the final products of the working examples, are hereby incorporated into the present application by reference herein. Exemplary compounds of Formula III include 3-{[4-(3,3-dibenzyl-ureido)-benzenesulfonyl]-[2-(4-methoxy-phenyl)-ethyl]-amino}-N-hydroxy-propionamide (Compound G), 3-{{4-[3-(4-chloro-phenyl)-ureido]-benzenesulfonyl}-[2-(4-methoxy-phenyl)-ethyl]-amino}-N-hydroxy-propionamide, and 3-{{4-[3-(1,2-diphenyl-ethyl)-ureido]-benzenesulfonyl}-[2-(4-methoxy-phenyl)-ethyl]-amino}-N-hydroxy-propionamide. In certain embodiments, a 2-oxoglutarate mimetic of the present invention is selected from a compound of the Formula IV

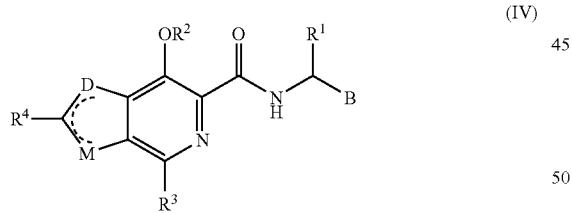

wherein
$R^1$ are selected from the group consisting of hydrogen, $(C_1-C_6)$-alkyl, $(C_3-C_7)$-cycloalkyl, aryl, or a substituent of the α-carbon atom of an α-amino acid, wherein the amino acid is a natural L-amino acid or its D-isomer;
B is —$CO_2H$ or a $CO_2$-G carboxyl radical, where G is a radical of an alcohol G-OH in which G is selected from the group consisting of $(C_1-C_{20})$-alkyl radical, $(C_3-C_8)$ cycloalkyl radical, $(C_2-C_{20})$-alkenyl radical, $(C_3-C_8)$-cycloalkenyl radical, retinyl radical, $(C_2-C_{20})$-alkynyl radical, $(C_4-C_{20})$-alkynynyl radical;
$R^2$ is selected from the group consisting of hydrogen, $(C_1-C_{10})$-alkyl, $(C_2-C_{10})$-alkenyl, $(C_2-C_{10})$-alkynyl, wherein alkenyl or alkynyl contains one or two C—C multiple bonds; unsubstituted fluoroalkyl radical of the formula —$[CH_2]_x$—$C_fH_{(2f+1-g)}$—$F_g$, aryl, heteroaryl, and $(C_7-C_{11})$-aralkyl;
one of D or M is —S—, and the other is =$C(R^5)$—;
$R^3$, $R^4$, and $R^5$ are identical or different and are selected from the group consisting of hydrogen, hydroxyl, halogen, cyano, trifluoromethyl, nitro, carboxyl; $(C_1-C_{20})$-alkyl, $(C_3-C_8)$-cycloalkyl, $(C_3-C_8)$-cycloalkoxy, $(C_6-C_{12})$-aryl, $(C_7-C_{16})$-aralkyl, $(C_7-C_{16})$-aralkenyl, $(C_7-C_{16})$-aralkynyl, $(C_2-C_{20})$-alkenyl, $(C_2-C_{20})$-alkynyl, $(C_1-C_{20})$-alkoxy, $(C_2-C_{20})$-alkenyloxy, $(C_2-C_{20})$-alkynyloxy, retinyloxy, $(C_6-C_{12})$-aryloxy, $(C_7-C_{16})$-aralkyloxy, $(C_1-C_{16})$-hydroxyalkyl, —O—$[CH_2]_xC_fH_{(2f+1-g)}$$F_g$, —$OCF_2Cl$, —$OCF_2$—$CHFCl$, $(C_1-C_{20})$-alkylcarbonyl, $(C_3-C_8)$-cycloalkylcarbonyl, $(C_6-C_{12})$-arylcarbonyl, $(C_7-C_{16})$-aralkylcarbonyl, cinnamoyl, $(C_2-C_{20})$-alkenylcarbonyl, $(C_2-C_{20})$-alkynylcarbonyl, $(C_1-C_{20})$-alkoxycarbonyl, $(C_6-C_{12})$-aryloxycarbonyl, $(C_7-C_{16})$-aralkoxycarbonyl, $(C_3-C_8)$-cycloalkoxycarbonyl, $(C_2-C_{20})$-alkenyloxycarbonyl, retinyloxycarbonyl, $(C_2-C_{20})$-alkynyloxycarbonyl, $(C_1-C_{12})$-alkylcarbonyloxy, $(C_3-C_8)$-cycloalkylcarbonyloxy, $(C_6-C_{12})$-arylcarbonyloxy, $(C_7-C_{16})$-aralkylcarbonyloxy, cinnamoyloxy, $(C_2-C_{12})$-alkenylcarbonyloxy, $(C_2-C_{12})$-alkynylcarbonyloxy, $(C_1-C_{12})$-alkoxycarbonyloxy, $(C_6-C_{12})$-aryloxycarbonyloxy, $(C_7-C_{16})$-aralkyloxycarbonyloxy, $(C_3-C_8)$-cycloalkoxycarbonyloxy, $(C_2-C_{12})$-alkenyloxycarbonyloxy, $(C_2-C_{12})$-alkynyloxycarbonyloxy, carbamoyl, N—$(C_1-C_{12})$-alkylcarbamoyl, N,N-di-$(C_1-C_2)$-alkylcarbamoyl, N—$(C_3-C_8)$-cycloalkylcarbamoyl, N,N-dicyclo-$(C_3-C_8)$-alkylcarbamoyl, N—$(C_1-C_{10})$-alkyl-N—$(C_3-C_8)$-cycloalkylcarbamoyl, N—(($C_3-C_8$)-cycloalkyl-($C_1-C_6$)-alkyl)-carbamoyl, N-(+)-dehydroabietylcarbamoyl, N—$(C_1-C_6)$-alkyl-N-(+)-dehydroabietylcarbamoyl, N—$(C_6-C_{12})$-arylcarbamoyl, N—$(C_7-C_{16})$-aralkylcarbamoyl, N—$(C_1-C_{10})$-alkyl-N—$(C_6-C_{16})$-arylcarbamoyl, N—$(C_1-C_{10})$-alkyl-N—$(C_7-C_{16})$-aralkylcarbamoyl, carbamoyloxy, N—$(C_1-C_{12})$-alkylcarbamoyloxy, N,N-di-$(C_1-C_{12})$-alkylcarbamoyloxy, N—$(C_3-C_8)$-cycloalkylcarbamoyloxy, N—$(C_6-C_{12})$-arylcarbamoyloxy, N—$(C_7-C_{16})$-aralkylcarbamoyloxy, N—$(C_1-C_{10})$-alkyl-N—$(C_6-C_{12})$-arylcarbamoyloxy, N—$(C_1-C_{10})$-alkyl-N—$(C_7-C_{16})$-aralkylcarbamoyloxy, N—(($C_1-C_{10}$)-alkyl)-carbamoyloxy, N—$(C_1-C_{10})$-alkyl-N—(($C_7-C_{16}$)-aralkyloxy-($C_1-C_{10}$)-alkyl)-carbamoyloxyamino, $(C_1-C_{12})$-alkylamino, di-$(C_1-C_{12})$-alkylamino, $(C_3-C_8)$-cycloalkylamino, $(C_3-C_{12})$-alkenylamino, $(C_3-C_{12})$-alkynylamino, N—$(C_6-C_{12})$-arylamino, N—$(C_7-C_{11})$-aralkylamino, N-alkyl-aralkylamino, N-alkyl-arylamino, $(C_1-C_{12})$-alkoxyamino, $(C_1-C_{12})$-alkoxy-N—$(C_1-C_{10})$-alkylamino, $(C_1-C_{12})$-alkanoylamino, $(C_3-C_8)$-cycloalkanoylamino, $(C_6-C_{12})$-aroylamino, $(C_7-C_{16})$-aralkanoylamino, $(C_1-C_{12})$-alkanoyl-N—$(C_1-C_{10})$-alkylamino, $(C_3-C_8)$-cycloalkanoyl-N—$(C_1-C_{10})$-alkylamino, $(C_6-C_{12})$-aroyl-N—$(C_1-C_{10})$-alkylamino, $(C_7-C_{11})$-aralkanoyl-N—$(C_1-C_{10})$-alkylamino, amino-$(C_1-C_{10})$-alkyl, $(C_1-C_{20})$-alkylmercapto, $(C_1-C_{20})$-alkylsulfinyl, $(C_1-C_{20})$-alkylsulfonyl, $(C_6-C_{12})$-arylmercapto, $(C_6-C_{12})$-arylsulfinyl, $(C_6-C_{12})$-arylsulfonyl, $(C_7-C_{16})$-aralkylmercapto, $(C_7-C_{16})$-aralkylsulfinyl, $(C_7-C_{16})$-aralkylsulfonyl, sulfamoyl, N—$(C_1-C_{10})$-alkylsulfamoyl, N,N-di-$(C_1-C_{10})$-alkylsulfamoyl, $(C_3-C_8)$-cycloalkylsulfamoyl, N—$(C_6-C_{12})$-arylsulfamoyl, N—$(C_7-C_{16})$-aralkylsulfamoyl, N—$(C_1-C_{10})$-alkyl- N—($C_6$-$C_{12}$)-arylsulfamoyl, N—($C_1$-$C_{10}$)-alkyl-N—($C_7$-$C_{16}$)-aralkylsulfamoyl, ($C_1$-$C_{10}$)-alkylsulfonamido, ($C_7$-$C_{16}$)-aralkylsulfonamido, and N—(($C_1$-$C_{10}$)-alkyl-($C_7$-$C_{16}$)-aralkylsulfonamido; where an aryl radical may be substituted by 1 to 5 substituents selected from hydroxyl, halogen, cyano, trifluoromethyl, nitro, carboxyl, ($C_2$-$C_{16}$)-alkyl, ($C_3$-$C_8$)-cycloalkyl, ($C_3$-$C_8$)-cycloalkoxy, ($C_6$-$C_{12}$)-aryl, ($C_7$-$C_{16}$)-aralkyl, ($C_2$-$C_{16}$)-alkenyl, ($C_2$-$C_{12}$)-alkynyl, ($C_1$-$C_{16}$)-alkoxy, ($C_1$-$C_{16}$)-alkenyloxy, ($C_6$-$C_{12}$)-aryloxy, ($C_7$-$C_{16}$)-aralkyloxy, ($C_1$-$C_8$)-hydroxyalkyl, —O—[$CH_2$]$_x$$C_f$$H_{(2f+1-g)}$$F_g$, —$OCF_2Cl$, and —$OCF_2$—$CHFCl$;

x is 0 to 3;

f is 1 to 8; and g is 0 or 1 to (2f+1);

including the physiologically active salts, esters, and prodrugs derived therefrom.

Compounds of Formula IV include, but are not limited to, [(2-bromo-4-hydroxy-thieno[2,3-c]pyridine-5-carbonyl)-amino]-acetic acid, [(2-bromo-7-hydroxy-thieno[3,2-c]pyridine-6-carbonyl)-amino]-acetic acid, {[4-hydroxy-2-(4-methoxy-phenyl)-thieno[2,3-c]pyridine-5-carbonyl]-amino}-acetic acid, {[7-hydroxy-2-(4-methoxy-phenyl)-thieno[3,2-c]pyridine-6-carbonyl]-amino}-acetic acid, [(4-hydroxy-2,7-dimethyl-thieno[2,3-c]pyridine-5-carbonyl)-amino]-acetic acid, [(7-hydroxy-2,4-dimethyl-thieno[3,2-c]pyridine-6-carbonyl)-amino]-acetic acid, {[7-hydroxy-4-methyl-2-(4-phenoxy-phenyl)-thieno[3,2-c]pyridine-6-carbonyl]-amino}-acetic acid, {[4-hydroxy-2-(4-phenoxy-phenyl)-7-methyl-thieno[2,3-c]pyridine-5-carbonyl]-amino}-acetic acid, {[4-hydroxy-2-(4-phenoxy-phenyl)-thieno[2,3-c]pyridine-5-carbonyl]-amino}-acetic acid, {[7-hydroxy-2-(4-phenoxy-phenyl)-thieno[3,2-c]pyridine-6-carbonyl]-amino}-acetic acid, [(2,7-dibromo-4-hydroxy-thieno[2,3-c]pyridine-5-carbonyl)-amino]-acetic acid, [(2-bromo-7-chloro-4-hydroxy-thieno[2,3-c]pyridine-5-carbonyl)-amino]-acetic acid, [(7-hydroxy-thieno[3,2-c]pyridine-6-carbonyl)-amino]-acetic acid, [(4-hydroxy-thieno[2,3-c]pyridine-5-carbonyl)-amino]-acetic acid, [(2-bromo-4-chloro-7-hydroxy-thieno[3,2-c]pyridine-6-carbonyl)-amino]-acetic acid, [(2,4-dibromo-7-hydroxy-thieno[3,2-c]pyridine-6-carbonyl)-amino]-acetic acid, [(7-hydroxy-2-phenylsulfanyl-thieno[3,2-c]pyridine-6-carbonyl)-amino]-acetic acid, [(4-hydroxy-2-phenylsulfanyl-thieno[2,3-c]pyridine-5-carbonyl)-amino]-acetic acid, [(4-hydroxy-2,7-diphenyl-thieno[2,3-c]pyridine-5-carbonyl)-amino]-acetic acid, [(7-hydroxy-2,4-diphenyl-thieno[3,2-c]pyridine-6-carbonyl)-amino]-acetic acid, [(7-hydroxy-2-styryl-thieno[3,2-c]pyridine-6-carbonyl)-amino]-acetic acid, [(7-hydroxy-2-phenoxy-thieno[3,2-c]pyridine-6-carbonyl)-amino]-acetic acid, [(7-hydroxy-2-phenethyl-thieno[3,2-c]pyridine-6-carbonyl)-amino]-acetic acid, {[7-hydroxy-2-(3-trifluoromethyl-phenyl)-thieno[3,2-c]pyridine-6-carbonyl]-amino}-acetic acid, {[4-bromo-7-hydroxy-2-(3-trifluoromethyl-phenyl)-thieno[3,2-c]pyridine-6-carbonyl]-amino}-acetic acid, {[4-cyano-7-hydroxy-2-(3-trifluoromethyl-phenyl)-thieno[3,2-c]pyridine-6-carbonyl]-amino}-acetic acid, [(2-cyano-7-hydroxy-thieno[3,2-c]pyridine-6-carbonyl)-amino]-acetic acid, {[7-hydroxy-2-(4-trifluoromethyl-phenyl)-thieno[3,2-c]pyridine-6-carbonyl]-amino}-acetic acid, {[7-hydroxy-2-(2-trifluoromethyl-phenyl)-thieno[3,2-c]pyridine-6-carbonyl]-amino}-acetic acid, {[4-bromo-3-(4-fluoro-phenyl)-7-hydroxy-thieno[3,2-c]pyridine-6-carbonyl]-amino}-acetic acid, {[3-(4-fluoro-phenyl)-7-hydroxy-thieno[3,2-c]pyridine-6-carbonyl]-amino}-acetic acid, {[3-(4-fluoro-phenyl)-7-hydroxy-4-methyl-thieno[3,2-c]pyridine-6-carbonyl]-amino}-acetic acid, {[4-cyano-3-(4-fluoro-phenyl)-7-hydroxy-thieno[3,2-c]pyridine-6-carbonyl]-amino}-acetic acid, {[2-(4-fluoro-phenyl)-7-hydroxy-thieno[3,2-c]pyridine-6-carbonyl]-amino}-acetic acid, {[2-(4-fluoro-phenyl)-7-hydroxy-4-methyl-thieno[3,2-c]pyridine-6-carbonyl]-amino}-acetic acid, {[2,3-bis-(4-fluoro-phenyl)-7-hydroxy-thieno[3,2-c]pyridine-6-carbonyl]-amino}-acetic acid, {[7-bromo-3-(4-fluoro-phenyl)-4-hydroxy-thieno[2,3-c]pyridine-5-carbonyl]-amino}-acetic acid, {[3-(4-fluoro-phenyl)-4-hydroxy-thieno[2,3-c]pyridine-5-carbonyl]-amino}-acetic acid, {[2-(4-fluoro-phenyl)-4-hydroxy-thieno[2,3-c]pyridine-5-carbonyl]-amino}-acetic acid, {[2-(4-fluoro-phenyl)-4-hydroxy-7-methyl-thieno[2,3-c]pyridine-5-carbonyl]-amino}-acetic acid, [(7-chloro-4-hydroxy-thieno[2,3-c]pyridine-5-carbonyl)-amino]-acetic acid, [(4-chloro-7-hydroxy-thieno[3,2-c]pyridine-6-carbonyl)-amino]-acetic acid, [(7-bromo-4-hydroxy-thieno[2,3-c]pyridine-5-carbonyl)-amino]-acetic acid, [(4-bromo-7-hydroxy-thieno[3,2-c]pyridine-6-carbonyl)-amino]-acetic acid, [(4-hydroxy-7-phenyl-thieno[2,3-c]pyridine-5-carbonyl)-amino]-acetic acid, [(7-hydroxy-4-phenyl-thieno[3,2-c]pyridine-6-carbonyl)-amino]-acetic acid, {[7-(4-fluoro-phenyl)-4-hydroxy-thieno[2,3-c]pyridine-5-carbonyl]-amino}-acetic acid, {[4-(4-fluoro-phenyl)-7-hydroxy-thieno[3,2-c]pyridine-6-carbonyl]-amino}-acetic acid, 2-(7-(furan-2-yl)-4-hydroxy-thieno[2,3-c]pyridine-5-carboxamido)acetic acid, [(4-furan-2-yl-7-hydroxy-thieno[3,2-c]pyridine-6-carbonyl)-amino]-acetic acid, [(7-furan-3-yl-4-hydroxy-thieno[2,3-c]pyridine-5-carbonyl)-amino]-acetic acid, [(4-furan-3-yl-7-hydroxy-thieno[3,2-c]pyridine-6-carbonyl)-amino]-acetic acid, 2-(4-hydroxy-7-(thiophen-2-yl)thieno[2,3-c]pyridine-5-carboxamido)acetic acid, [(7-hydroxy-4-thiophen-2-yl-thieno[3,2-c]pyridine-6-carbonyl)-amino]-acetic acid, [(4-hydroxy-7-thiophen-3-yl-thieno[2,3-c]pyridine-5-carbonyl)-amino]-acetic acid, [(7-hydroxy-4-thiophen-3-yl-thieno[3,2-c]pyridine-6-carbonyl)-amino]-acetic acid, [(4-hydroxy-7-methyl-thieno[2,3-c]pyridine-5-carbonyl)-amino]-acetic acid, [(7-hydroxy-4-methyl-thieno[3,2-c]pyridine-6-carbonyl)-amino]-acetic acid, [(7-ethynyl-4-hydroxy-thieno[2,3-c]pyridine-5-carbonyl)-amino]-acetic acid, [(4-ethynyl-7-hydroxy-thieno[3,2-c]pyridine-6-carbonyl)-amino]-acetic acid, [(7-cyano-4-hydroxy-thieno[2,3-c]pyridine-5-carbonyl)-amino]-acetic acid, and [(4-cyano-7-hydroxy-thieno[3,2-c]pyridine-6-carbonyl)-amino]-acetic acid.

Exemplary compounds for use in the present methods include Compound A (1-Chloro-4-hydroxy-isoquinoline-3-carbonyl)-amino]-acetic acid; Compound B (S)-2-[(4-Hydroxy-7-phenoxy-isoquinoline-3-carbonyl)-amino]-propionic acid; Compound C {[4-Hydroxy-7-(4-methoxy-phenoxy)-isoquinoline-3-carbonyl]-amino}-acetic acid; Compound D [(4-Hydroxy-1-methyl-7-phenoxy-isoquinoline-3-carbonyl)-amino]-acetic acid, Compound E [7-(4-Fluoro-phenoxy)-4-hydroxy-isoquinoline-3-carbonyl]-amino-acetic acid, Compound F [4-Oxo-1,4-dihydro-[1,10]phenanthroline-3-carboxylic acid], Compound G [3-{[4-(3,3-Dibenzyl-ureido)-benzenesulfonyl]-[2-(4-methoxy-phenyl)-ethyl]-amino}-N-hydroxy-propionamide], Compound H [[(7-Chloro-3-hydroxy-quinoline-2-carbonyl)-amino]-acetic acid], Compound I [[(1-Chloro-4-hydroxy-7-methoxy-isoquinoline-3-carbonyl)-amino]-acetic acid], Compound J [[(6,7-Dichloro-4-hydroxy-isoquinoline-3-carbonyl)-amino]-acetic acid], Compound K [[(4-Hydroxy-7-phenoxy-isoquinoline-3-carbonyl)-amino]-acetic acid], Compound L [(S)-2-[(4-Hydroxy-7-phenylsulfanyl-isoquinoline-3-carbonyl)-amino]-propionic acid], Compound M [[(4-Hydroxy-1,7-diphenoxy-isoquinoline-3-carbonyl)- amino]-acetic acid], and Compound N [(4-hydroxy-7-phenylsulfanyl-isoquinoline-3-carbonyl)-amino]-acetic acid.

Unless otherwise specified, the term "alkyl" as used herein refers to monovalent alkyl groups having from 1 to 10 carbon atoms, preferably from 1 to 5 carbon atoms and more preferably 1 to 3 carbon atoms. This term is exemplified by groups such as methyl, ethyl, n-propyl, iso-propyl, n-butyl, t-butyl, n-pentyl and the like.

The term "substituted alkyl" unless otherwise specified is used herein to refer to an alkyl group, of from 1 to 10 carbon atoms, preferably, 1 to 5 carbon atoms, having from 1 to 5 substituents, preferably 1 to 3 substituents, independently selected from the group consisting of alkoxy, substituted alkoxy, acyl, acylamino, acyloxy, amino, substituted amino, aminoacyl, aminocarbonylamino, aminothiocarbonylamino, aminocarbonyloxy, aryl, substituted aryl, aryloxy, substituted aryloxy, aryloxyaryl, substituted aryloxyaryl, cyano, halogen, hydroxyl, nitro, oxo, thioxo, carboxyl, carboxyl esters, cycloalkyl, substituted cycloalkyl, thiol, alkylthio, substituted alkylthio, arylthio, substituted arylthio, cycloalkylthio, substituted cycloalkylthio, heteroarylthio, substituted heteroarylthio, heterocyclicthio, substituted heterocyclicthio, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, $-OS(O)_2$-alkyl, $-OS(O)_2$-substituted alkyl, $-OS(O)_2$-aryl, $-OS(O)_2$-substituted aryl, $OS(O)_2$-heteroaryl, $-OS(O)_2$-substituted heteroaryl, $-OS(O)_2$-heterocyclic, $-OS(O)_2$-substituted heterocyclic, $-OSO_2-$ $NR^{40}R^{40}$ where each $R^{40}$ is hydrogen or alkyl, $-NR^{40}$ $S(O)_2$-alkyl, $-NR^{40}S(O)_2$-substituted alkyl, $-NR^{40}S(O)_2$-aryl, $-NR^{40}S(O)_2$-substituted aryl, $-NR^{40}S(O)_2$-heteroaryl, $-NR^{40}S(O)_2$-substituted heteroaryl, $-NR^{40}S(O)_2$-heterocyclic, $-NR^{40}S(O)_2$-substituted heterocyclic, $-NR^{40}S(O)_2-NR^4$-alkyl, $-NR\ S(O)_2-NR^{40}$-substituted alkyl, $-NR^{40}S(O)_2-NR^{40}$-aryl, $-NR^{40}S(O)_2-NR^{40}$-substituted aryl, $-NR^{40}S(O)_2-NR^{40}$-heteroaryl, $-NR^{40}S$ $(O)_2-NR^{40}$-substituted heteroaryl, $-NR^{40}S(O)_2-NR^{40}$-heterocyclic, and $-NR^{40}S(O)_2-NR^{40}$-substituted heterocyclic where each $R^{40}$ is hydrogen or alkyl.

"Alkoxy" unless otherwise specified is used herein to refer to the group "alkyl-O—" which includes, by way of example, methoxy, ethoxy, n-propoxy, iso-propoxy, n-butoxy, t-butoxy, sec-butoxy, n-pentoxy and the like.

"Substituted alkoxy" unless otherwise specified is used herein to refer to the group "substituted alkyl-O-".

"Acyl" unless otherwise specified is used herein to refer to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, heteroaryl-C(O)—, substituted heteroaryl-C(O), heterocyclic-C(O)—, and substituted heterocyclic-C(O)— provided that a nitrogen atom of the heterocyclic or substituted heterocyclic is not bound to the —C(O)— group wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

The terms "aminoacyl" or, as a prefix, "carbamoyl" or "carboxamide," or "substituted carbamoyl," or "substituted carboxamide," are used herein unless otherwise specified to refer to the group $-C(O)NR^{142}R^{142}$ where each $R^{142}$ is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each $R^{142}$ is joined to form together with the nitrogen atom a heterocyclic or substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" unless otherwise specified is used herein to refer to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Alkenyl" unless otherwise specified is used herein to refer to alkenyl group preferably having from 2 to 6 carbon atoms and more preferably 2 to 4 carbon atoms and having at least 1 and preferably from 1 to 2 sites of alkenyl unsaturation.

"Substituted alkenyl" unless otherwise specified is used herein to refer to alkenyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic.

"Alkynyl" unless otherwise specified is used herein to refer to alkynyl group preferably having from 2 to 6 carbon atoms and more preferably 2 to 3 carbon atoms and having at least 1 and preferably from 1-2 sites of alkynyl unsaturation.

"Substituted alkynyl" unless otherwise specified is used herein to refer to alkynyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic.

"Amino" refers to the group $-NH_2$.

"Substituted amino" unless otherwise specified is used herein to refer to the group $-NR^{141}R^{141}$, where each $R^{141}$ group is independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, substituted heterocyclic, $-SO_2$-alkyl, $-SO_2$-substituted alkyl, $-SO_2$-alkenyl, $-SO_2$-substituted alkenyl, $-SO_2$-cycloalkyl, $-SO_2$-substituted cycloalkyl, $-SO_2$-aryl, $-SO_2$-substituted aryl, $-SO_2$-heteroaryl, $-SO_2$-substituted heteroaryl, $-SO_2$-heterocyclic, $-SO_2$-substituted heterocyclic, provided that both $R^{141}$ groups are not hydrogen; or the $R^{141}$ groups can be joined together with the nitrogen atom to form a heterocyclic or substituted heterocyclic ring.

"Acylamino" unless otherwise specified is used herein to refer to the groups $-NR^{145}C(O)$alkyl, $-NR^{145}C(O)$substituted alkyl, $-NR^{145}C(O)$cycloalkyl, $-NR^{145}C(O)$substituted cycloalkyl, $-NR^{145}C(O)$alkenyl, $-NR^{145}C(O)$substituted alkenyl, —NR$^{45}$C(O)alkynyl, —NR$^{145}$C(O) substituted alkynyl, —NR$^{145}$C(O)aryl, —NR$^{145}$C(O) substituted aryl, —NR$^{145}$C(O)heteroaryl, —NR$^{145}$C(O) substituted heteroaryl, —NR$^{145}$C(O)heterocyclic, and —NR$^{145}$C(O)substituted heterocyclic where R$^{145}$ is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are defined herein.

"Carbonyloxyamino" unless otherwise specified is used herein to refer to the groups —NR$^{146}$C(O)O-alkyl, —NR$^{146}$C(O)O-substituted alkyl, —NR$^{146}$C(O)O-alkenyl, —NR$^{46}$C(O)O-substituted alkenyl, —NR$^{146}$C(O)O-alkynyl, —NR$^{146}$C(O)O-substituted alkynyl, —NR$^{146}$C(O)O-cycloalkyl, —NR$^{146}$C(O)O-substituted cycloalkyl, —NR$^{146}$C(O)O-aryl, —NR$^{146}$C(O)O-substituted aryl, —NR$^{146}$C(O)O-heteroaryl, —NR$^{146}$C(O)O-substituted heteroaryl, —NR$^{146}$C(O)O-heterocyclic, and —NR$^{146}$C(O)O-substituted heterocyclic where R$^{146}$ is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonyloxy," or, as a prefix, "carbamoyloxy," or "substituted carbamoyloxy," are used herein unless otherwise specified to refer to the groups —OC(O)NR$^{147}$R$^{147}$ where each R$^{147}$ is independently hydrogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic or where each R$^{147}$ is joined to form, together with the nitrogen atom a heterocyclic or substituted heterocyclic and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonylamino" unless otherwise specified is used herein to refer to the group —NR$^{149}$C(O)NR$^{149}$— where R$^{149}$ is selected from the group consisting of hydrogen and alkyl.

"Aryl" or "Ar" unless otherwise specified are used herein to refer to a monovalent aromatic carbocyclic group of from 6 to 14 carbon atoms having a single ring (e.g., phenyl) or multiple condensed rings (e.g., naphthyl or anthryl), which condensed rings may or may not be aromatic (e.g., 2-benzoxazolinone, 2H-1,4-benzoxazin-3(4H)-one-7-yl, and the like), provided that the point of attachment is the aryl group. Preferred aryls include phenyl and naphthyl.

"Substituted aryl" unless otherwise specified is used herein to refer to aryl groups, as defined herein, which are substituted with from 1 to 4, preferably 1-3, substituents selected from the group consisting of hydroxy, acyl, acylamino, carbonylaminothio, acyloxy, alkyl, substituted alkyl, alkoxy, substituted alkoxy, alkenyl, substituted alkenyl, alkynyl, substituted alkynyl, amidino, amino, substituted amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxyl esters cyano, thiol, alkylthio, substituted alkylthio, arylthio, substituted arylthio, heteroarylthio, substituted heteroarylthio, cycloalkylthio, substituted cycloalkylthio, heterocyclicthio, substituted heterocyclicthio, cycloalkyl, substituted cycloalkyl, guanidino, halo, nitro, heteroaryl, substituted heteroaryl, heterocyclic, substituted heterocyclic, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NR$^{151}$R$^{151}$ where each R$^{151}$ is hydrogen or alkyl, —NR$^{151}$S(O)$_2$-alkyl, —NR$^{151}$S(O)$_2$-substituted alkyl, —NR$^{151}$S(O)$_2$-aryl, —NR$^{151}$S(O)$_2$-substituted aryl, —NR$^{151}$S(O)$_2$-heteroaryl, —NR$^{151}$S(O)$_2$-substituted heteroaryl, —NR$^{151}$S(O)$_2$-heterocyclic, —NR$^{151}$S(O)$_2$-substituted heterocyclic, —NR$^{151}$S(O)$_2$—NR$^{151}$-alkyl, —NR$^{151}$S(O)$_2$—NR$^{151}$-substituted alkyl, —NR$^{151}$S(O)$_2$—NR$^{151}$-aryl, —NR$^{151}$S(O)$_2$—NR$^{151}$-substituted aryl, —NR$^{151}$S(O)$_2$—NR$^{151}$-heteroaryl, —NR$^{151}$S(O)$_2$—NR$^{151}$-substituted heteroaryl, —NR$^{151}$S(O)$_2$—NR$^{151}$-heterocyclic, —NR$^{151}$S(O)$_2$—NR$^{151}$-substituted heterocyclic where each R$^{151}$ is hydrogen or alkyl, wherein each of the terms is as defined herein.

"Aryloxy" unless otherwise specified is used herein to refer to the group aryl-O— that includes, by way of example, phenoxy, naphthoxy, and the like.

"Substituted aryloxy" unless otherwise specified is used herein to refer to substituted aryl-O— groups.

"Aryloxyaryl" unless otherwise specified is used herein to refer to the group -aryl-O-aryl.

"Substituted aryloxyaryl" unless otherwise specified is used herein to refer to aryloxyaryl groups substituted with from 1 to 3 substituents on either or both aryl rings as defined above for substituted aryl.

"Carboxyl" refers to —COOH or salts thereof.

"Carboxyl esters" unless otherwise specified is used herein to refer to the groups —C(O)O-alkyl, —C(O)O-substituted alkyl, —C(O)O-aryl, and —C(O)O-substituted aryl wherein alkyl, substituted alkyl, aryl and substituted aryl are as defined herein.

"Cycloalkyl" unless otherwise specified is used herein to refer to cyclic alkyl groups of from 3 to 10 carbon atoms having single or multiple cyclic rings including, by way of example, adamantyl, cyclopropyl, cyclobutyl, cyclopentyl, cyclooctyl and the like.

"Substituted cycloalkyl" unless otherwise specified is used herein to refer to a cycloalkyl group, having from 1 to 5 substituents selected from the group consisting of oxo (=O), thioxo (=S), alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic.

"Cycloalkoxy" unless otherwise specified is used herein to refer to —O-cycloalkyl groups.

"Substituted cycloalkoxy" unless otherwise specified is used herein to refer to —O-substituted cycloalkyl groups.

"Halo" or "halogen" refer to fluoro, chloro, bromo and iodo and, preferably, fluoro or chloro.

"Heteroaryl" unless otherwise specified is used herein to refer to an aromatic group of from 1 to 15 carbon atoms, preferably from 1 to 10 carbon atoms, and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl). Preferred heteroaryls include pyridinyl, pyrrolyl, indolyl, thiophenyl, and furyl.

"Substituted heteroaryl" unless otherwise specified is used herein to refer to heteroaryl groups that are substituted with from 1 to 3 substituents selected from the same group of substituents defined for substituted aryl.

"Heteroaryloxy" unless otherwise specified is used herein to refer to the group —O-heteroaryl and "substituted heteroaryloxy" refers to the group —O-substituted heteroaryl.

"Heterocycle" or "heterocyclic" unless otherwise specified are used herein to refer to a saturated or unsaturated group having a single ring or multiple condensed rings, from 1 to 10 carbon atoms and from 1 to 4 hetero atoms selected from the group consisting of nitrogen, sulfur or oxygen within the ring wherein, in fused ring systems, one or more the rings can be aryl or heteroaryl provided that the point of attachment is at the heterocycle.

"Substituted heterocyclic" unless otherwise specified is used herein to refer to heterocycle groups that are substituted with from 1 to 3 of the same substituents as defined for substituted cycloalkyl.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydro-isoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), piperidinyl, pyrrolidine, tetrahydrofuranyl, and the like.

"Heterocyclyloxy" unless otherwise specified is used herein to refer to the group —O-heterocyclic and "substituted heterocyclyloxy" refers to the group —O-substituted heterocyclic.

"Thiol" or "mercapto" refer to the group —SH.

"Alkylsulfanyl" and "alkylthio" unless otherwise specified are used herein to refer to the groups —S-alkyl where alkyl is as defined above.

"Substituted alkylthio" and "substituted alkylsulfanyl" unless otherwise specified are used herein to refer to the group —S-substituted alkyl is as defined above.

"Cycloalkylthio" or "cycloalkylsulfanyl" unless otherwise specified are used herein to refer to the groups —S-cycloalkyl where cycloalkyl is as defined above.

"Substituted cycloalkylthio" unless otherwise specified is used herein to refer to the group —S-substituted cycloalkyl where substituted cycloalkyl is as defined above.

"Arylthio" unless otherwise specified is used herein to refer to the group —S-aryl and "substituted arylthio" unless otherwise specified is used herein to refer to the group —S-substituted aryl where aryl and substituted aryl are as defined above.

"Heteroarylthio" unless otherwise specified is used herein to refer to the group —S-heteroaryl and "substituted heteroarylthio" unless otherwise specified is used herein to refer to the group —S-substituted heteroaryl where heteroaryl and substituted heteroaryl are as defined above.

"Heterocyclicthio" unless otherwise specified is used herein to refer to the group —S-heterocyclic and "substituted heterocyclicthio" unless otherwise specified is used herein to refer to the group —S-substituted heterocyclic where heterocyclic and substituted heterocyclic are as defined above.

The term "amino acid" refers to any of the naturally occurring amino acids, as well as synthetic analogs (e.g., D-stereoisomers of the naturally occurring amino acids, such as D-threonine) and derivatives thereof. α-Amino acids comprise a carbon atom to which is bonded an amino group, a carboxyl group, a hydrogen atom, and a distinctive group referred to as a "side chain". The side chains of naturally occurring amino acids are well known in the art and include, for example, hydrogen (e.g., as in glycine), alkyl (e.g., as in alanine, valine, leucine, isoleucine, proline), substituted alkyl (e.g., as in threonine, serine, methionine, cysteine, aspartic acid, asparagine, glutamic acid, glutamine, arginine, and lysine), arylalkyl (e.g., as in phenylalanine and tryptophan), substituted arylalkyl (e.g., as in tyrosine), and heteroarylalkyl (e.g., as in histidine). Unnatural amino acids are also known in the art, as set forth in, for example, Williams (ed.), Synthesis of Optically Active .alpha.-Amino Acids, Pergamon Press (1989); Evans et al., J. Amer. Chem. Soc., 112:4011-4030 (1990); Pu et al., J. Amer. Chem. Soc., 56:1280-1283 (1991); Williams et al., J. Amer. Chem. Soc., 113:9276-9286 (1991); and all references cited therein. The present invention includes the side chains of unnatural amino acids as well.

"Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

The term "prodrug" refers to compounds of this invention which have been modified to include a physiologically and biocompatible removable group which group is removed in vivo to provide for the active drug, a pharmaceutically acceptable salt thereof or a biologically active metabolite thereof. Suitable removable groups are well known in the art and particularly preferred removable groups include esters of the carboxylic acid moiety on the glycine substituent. Preferably such esters include those derived from alkyl alcohols, substituted alkyl alcohols, hydroxy substituted aryls and heteroaryls and the like. Another preferred removable group are the amides formed from the carboxylic acid moiety on the glycine substituent. Suitable amides are derived from amines of the formula HNR$^{20}$R$^{21}$ where R$^{20}$ and R$^{21}$ are independently hydrogen, alkyl, substituted alkyl, aryl, substituted aryl, and the like.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that, for example, substituted aryl groups are limited to -substituted aryl-(substituted aryl)-substituted aryl.

Similarly, it is understood that the above definitions are not intended to include impermissible substitution patterns (e.g., methyl substituted with 5 fluoro groups or a hydroxyl group alpha to ethenylic or acetylenic unsaturation). Such impermissible substitution patterns are well known to the skilled artisan.

Methods for Identifying Compounds

Methods for identifying compounds of the invention are also provided. Assays for hydroxylase activity are standard in the art. Such assays can directly or indirectly measure hydroxylase activity. For example, an assay can measure hydroxylated residues, e.g., proline, asparagine, etc., present in the enzyme substrate, e.g., a target protein, a synthetic peptide mimetic, or a fragment thereof. (See, e.g., Palmerini et al. (1985) J Chromatogr 339:285-292.) A reduction in hydroxylated residue, e.g., proline or asparagine, in the presence of a compound is indicative of a compound that inhibits hydroxylase activity. Alternatively, assays can measure other products of the hydroxylation reaction, e.g., formation of succinate from 2-oxoglutarate. (See, e.g., Cunliffe et al. (1986) Biochem J 240:617-619.) Kaule and Gunzler (1990; Anal Biochem 184:291-297) describe an exemplary procedure that measures production of succinate from 2-oxoglutarate.

Procedures such as those described above can be used to identify compounds that modulate HIF hydroxylase activity. Target protein may include HIFA or a fragment thereof, e.g., HIF(556-575). Enzyme may include, e.g., HIF prolyl hydroxylase (see, e.g., GenBank Accession No. AAG33965, etc.) or HIF asparaginyl hydroxylase (see, e.g., GenBank Accession No. AAL27308, etc.), obtained from any source. Enzyme may also be present in a crude cell lysate or in a partially purified form. For example, procedures that measure HIF hydroxylase activity are described in Ivan et al. (2001, Science 292:464-468; and 2002, Proc Natl Acad Sci USA 99:13459-13464) and Hirsila et al. (2003, J Biol Chem 278: 30772-30780); additional methods are described in International Publication No. WO 03/049686. Measuring and comparing enzyme activity in the absence and presence of the compound will identify compounds that inhibit hydroxylation of HIFα.

For clarity, an agent for use in the present methods is any compound that stabilizes HIFα. Methods for determining whether or not a particular agent stabilizes HIFα are available in the art and are described, supra.

Modes of Administration

The compositions of the present invention can be delivered directly or in pharmaceutical compositions containing excipients, as is well known in the art. The present methods of treatment involve administration of an effective amount of a compound of the present invention to a subject having or at risk for having chemotherapy-induced anemia.

An effective amount, e.g., dose, of compound or drug can readily be determined by routine experimentation, as can an effective and convenient route of administration and an appropriate formulation. Various formulations and drug delivery systems are available in the art. (See, e.g., Gennaro, ed. (2000) Remington's Pharmaceutical Sciences, supra; and Hardman, Limbird, and Gilman, eds. (2001) The Pharmacological Basis of Therapeutics, supra.)

Suitable routes of administration may, for example, include oral, rectal, topical, nasal, pulmonary, ocular, intestinal, and parenteral administration. Primary routes for parenteral administration include intravenous, intramuscular, and subcutaneous administration. Secondary routes of administration include intraperitoneal, intra-arterial, intra-articular, intracardiac, intracisternal, intradermal, intralesional, intraocular, intrapleural, intrathecal, intrauterine, and intraventricular administration. The indication to be treated, along with the physical, chemical, and biological properties of the drug, dictate the type of formulation and the route of administration to be used, as well as whether local or systemic delivery would be preferred.

In preferred embodiments, the compounds of the present invention are administered orally. For example, in certain embodiments, the invention provides for oral administration of a compound selected from the group consisting of: Compound A [(1 Chloro-4-hydroxy-isoquinoline-3-carbonyl)-amino]-acetic acid]; Compound B [((S)-2-[(4-Hydroxy-7-phenoxy-6,7-dihydro-isoquinoline-3-carbonyl)-amino]-propionic acid]; Compound C [{[4-Hydroxy-7-(4-methoxy-phenoxy)-isoquinoline-3-carbonyl]-amino}-acetic acid]; Compound D [[(4-Hydroxy-1-methyl-7-phenoxy-isoquinoline-3-carbonyl)-amino]-acetic acid]; Compound E [[7-(4-Fluoro-phenoxy)-4-hydroxy-isoquinoline-3-carbonyl]-amino-acetic acid]; Compound F [4-Oxo-1,4-dihydro-[1,10] phenanthroline-3-carboxylic acid], Compound G [3-{[4-(3, 3-Dibenzyl-ureido)-benzenesulfonyl]-[2-(4-methoxy-phenyl)-ethyl]-amino}-N-hydroxy-propionamide], Compound H [[(7-Chloro-3-hydroxy-quinoline-2-carbonyl)-amino]-acetic acid], Compound I [[(1-Chloro-4-hydroxy-7-methoxy-isoquinoline-3-carbonyl)-amino]-acetic acid], Compound J [[(6,7-Dichloro-4-hydroxy-isoquinoline-3-carbonyl)-amino]-acetic acid], Compound K [[(4-Hydroxy-7-phenoxy-isoquinoline-3-carbonyl)-amino]-acetic acid], Compound L [(S)-2-[(4-Hydroxy-7-phenylsulfanyl-isoquinoline-3-carbonyl)-amino]-propionic acid], Compound M [[(4-Hydroxy-1,7-diphenoxy-isoquinoline-3-carbonyl)-amino]-acetic acid], and Compound N [(4-hydroxy-7-phenylsulfanyl-isoquinoline-3-carbonyl)-amino]-acetic acid.

Pharmaceutical dosage forms of a compound of the invention may be provided in an instant release, controlled release, sustained release, or target drug-delivery system. Commonly used dosage forms include, for example, solutions and suspensions, (micro-) emulsions, ointments, gels and patches, liposomes, tablets, dragees, soft or hard shell capsules, suppositories, ovules, implants, amorphous or crystalline powders, aerosols, and lyophilized formulations. Depending on route of administration used, special devices may be required for application or administration of the drug, such as, for example, syringes and needles, inhalers, pumps, injection pens, applicators, or special flasks. Pharmaceutical dosage forms are often composed of the drug, an excipient(s), and a container/closure system. One or multiple excipients, also referred to as inactive ingredients, can be added to a compound of the invention to improve or facilitate manufacturing, stability, administration, and safety of the drug, and can provide a means to achieve a desired drug release profile. Therefore, the type of excipient(s) to be added to the drug can depend on various factors, such as, for example, the physical and chemical properties of the drug, the route of administration, and the manufacturing procedure. Pharmaceutically acceptable excipients are available in the art, and include those listed in various pharmacopoeias. (See, e.g., USP, JP, EP, and BP, FDA web page, Inactive Ingredient Guide 1996, and Handbook of Pharmaceutical Additives, ed. Ash; Synapse Information Resources, Inc. 2002.)

Pharmaceutical dosage forms of a compound of the present invention may be manufactured by any of the methods well-known in the art, such as, for example, by conventional mixing, sieving, dissolving, melting, granulating, dragee-making, tabletting, suspending, extruding, spray-drying, levigating, emulsifying, (nano/micro-) encapsulating, entrapping, or lyophilization processes. As noted above, the compositions of the present invention can include one or more physiologically acceptable inactive ingredients that facilitate processing of active molecules into preparations for pharmaceutical use.

Proper formulation is dependent upon the desired route of administration. For intravenous injection, for example, the composition may be formulated in aqueous solution, if necessary using physiologically compatible buffers, including, for example, phosphate, histidine, or citrate for adjustment of the formulation pH, and a tonicity agent, such as, for example, sodium chloride or dextrose. For transmucosal or nasal administration, semisolid, liquid formulations, or patches may be preferred, possibly containing penetration enhancers. Such penetrants are generally known in the art. For oral administration, the compounds can be formulated in liquid or solid dosage forms and as instant or controlled/sustained release formulations. Suitable dosage forms for oral ingestion by a subject include tablets, pills, dragees, hard and soft shell capsules, liquids, gels, syrups, slurries, suspensions, and emulsions. The compounds may also be formulated in rectal compositions, such as suppositories or retention enemas, e.g., containing conventional suppository bases such as cocoa butter or other glycerides.

Solid oral dosage forms can be obtained using excipients, which may include, fillers, disintegrants, binders (dry and wet), dissolution retardants, lubricants, glidants, antiadherants, cationic exchange resins, wetting agents, antioxidants, preservatives, coloring, and flavoring agents. These excipients can be of synthetic or natural source. Examples of such excipients include cellulose derivatives, citric acid, dicalcium phosphate, gelatine, magnesium carbonate, magnesium/sodium lauryl sulfate, mannitol, polyethylene glycol, polyvinyl pyrrolidone, silicates, silicium dioxide, sodium benzoate, sorbitol, starches, stearic acid or a salt thereof, sugars (i.e. dextrose, sucrose, lactose, etc.), talc, tragacanth mucilage, vegetable oils (hydrogenated), and waxes. Ethanol and water may serve as granulation aides. In certain instances, coating of tablets with, for example, a taste-masking film, a stomach acid resistant film, or a release-retarding film is desirable. Natural and synthetic polymers, in combination with colorants, sugars, and organic solvents or water, are often used to coat tablets, resulting in dragees. When a capsule is preferred over a tablet, the drug powder, suspension, or solution thereof can be delivered in a compatible hard or soft shell capsule.

In one embodiment, the compounds of the present invention can be administered topically, such as through a skin patch, a semi-solid or a liquid formulation, for example a gel, a (micro)-emulsion, an ointment, a solution, a (nano/micro)-suspension, or a foam. The penetration of the drug into the skin and underlying tissues can be regulated, for example, using penetration enhancers; the appropriate choice and combination of lipophilic, hydrophilic, and amphiphilic excipients, including water, organic solvents, waxes, oils, synthetic and natural polymers, surfactants, emulsifiers; by pH adjustment; and use of complexing agents. Other techniques, such as iontophoresis, may be used to regulate skin penetration of a compound of the invention. Transdermal or topical administration would be preferred, for example, in situations in which local delivery with minimal systemic exposure is desired.

For administration by inhalation, or administration to the nose, the compounds for use according to the present invention are conveniently delivered in the form of a solution, suspension, emulsion, or semisolid aerosol from pressurized packs, or a nebuliser, usually with the use of a propellant, e.g., halogenated carbons derived from methan and ethan, carbon dioxide, or any other suitable gas. For topical aerosols, hydrocarbons like butane, isobutene, and pentane are useful. In the case of a pressurized aerosol, the appropriate dosage unit may be determined by providing a valve to deliver a metered amount. Capsules and cartridges of, for example, gelatin, for use in an inhaler or insufflator, may be formulated. These typically contain a powder mix of the compound and a suitable powder base such as lactose or starch.

Compositions formulated for parenteral administration by injection are usually sterile and, can be presented in unit dosage forms, e.g., in ampoules, syringes, injection pens, or in multi-dose containers, the latter usually containing a preservative. The compositions may take such forms as suspensions, solutions, or emulsions in oily or aqueous vehicles, and may contain formulatory agents, such as buffers, tonicity agents, viscosity enhancing agents, surfactants, suspending and dispersing agents, antioxidants, biocompatible polymers, chelating agents, and preservatives. Depending on the injection site, the vehicle may contain water, a synthetic or vegetable oil, and/or organic co-solvents. In certain instances, such as with a lyophilized product or a concentrate, the parenteral formulation would be reconstituted or diluted prior to administration. Depot formulations, providing controlled or sustained release of a compound of the invention, may include injectable suspensions of nano/micro particles or nano/micro or non-micronized crystals. Polymers such as poly(lactic acid), poly(glycolic acid), or copolymers thereof, can serve as controlled/sustained release matrices, in addition to others well known in the art. Other depot delivery systems may be presented in form of implants and pumps requiring incision.

Suitable carriers for intravenous injection for the molecules of the invention are well-known in the art and include water-based solutions containing a base, such as, for example, sodium hydroxide, to form an ionized compound, sucrose or sodium chloride as a tonicity agent, for example, the buffer contains phosphate or histidine. Co-solvents, such as, for example, polyethylene glycols, may be added. These water-based systems are effective at dissolving compounds of the invention and produce low toxicity upon systemic administration. The proportions of the components of a solution system may be varied considerably, without destroying solubility and toxicity characteristics. Furthermore, the identity of the components may be varied.

For example, low-toxicity surfactants, such as polysorbates or poloxamers, may be used, as can polyethylene glycol or other co-solvents, biocompatible polymers such as polyvinyl pyrrolidone may be added, and other sugars and polyols may substitute for dextrose.

For composition useful for the present methods of treatment, a therapeutically effective dose can be estimated initially using a variety of techniques well-known in the art. Initial doses used in animal studies may be based on effective concentrations established in cell culture assays. Dosage ranges appropriate for human subjects can be determined, for example, using data obtained from animal studies and cell culture assays.

A therapeutically effective dose or amount of a compound, agent, or drug of the present invention refers to an amount or dose of the compound, agent, or drug that results in amelioration of symptoms or a prolongation of survival in a subject. Toxicity and therapeutic efficacy of such molecules can be determined by standard pharmaceutical procedures in cell cultures or experimental animals, e.g., by determining the LD50 (the dose lethal to 50% of the population) and the ED50 (the dose therapeutically effective in 50% of the population). The dose ratio of toxic to therapeutic effects is the therapeutic index, which can be expressed as the ratio LD50/ED50. Agents that exhibit high therapeutic indices are preferred.

The effective amount or therapeutically effective amount is the amount of the compound or pharmaceutical composition that will elicit the biological or medical response of a tissue, system, animal, or human that is being sought by the researcher, veterinarian, medical doctor, or other clinician, e.g., an increase in hemoglobin levels, an increase in hematocrit, amelioration of the symptoms of chemotherapy-induced anemia, etc.

Dosages preferably fall within a range of circulating concentrations that includes the ED50 with little or no toxicity. Dosages may vary within this range depending upon the dosage form employed and/or the route of administration utilized. The exact formulation, route of administration, dosage, and dosage interval should be chosen according to methods known in the art, in view of the specifics of a subject's condition.

Dosage amount and interval may be adjusted individually to provide plasma levels of the active moiety that are sufficient to achieve the desired effects, i.e., minimal effective concentration (MEC). The MEC will vary for each compound but can be estimated from, for example, in vitro data and animal experiments. Dosages necessary to achieve the MEC will depend on individual characteristics and route of administration. In cases of local administration or selective uptake, the effective local concentration of the drug may not be related to plasma concentration.

In some embodiment of the present invention, effective doses for preferred compounds of the invention (e.g., Compound A [(1 Chloro-4-hydroxy-isoquinoline-3-carbonyl)-amino]-acetic acid]; Compound B [((S)-2-[(4-Hydroxy-7-phenoxy-6,7-dihydro-isoquinoline-3-carbonyl)-amino]-propionic acid]; Compound C [{[4-Hydroxy-7-(4-methoxy-phenoxy)-isoquinoline-3-carbonyl]-amino}-acetic acid]; Compound D [[(4-Hydroxy-1-methyl-7-phenoxy-isoquinoline-3-carbonyl)-amino]-acetic acid]; Compound E [[7-(4-Fluoro-phenoxy)-4-hydroxy-isoquinoline-3-carbonyl]-amino-acetic acid]; Compound F [4-Oxo-1,4-dihydro-[1,10]phenanthroline-3-carboxylic acid], Compound G [3-{[4-(3,3-Dibenzyl-ureido)-benzenesulfonyl]-[2-(4-methoxy-phenyl)-ethyl]-amino}-N-hydroxy-propionamide], Compound H [[(7-Chloro-3-hydroxy-quinoline-2-carbonyl)-amino]-acetic acid], Compound I [[(1-Chloro-4-hydroxy-7-methoxy-isoquinoline-3-carbonyl)-amino]-acetic acid], Compound J [[(6,7-Dichloro-4-hydroxy-isoquinoline-3-carbonyl)-amino]-acetic acid], Compound K [[(4-Hydroxy-7-phenoxy-isoquinoline-3-carbonyl)-amino]-acetic acid], Compound L [(S)-2-[(4-Hydroxy-7-phenylsulfanyl-isoquinoline-3-carbonyl)-amino]-propionic acid], Compound M [[(4-Hydroxy-1,7-diphenoxy-isoquinoline-3-carbonyl)-amino]-acetic acid], and Compound N [(4-hydroxy-7-phenylsulfanyl-isoquinoline-3-carbonyl)-amino]-acetic acid) include 3 mg/kg, 6 mg/kg, 10 mg/kg, 15 mg/kg, 20 mg/kg and 30 mg/kg. These doses are therefore particularly preferred for use in the present invention.

In additional embodiments, effective treatment regimes for preferred compounds of the invention (e.g., Compound A [(1 Chloro-4-hydroxy-isoquinoline-3-carbonyl)-amino]-acetic acid]; Compound B [((S)-2-[(4-Hydroxy-7-phenoxy-6,7-dihydro-isoquinoline-3-carbonyl)-amino]-propionic acid]; Compound C [{[4-Hydroxy-7-(4-methoxy-phenoxy)-isoquinoline-3-carbonyl]-amino}-acetic acid]; Compound D [[(4-Hydroxy-1-methyl-7-phenoxy-isoquinoline-3-carbonyl)-amino]-acetic acid]; Compound E [[7-(4-Fluoro-phenoxy)-4-hydroxy-isoquinoline-3-carbonyl]-amino-acetic acid]; Compound F [4-Oxo-1,4-dihydro-[1,10]phenanthroline-3-carboxylic acid], Compound G [3-{[4-(3,3-Dibenzyl-ureido)-benzenesulfonyl]-[2-(4-methoxy-phenyl)-ethyl]-amino}-N-hydroxy-propionamide], Compound H [[(7-Chloro-3-hydroxy-quinoline-2-carbonyl)-amino]-acetic acid], Compound I [[(1-Chloro-4-hydroxy-7-methoxy-isoquinoline-3-carbonyl)-amino]-acetic acid], Compound J [[(6,7-Dichloro-4-hydroxy-isoquinoline-3-carbonyl)-amino]-acetic acid], Compound K [[(4-Hydroxy-7-phenoxy-isoquinoline-3-carbonyl)-amino]-acetic acid], Compound L [(S)-2-[(4-Hydroxy-7-phenylsulfanyl-isoquinoline-3-carbonyl)-amino]-propionic acid], Compound M [[(4-Hydroxy-1,7-diphenoxy-isoquinoline-3-carbonyl)-amino]-acetic acid], and Compound N [(4-hydroxy-7-phenylsulfanyl-isoquinoline-3-carbonyl)-amino]-acetic acid) include administration two or three times weekly. These regimes are therefore particularly preferred for use in the present invention.

The amount of agent or composition administered may be dependent on a variety of factors, including the sex, age, and weight of the subject being treated, the severity of the affliction, the manner of administration, and the judgment of the prescribing physician.

The present compositions may, if desired, be presented in a pack or dispenser device containing one or more unit dosage forms containing the active ingredient. Such a pack or device may, for example, comprise metal or plastic foil, such as a blister pack, or glass and rubber stoppers such as in vials. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

These and other embodiments of the present invention will readily occur to those of ordinary skill in the art in view of the disclosure herein.

EXAMPLES

The invention will be further understood by reference to the following examples, which are intended to be purely exemplary of the invention. These examples are provided solely to illustrate the claimed invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description. Such modifications are intended to fall within the scope of the appended claims.

The following non-limiting examples describe Compound A, a representative compound of the present invention, but it is specifically contemplated that other compounds, including Compound B [((S)-2-[(4-Hydroxy-7-phenoxy-6,7-dihydro-isoquinoline-3-carbonyl)-amino]-propionic acid]; Compound C [{[4-Hydroxy-7-(4-methoxy-phenoxy)-isoquinoline-3-carbonyl]-amino}-acetic acid]; Compound D [[(4-Hydroxy-1-methyl-7-phenoxy-isoquinoline-3-carbonyl)-amino]-acetic acid]; Compound E [[7-(4-Fluoro-phenoxy)-4-hydroxy-isoquinoline-3-carbonyl]-amino-acetic acid]; Compound F [4-Oxo-1,4-dihydro-[1,10]phenanthroline-3-carboxylic acid], Compound G [3-{[4-(3,3-Dibenzyl-ureido)-benzenesulfonyl]-[2-(4-methoxy-phenyl)-ethyl]-amino}-N-hydroxy-propionamide], Compound H [[(7-Chloro-3-hydroxy-quinoline-2-carbonyl)-amino]-acetic acid], Compound I [[(1-Chloro-4-hydroxy-7-methoxy-isoquinoline-3-carbonyl)-amino]-acetic acid], Compound J [[(6,7-Dichloro-4-hydroxy-isoquinoline-3-carbonyl)-amino]-acetic acid], Compound K [[(4-Hydroxy-7-phenoxy-isoquinoline-3-carbonyl)-amino]-acetic acid], Compound L [(S)-2-[(4-Hydroxy-7-phenylsulfanyl-isoquinoline-3-carbonyl)-amino]-propionic acid], Compound M [[(4-Hydroxy-1,7-diphenoxy-isoquinoline-3-carbonyl)-amino]-acetic acid], and Compound N [(4-hydroxy-7-phenylsulfanyl-isoquinoline-3-carbonyl)-amino]-acetic acid, can be used in the present methods.

Example 1

Compounds and Methods of the Invention Are Effective at Treating Chemotherapy-Induced Anemia The following study was performed to examine the effect of compounds and methods of the present invention on treatment of chemotherapy-induced anemia. Fifteen Sprague Dawley male rats (280-300 g) were obtained from Charles River Laboratories. On day 0, rats were treated by intraperitoneal (i.p.) injection with a single dose of saline (control; n=3) at 8 ml/kg, or Cisplatin (CP; Bedford Laboratories, Bedford Ohio) at either 7 mg/kg (7 ml/kg; n=6) or 10 mg/kg (10 ml/kg; n=6). Blood samples (0.2 ml) were collected on days 5, 9, and 16 as follows. Animals were anesthetized with isoflurane and 0.2 ml of blood was collected from the tail vein into a MICROTAINER EDTA-2K tube (Becton-Dickinson). Blood samples were processed for hematocrit as described above to determine the degree of anemia produced in each animal.

Beginning on day 19 of the study, one half of each cisplatin-treated group (n=3×2) and all of the control group were treated by oral gavage once per day for 5 consecutive days with a 2 ml/kg volume of 0.5% CMC (Sigma-Aldrich). The other half of each cisplatin-treated group (n=3×2) was treated by oral gavage once per day for five consecutive days with a 2 ml/kg volume of 2.5% of a representative compound of the present invention, Compound A (25 mg/ml in 0.5% CMC). Blood samples (0.5 ml) were collected as described above immediately prior to treatment and 4 days after treatment initiation. Blood samples were analyzed for CBC and reticulocyte counts as described above. On day 9 after initiation of oral treatment, a blood sample (0.1 ml) was collected and processed for hematocrit as described above.

As shown in FIG. 1A, administration of either 7 mg/kg cisplatin or 10 mg/kg cisplatin reduced hematocrit by 14% and 22%, respectively, compared to that in non-treated control animals. Administration of Compound A, however, increased hematocrit in the Cisplatin-treated animals 4 days after initiating treatment with Compound A. Hematocrit levels were significantly higher than non-treated counterparts by day 9 post-treatment. Specifically, hematocrit levels in animals initially exposed to 7 mg/kg cisplatin and subsequently treated with Compound A were at or above hematocrit levels in non-treated control (i.e., no chemotherapeutic agent administration) by day 9.

Figure 1B:
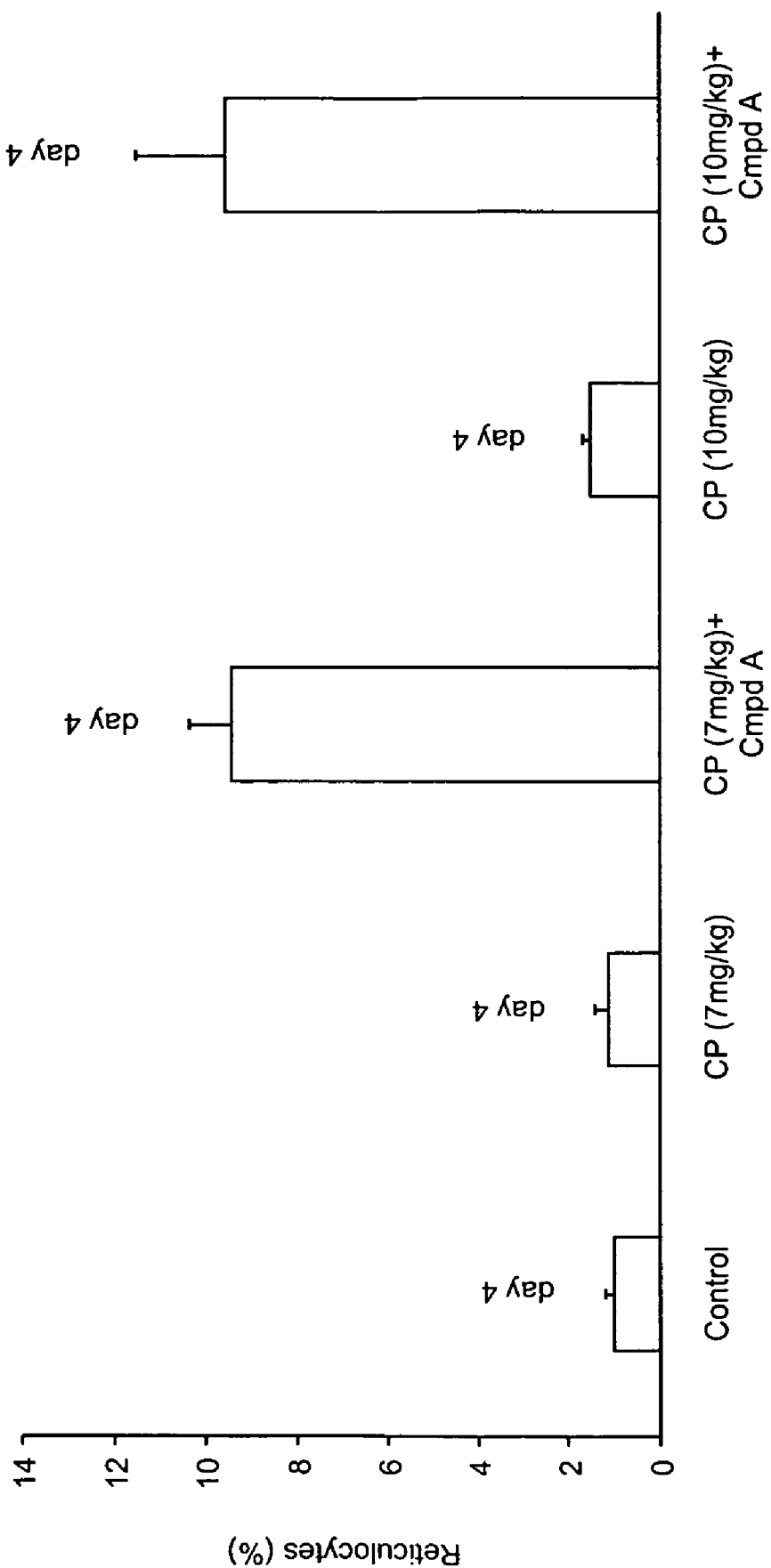

As shown in FIG. 1B, administration of Compound A to animals treated with the chemotherapy agent Cisplatin increased the percent circulating reticulocytes compared to cicplatin-treated animals without treatment with Compound A.

These results showed that methods and compounds of the present invention increased hematocrit and reticulocyte counts in an animal model of chemotherapy-induced anemia. Therefore, the present compounds and methods are effective at treating chemotherapy-induced anemia.

Example 2

Compounds and Methods of the Invention Are Effective at Treating Chemotherapy-Induced Anemia To examine the effect of methods and compounds of the present invention on treatment of chemotherapy-induced anemia, the following study was performed. The human H-460 lung cancer cell line used was obtained from the National Cancer Institute. (Brower et al., (1986) Cancer Res 46:798-806.) Animals were maintained in a HEPA-filtered environment during the experimental period. Cages, food, and bedding were autoclaved. Animal diets were obtained from Harlan Teklad (Madison, Wis.). Hydrochloric acid, 0.15% (v/v), was added to the drinking water.

Compounds of the invention were pre-formulated in an aqueous vehicle consisting of 0.1% (w/w) Polysorbate 80 (JT Baker) and 0.5% (w/w) high viscosity carboxymethyl cellulose sodium (Spectrum) to achieve a final 10 ml/kg dosing (oral gavage).

A stock tumor was established by subcutaneously injecting a cell suspension into nude mice. The resulting tumor was maintained in nude mice subcutaneously as tumor stock prior to use. Tumor implantation was performed when the stock tumors were in log phase of growth. Before implantation, tumor tissue was harvested from stock mice and placed in RPMI-1640 medium. Necrotic tissues were dissected away and viable tissues were cut into 1-2 $mm^2$ pieces. In these experiments, $1 \times 10^7$ H460 tumor cells were implanted subcutaneously to the flanks of female Harlan nude mice.

Treatment (administration of compounds of the present invention) was initiated when the inoculated tumors reached approximately 100 $mm^3$, and continued for four weeks.

These studies followed the guidelines of the Tumor Growth Delay (TGD) type, using a protocol that required individual animals to be humanely euthanized after reaching a set endpoint of tumor volume greater than or equal to 2 cc. At this endpoint, blood was also sampled and hematocrit (HCT) was determined.

Animals were administered Compound A (60 mg/kg) with or without additional administration of one of the chemotherapeutic agents paclitaxel or carboplatin. These two chemotherapeutic are representative of two broad classes of conventional anti-tumor therapeutics: microtubule poisons (Paclitaxcel); and DNA-directed agents, including the sub-classification of DNA alkylating agents (Carboplatin). In tumor-bearing human patients, conventional anti-tumor therapy commonly use one or both classes of chemotherapeutic agents.

Combined treatment groups (i.e., treatment with both Paclitaxel and Compound A or treatment with both Carboplatin and Compound A) were administered compound of the present invention and chemotherapeutic agents on different days. The study was initiated with administration of the chemotherapeutic agent or vehicle control, and followed one day later with administration of Compound A or vehicle control.

Treatment was continued over a course of 62 days. (See Table 1 and Table 2 for compound and chemotherapeutic agent dosing schedule.)

TABLE 1

| 1 Drug/Testing Agent | | | |
| --- | --- | --- | --- |
| Agent | mg/kg | Route | Schedule |
| 5% EC in D5W | — | i.v. | (q.o.d × 3) weekly start Day 1 |
| 5% EC in D5W | — | i.v. | (q.o.d × 3) weekly start Day 1 |
| Paclitaxel | 15 | i.v. | (q.o.d × 3) weekly start Day 1 |
| Carboplatin | 120 | i.p. | Q7d to end start Day 1 |
| Paclitaxel | 15 | i.v. | (q.o.d × 3) weekly start Day 1 |
| Carboplatin | 120 | i.p. | Q7d to end start Day 1 |

5% EC in D5W (5% Ethanol, 5% Cremophor EL, 90% D5W
D5W (Dextrose 5% in water (i.v. vehicle))
QOD (Quaque Other Die, every other day)
Q7D (every seventh day)

TABLE 2

| | 2 Drug/Testing Agent | | |
|---|---|---|---|
| Agent | mg/kg | Route | Schedule |
| vehicle | — | p.o. | (q.o.d × 3) weekly start Day 2 |
| Cmpd A | 60 | p.o. | (q.o.d × 3) weekly start Day 2 |
| vehicle | — | p.o. | (q.o.d × 3) weekly start Day 2 |
| vehicle | — | p.o. | (q.o.d × 3) weekly start Day 2 |
| Cmpd A | 60 | p.o. | (q.o.d × 3) weekly start Day 2 |
| Cmpd A | 60 | p.o. | (q.o.d × 3) weekly start Day 2 |

QOD (Quaque Other Die, every other day)

Administration of chemotherapeutic agents is associated with toxicity and premature morbidity. The Carboplatin treatment schedule used in these studies was excessive. Premature morbidity was observed in Carboplatin treatment groups only. (See Table 3.) When Carboplatin administration was combined with administration of Compound A, an improvement in morbidity was observed, as shown in Table 3. These results indicated that compounds and methods of the present invention are useful for reducing toxic effects of chemotherapy, including premature morbidity.

TABLE 3

| Group | # animals reaching study endpoint | # animals morbid prematurely |
|---|---|---|
| i.v. vehicle and p.o. vehicle | 10/10 | 0/10 |
| i.v. vehicle and Cmpd A | 10/10 | 0/10 |
| Carboplatin and p.o. vehicle | 4/10 | 6/10 |
| Carboplatin and Cmpd A | 6/10 | 4/10 |

Figure 2:
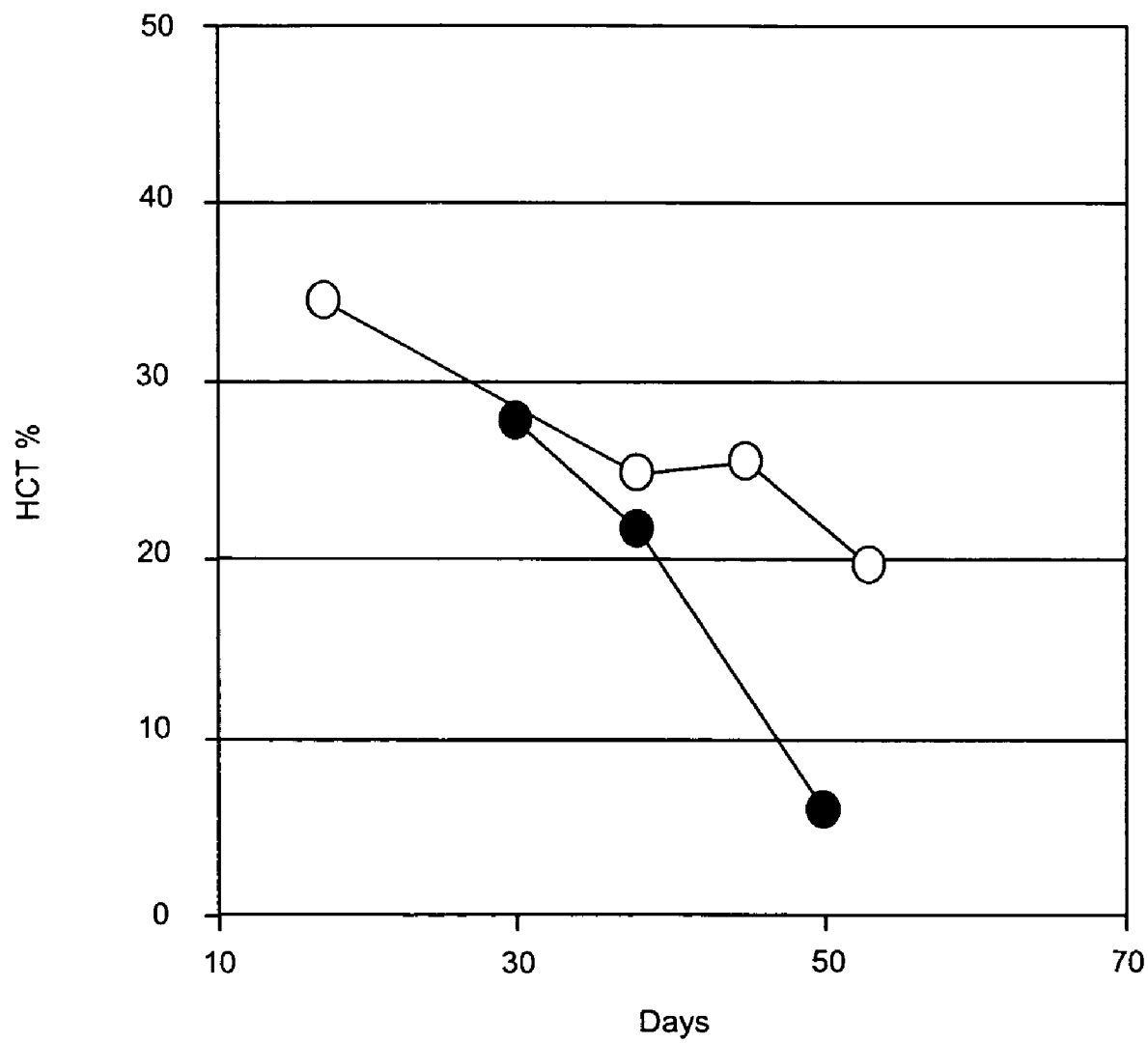
FIG. 2 sets forth data showing methods and compounds of the present invention increased hematocrit in an animal model of chemotherapy-induced anemia.

Administration of chemotherapeutic agents is also associated with the development of anemia. As shown in FIG. 2, animals administered Carboplatin displayed a significant decrease in hematocrit over time (closed circles in FIG. 2), indicative of anemia induced by chemotherapy administration. Administration of Carboplatin and Compound A resulted in a reduction of the extent of decrease in hematocrit compared to the decrease in hematocrit observed in animals administered Carboplatin alone (open circles in FIG. 2).

These results demonstrated that methods and compounds of the present invention were effective at treating chemotherapy-induced anemia.

Example 3

Compounds and Methods of the Invention Limit Weight Loss Associated with Chemotherapy To examine the effects of compounds and methods of the present invention on weight loss associated with chemotherapeutic agents, the following study was performed. This experiment was carried out essentially as described above in Example 2. The human H-460 lung cancer cell line used was obtained from the National Cancer Institute. (Brower et al., (1986) Cancer Res 46:798-806.) Animals were maintained in a HEPA-filtered environment during the experimental period. Cages, food, and bedding were autoclaved. Animal diets were obtained from Harlan Teklad (Madison, Wis.). Hydrochloric acid, 0.15% (v/v), was added to the drinking water.

Compounds of the invention were pre-formulated in an aqueous vehicle consisting of 0.1% (w/w) Polysorbate 80 (JT Baker) and 0.5% (w/w) high viscosity carboxymethyl cellulose sodium (Spectrum) to achieve a final 10 ml/kg dosing (oral gavage).

A stock tumor was established by subcutaneously injecting a cell suspension into nude mice. The resulting tumor was maintained in nude mice subcutaneously as tumor stock prior to use. Tumor implantation was performed when the stock tumors were in log phase of growth. Before implantation, tumor tissue was harvested from stock mice and placed in RPMI-1640 medium. Necrotic tissues were dissected away and viable tissues were cut into 1-2 mm$^2$ pieces. In these experiments, $1 \times 10^7$ H-460 tumor cells were implanted subcutaneously to the flanks of female Harlan nude mice.

Treatment (administration of compounds of the present invention) was initiated when the inoculated tumors reached approximately 100 mm$^3$, and continued for four weeks.

Animals were administered Compound A (60 mg/kg) with or without additional administration of one of the chemotherapeutic agents paclitaxel or carboplatin. These two chemotherapeutic are representative of two broad classes of conventional anti-tumor therapeutics: microtubule poisons (Paclitaxcel); and DNA-directed agents, including the sub-classification of DNA alkylating agents (Carboplatin). In tumor-bearing human patients, conventional anti-tumor therapy commonly use of one or both classes of chemotherapeutic agents.

Body weights were monitored over time for individual animals. Changes in individual animal body weights over time are shown in FIGS. 3-8, and are presented as percent of initial body weight (treatment day 1), which was set at 100%.

Figure 3:
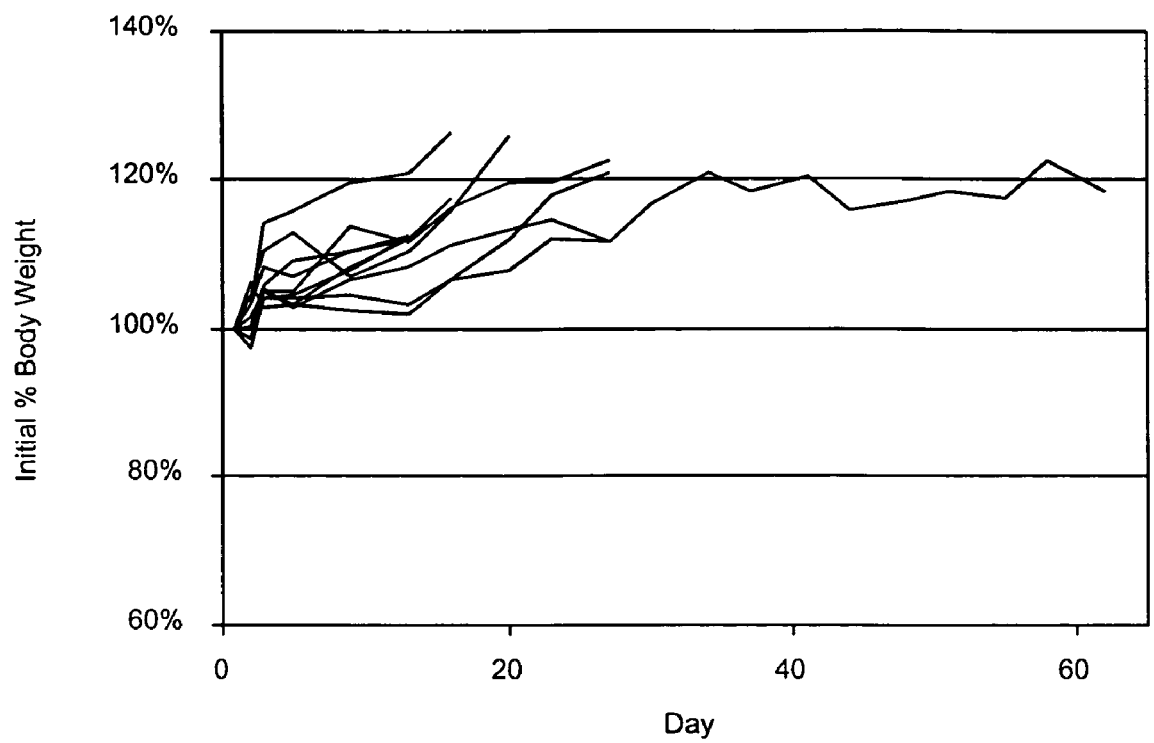
FIG. 3 sets forth data showing increases in body weights of animals over time.
Figure 4:
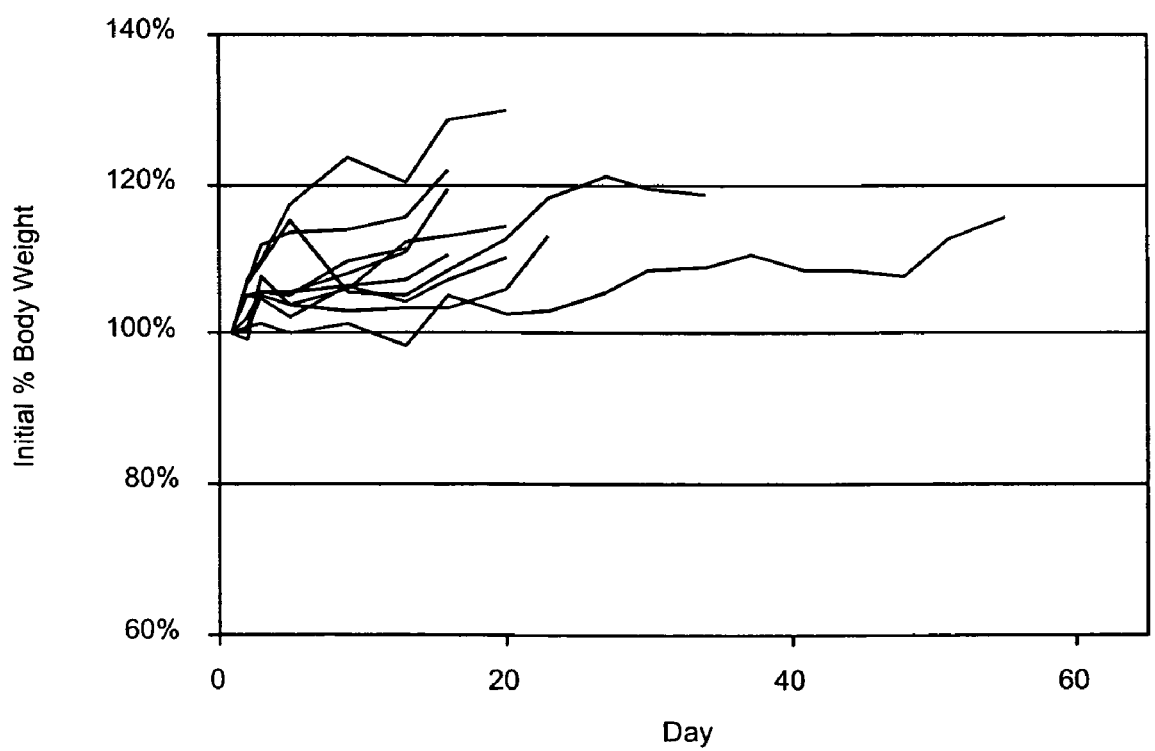
FIG. 4 sets forth data showing body weights of animals increased over time in animals treated with a compound of the present invention.

As shown in FIG. 3 and FIG. 4, body weights of animals administered vehicle control (FIG. 3) or Compound A (FIG. 4) increased gradually during the time course of the study. All animals administered either vehicle control or Compound A ended the study with an overall net weight gain.

Animals administered either chemotherapeutic agent (Paclitaxel or Carboplatin) displayed a pattern of weight loss compared to that of non-treated vehicle control animals. (Compare FIG. 3 (vehicle) with FIG. 5 (Paclitaxel); compare FIG. 3 (vehicle) with FIG. 7 (Carboplatin). In addition, not only did administration of either chemotherapeutic agent limit or reduce weight gain (e.g., limit or reduce growth) in animals, a number of animals treated with either chemotherapeutic agent ended the study with body weights below their respective starting body weights. These results indicated that, in addition to being associated with the development of anemia, administration of chemotherapeutic agents was associated with weight loss and reduced growth.

Figure 5:
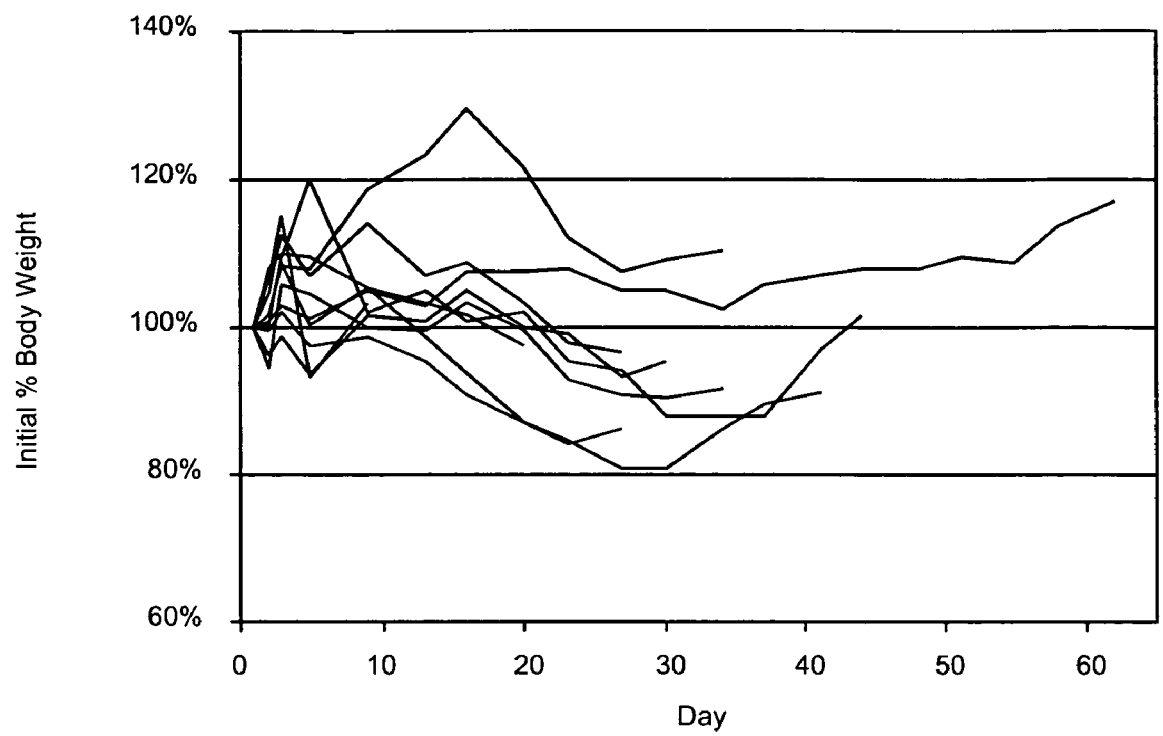
FIG. 5 sets forth data showing body weight loss in animals administered the chemotherapeutic agent Paclitaxel.
Figure 6:
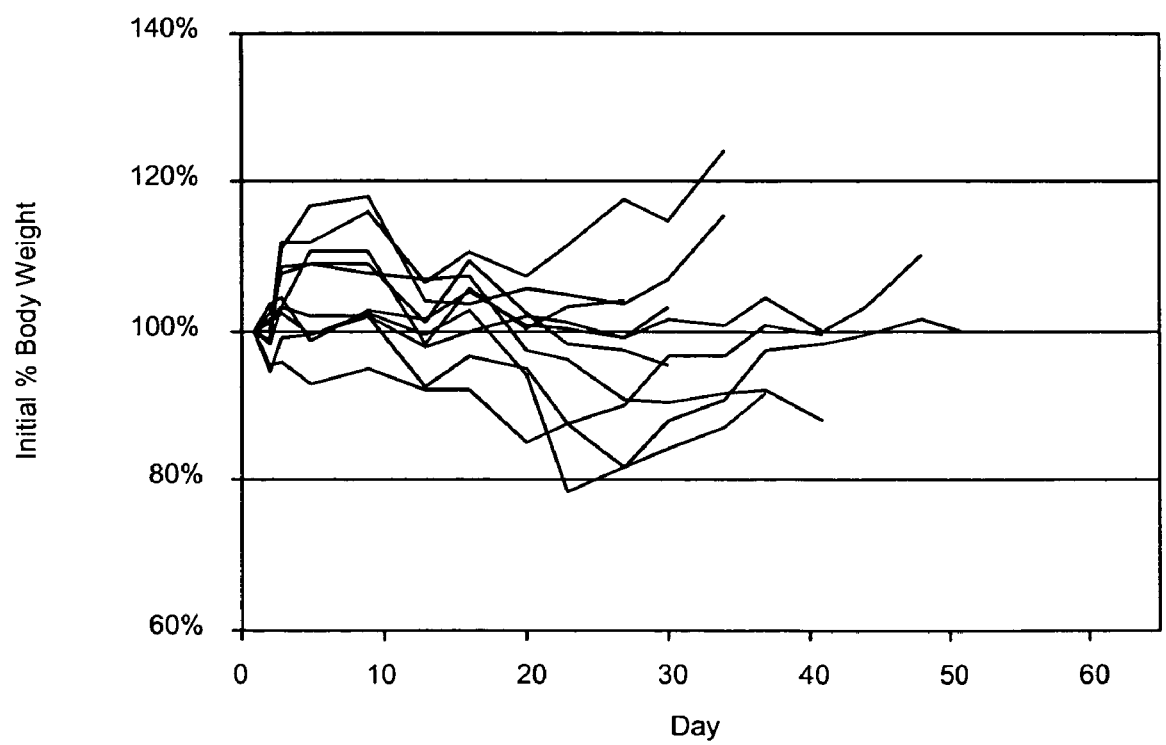
FIG. 6 sets forth data showing methods and compounds of the present invention were effective at limiting weight loss associated with administration of the chemotherapeutic agent Paclitaxel.

In animals administered either chemotherapeutic agent in combination with Compound A, the weight loss associated with chemotherapy administration was reduced. Following administration of Paclitaxel and Compound A (FIG. 6), fewer animals showed weight loss compared to that of animals administered Paclitaxel alone (FIG. 5). Additionally, administration of Paclitaxel and Compound A resulted in a higher number of animals which either maintained body weight or showed an increase in body weight compared to that in animals administered Paclitaxel alone. (Compare FIG. 5 and FIG. 6.) In particular, 4 or 10 animals in the combined Paclitaxel and Compound A treatment group ended the study at a body weight below that at the start of the study, compared to only 2 of 10 animals in the Paclitaxel alone treatment group. Additionally, administration of paclitaxel and Compound A resulted in a delay in the initial (early) weight loss in animals compared to that on animals administered Paclitaxel alone. (Compare weight loss patterns from day 0 to day 20 in FIG. 5 and FIG. 6.)

Figure 7:
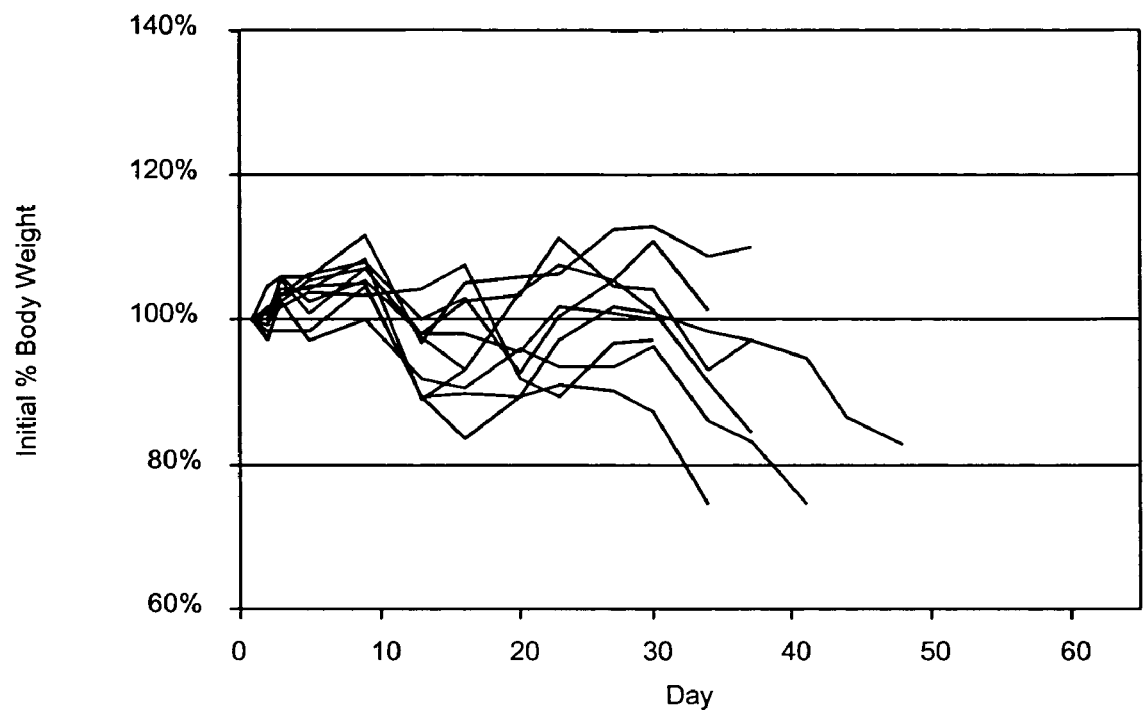
FIG. 7 sets forth data showing sets forth data showing body weight loss in animals administered the chemotherapeutic agent Carboplatin.
Figure 8:
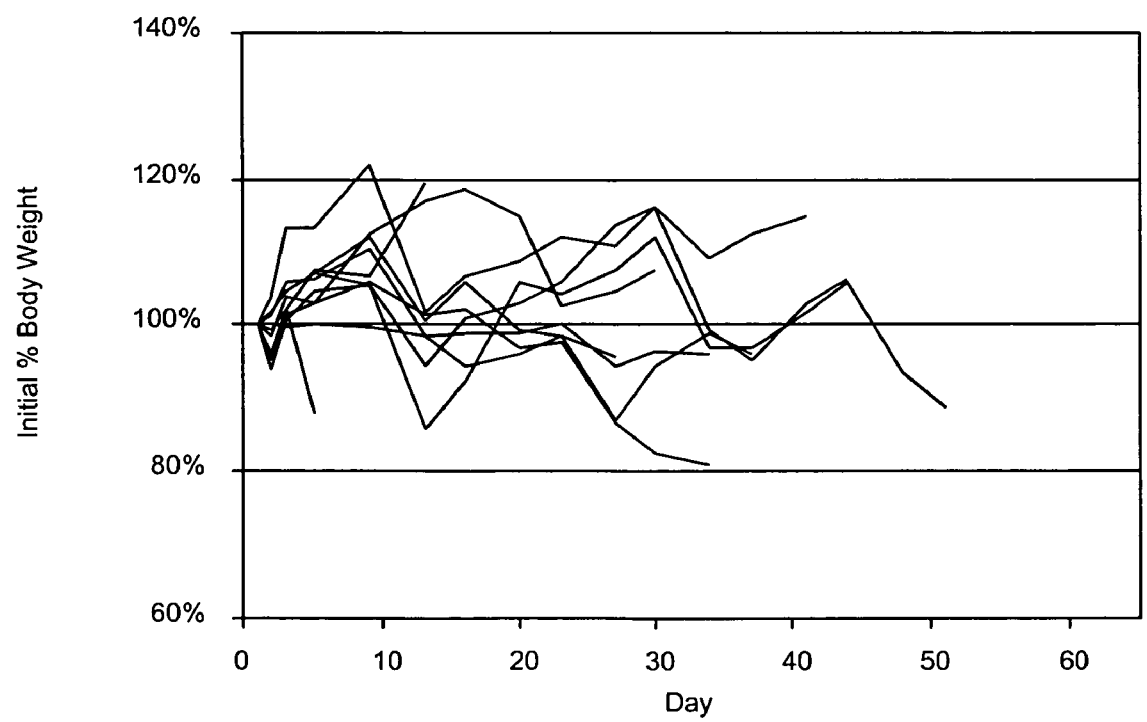
FIG. 8 sets forth data showing methods and compounds of the present invention were effective at limiting weight loss associated with administration of the chemotherapeutic agent Carboplatin.

Similar results were observed in animals administered Carboplatin and Compound A. Following administration of Carboplatin and Compound A (FIG. 8), fewer animals showed weight loss compared to that of animals administered Carboplatin alone (FIG. 7). In particular, 7 of 10 animals in the Carboplatin alone treatment group ended the study below starting weights, and only 3 of 10 animals in this group had more than a 10% weight gain at any time during the study. In contrast, when Carboplatin was combined with Compound A administration, animals showed substantially less severe weight loss compared to animals administered Carboplatin alone. In particular, 6 of 10 animals in the Carboplatin and Compound A treatment group ended the study below starting weights, and 7 of 10 animals in this treatment group had a 10% or greater weight gain during the course of the study. Additionally, premature morbidity in the Carboplatin treatment groups was observed and was correlated with weight loss (data not shown). All animals in this treatment group dropped below starting weights.

Thus, compounds and methods of the invention can be used to suppress weight loss associated with treatment with carboplatin. The observation of a beneficial suppression of body weight loss with known cancer chemotherapeutics of diverse mechanism of action indicates the broad utility of the present invention with respect to combined treatment regimens.

Various modifications of the invention, in addition to those shown and described herein, will become apparent to those skilled in the art from the foregoing description. Such modifications are intended to fall within the scope of the appended claims.

All references cited herein are hereby incorporated by reference herein in their entirety.

What is claimed is:

1. A method for treating chemotherapy-induced anemia in a subject refractory to recombinant human EPO therapy, the method comprising the steps of determining whether the subject is refractory to recombinant human EPO therapy and administering to the subject an effective amount of an agent that inhibits hypoxia inducible factor (HIF) hydroxylase activity.

2. The method of claim 1, wherein the subject is undergoing chemotherapy.

3. The method of claim 1, wherein the subject has undergone chemotherapy.

4. The method of claim 1, wherein the subject is expected to undergo chemotherapy.

5. The method of claim 1, wherein the chemotherapy comprises administration of a chemotherapeutic selected from the group consisting of: an alkylating agent; a nitrosoureas;
   an antimetabolite; an anthracyclines; a topoisomerase II inhibitor; a mitotic inhibitor; an anti-estrogen; a progestin; an aromatase inhibitor; an anti-androgen; an LHRH agonist; a corticosteroid hormone; a DNA alkylating agent; a taxane; a vince alkaloid; and a microtubule poison.

6. The method of claim 1, wherein the chemotherapeutic is selected from the group consisting of busulfan, cisplatin, carboplatin, chlorambucil, cyclophosphamide, ifosfamide, dacarbazine (DTIC), mechlorethamine (nitrogen mustard), melphalan, temozolomide, carmustine (BCNU), lomustine (CCNU), 5-fluorouracil, capecitabine, 6-mercaptopurine, methotrexate, gemcitabine, cytarabine (ara-C), fludarabine, pemetrexed, daunorubicin, doxorubicin (Adriamycin), epirubicin, idarubicin, mitoxantrone, topotecan, irinotecan, etoposide (VP-16), teniposide, paclitaxel, docetaxel, vinbiastine, vincristine, vinorelbine, prednisone, dexamethasone, L-asparaginase, dactinomycin, thalidomide, tretinoin, imatinib (Gleevec), gefitinib (Iressa), erlotinib (Tarceva), rituximab (Rituxan), bevacizumab (Avastin), tamoxifen, fulvestrant, anastrozole, exemestane, letrozole, megestrol acetate, bicalutamide, flutamide, leuprolide, and goserelin.

7. The method of claim 1, wherein the agent is a 2-oxoglutarate mimetic.

8. The method of claim 1, wherein the agent is administered orally, systemically, intravenously, or by injection.

* * * * *